US009873705B2

(12) United States Patent
Sanchez et al.

(10) Patent No.: US 9,873,705 B2
(45) Date of Patent: Jan. 23, 2018

(54) VINYLOGOUS THIOESTER COMPOUNDS AND METHODS OF USE

(71) Applicant: THE TRUSTEES OF DARTMOUTH COLLEGE, Hanover, NH (US)

(72) Inventors: Yolanda Sanchez, Orford, NH (US); Robert Allaway, Norwich, VT (US); Stephanie Bouley, North Smithfield, RI (US); Matthew Wood, San Francisco, CA (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/282,644

(22) Filed: Sep. 30, 2016

(65) Prior Publication Data
US 2017/0152262 A1   Jun. 1, 2017

Related U.S. Application Data

(60) Provisional application No. 62/236,843, filed on Oct. 2, 2015.

(51) Int. Cl.
| A61K 31/435 | (2006.01) |
| A61K 31/415 | (2006.01) |
| A61K 31/4192 | (2006.01) |
| A61K 31/4196 | (2006.01) |
| A61K 31/421 | (2006.01) |
| C07D 487/04 | (2006.01) |
| C07D 401/12 | (2006.01) |
| C07D 471/04 | (2006.01) |
| C07D 413/12 | (2006.01) |
| C07D 417/12 | (2006.01) |
| C07D 401/14 | (2006.01) |
| C07D 409/14 | (2006.01) |
| C07D 271/07 | (2006.01) |
| C07D 249/12 | (2006.01) |
| C07D 233/84 | (2006.01) |
| C07D 277/36 | (2006.01) |
| C07D 263/46 | (2006.01) |
| C07D 257/04 | (2006.01) |
| C07D 333/34 | (2006.01) |
| C07D 285/08 | (2006.01) |
| C07D 271/113 | (2006.01) |
| C07D 285/125 | (2006.01) |
| C07D 403/04 | (2006.01) |
| C07D 409/04 | (2006.01) |
| C07D 401/06 | (2006.01) |
| C07D 401/04 | (2006.01) |
| C07D 409/06 | (2006.01) |

(52) U.S. Cl.
CPC ......... *C07D 487/04* (2013.01); *C07D 233/84* (2013.01); *C07D 249/12* (2013.01); *C07D 257/04* (2013.01); *C07D 263/46* (2013.01); *C07D 271/07* (2013.01); *C07D 271/113* (2013.01); *C07D 277/36* (2013.01); *C07D 285/08* (2013.01); *C07D 285/125* (2013.01); *C07D 333/34* (2013.01); *C07D 401/04* (2013.01); *C07D 401/06* (2013.01); *C07D 401/12* (2013.01); *C07D 401/14* (2013.01); *C07D 403/04* (2013.01); *C07D 409/04* (2013.01); *C07D 409/06* (2013.01); *C07D 409/14* (2013.01); *C07D 413/12* (2013.01); *C07D 417/12* (2013.01); *C07D 471/04* (2013.01)

(58) Field of Classification Search
CPC ............... A61K 31/435; A61K 31/315; A61K 31/4192; A61K 31/4196; A61K 31/421; C07D 487/04; C07D 233/84
See application file for complete search history.

(56) References Cited

U.S. PATENT DOCUMENTS

2004/0006011 A1   1/2004 Gour et al.

FOREIGN PATENT DOCUMENTS

| SU | 259895 A | 12/1969 |
| WO | 2013/033520 A1 | 3/2013 |
| WO | 2014/022923 A1 | 2/2014 |

OTHER PUBLICATIONS

Ahmed et al. (1994) "A new rapid and simple nonradioactive assay to monitor and determine the proliferation of lymphocytes: an alternative to [3H]thymidine incorporation assay," J Immunol Methods. 170(2):211-24.
Alley et al. (1988) "Feasibility of drug screening with panels of human tumor cell lines using a microculture tetrazolium assay," Cancer Res. 48(3):589-601.
Arigo et al. (Mar. 3, 2006) "Regulation of yeast NRD1 expression by premature transcription termination," Mol Cell. 21(5):641-51.
Arigo et al. (Sep. 15, 2006) "Termination of cryptic unstable transcripts is directed by yeast RNA-binding proteins Nrd1 and Nab3," Mol Cell. 23(6):841-51.
Balzi et al. (1995) "Yeast multidrug resistance: the PDR network," J Bioenerg Biomembr. 27(1):71-6.
Bellot et al. (2013) "ROS, autophagy, mitochondria and cancer: Ras, the hidden master?" Mitochondrion. 13(3):155-62.
Boquoi et al. (2009) "Chemoprevention of mouse intestinal tumorigenesis by the cyclin-dependent kinase inhibitor SNS-032," Cancer Prev Res (Phila Pa). 2(9):800-6.
Cancer Genome Atlas Research Network (2008) "Comprehensive genomic characterization defines human glioblastoma genes and core pathways," Nature. 455(7216):1061-8.
Cancer Genome Atlas Research Network (2011) "Integrated genomic analyses of ovarian carcinoma," Nature. 474(7353):609-15.
Carroll et al. (2008) "How does the Schwann cell lineage form tumors in NF1?" Glia. 56(14):1590-605.

(Continued)

*Primary Examiner* — Rebecca L Anderson
*Assistant Examiner* — Karen Cheng
(74) *Attorney, Agent, or Firm* — Lathrop Gage LLP

(57) ABSTRACT

Provided herein are vinylogous thioester compounds and methods for using the compounds.

19 Claims, 19 Drawing Sheets

(56) References Cited

OTHER PUBLICATIONS

Chang et al. (2004) "The Ras/PKA signaling pathway directly targets the Srb9 protein, a component of the general RNA polymerase II transcription apparatus," Mol Cell. 15(1):107-16.
Chang et al. (2011) "LIBSVM: A library for support vector machines," ACM Trans. Intell. Syst. Technol. 2(3):1-27.
Chen et al. (2012) "A restricted cell population propagates glioblastoma growth after chemotherapy," Nature. 488(7412):522-6.
Cichowski et al. (2003) "Dynamic regulation of the Ras pathway via proteolysis of the NF1 tumor suppressor," Genes Dev. 17(4):449-54.
Clark et al. (2003) "Analysis of protein tyrosine kinase inhibitors in recombinant yeast lacking the ERG6 gene," Chembiochem. 4(1):101-7.
Conrad et al. (2000) "A yeast heterogeneous nuclear ribonucleoprotein complex associated with RNA polymerase II," Genetics. 154(2):557-71.
Davis et al. (2010) "MRI-coupled fluorescence tomography quantifies EGFR activity in brain tumors," Acad Radiol. 17(3):271-6.
De Raedt et al. (2003) "Elevated risk for MPNST in NF1 microdeletion patients," Am J Hum Genet. 72(5):1288-92.
Dowsett et al. (2013) "Comparison of PAM50 risk of recurrence score with oncotype DX and IHC4 for predicting risk of distant recurrence after endocrine therapy," Journal of clinical oncology : official journal of the American Society of Clinical Oncology. 31:2783-90.
Evans et al. (2002) "Malignant peripheral nerve sheath tumours in neurofibromatosis 1," J Med Genet. 39(5):311-4.
Ferner et al. (2002) "International consensus statement on malignant peripheral nerve sheath tumors in neurofibromatosis," Cancer Res. 62(5):1573-7.
Flory et al. (2008) "Oral bioavailability of etoposide after administration of a single dose to tumor-bearing dogs," Am J Vet Res. 69(10):1316-22.
Gibbs-Strauss et al. (2009) "Diagnostic detection of diffuse glioma tumors in vive with molecular fluorescent probe-based transmission spectroscopy," Med Phys. 36(3):974-83.
Gibbs-Strauss et al. (2010) "Detecting epidermal growth factor receptor tumor activity in vivo during cetuximab therapy of murine gliomas," Acad Radiol. 17(1):7-17.
Graf et al. (2006) "Quality of life and psychological adjustment in children and adolescents with neurofibromatosis type 1," J Pediatr. 149(3):348-53.
Gudipati et al. (2008) "Phosphorylation of the RNA polymerase II C-terminal domain dictates transcription termination choice," Nat Struct Mol Biol. 15(8):786-94.
Guo et al. (2013) "Autophagy is required for mitochondrial function, lipid metabolism, growth, and fate of KRAS(G12D)-driven lung tumors," Autophagy. 9(10):1636-8.
Hollstein et al. (2013) "Identifying the Ubiquitin Ligase complex that regulates the NF1 tumor suppressor and Ras," Cancer Discov. 3(8):880-93.
Howard et al. (2001) "The Ras/PKA signaling pathway of *Saccharomyces cerevisiae* exhibits a functional interaction with the Sin4p complex of the RNA polymerase II holoenzyme," Genetics. 159(1):77-89.
Howard et al. (2003) "The Ras/PKA signaling pathway may control RNA polymerase II elongation via the Spt4p/Spt5p complex in *Saccharomyces cerevisiae*," Genetics. 165(3):1059-70.
Jessen et al. (2013) "MEK inhibition exhibits efficacy in human and mouse neurofibromatosis Tumors," J Clin Invest. 123(1):340-7.
Joachims (2006) "Training linear SVMs in linear time," Proceedings of the 12th ACM SIGKDD international conference on Knowledge discovery and data mining. p. 217.
Luesch et al. (2005) "A genomewide overexpression screen in yeast for small-molecule target identification," Chem Biol. 12(1):55-63.

McEntee et al. (2006) "Phase I and pharmacokinetic evaluation of the combination of orally administered docetaxel and cyclosporin A in tumor-bearing cats," J Vet Intern Med. 20(6):1370-5.
McEntee et al. (2006) "Phase I and pharmacokinetic evaluation of the combination of orally administered docetaxel and cyclosporin A in tumor-bearing dogs," Am J Vet Res. 67(6):1057-62.
McGaughran et al. (1999) "A clinical study of type 1 neurofibromatosis in north west England," J Med Genet. 36(3):197-203.
Miller et al. (2009) "Integrative genomic analyses of neurofibromatosis tumours identify SOX9 as a biomarker and survival gene," EMBO Mol Med. 1(4):236-48.
Miller et al. (2010) "Inhibition of Eyes Absent Homolog 4 expression induces malignant peripheral nerve sheath tumor necrosis," Oncogene. 29(3):368-79.
Mosch et al. (1996) "Ras2 signals via the Cdc42/Ste20/mitogen-activated protein kinase module to induce filamentous growth in *Saccharomyces cerevisiae*," Proc Natl Acad Sci. 93(11):5352-6.
Parker et al. (2009) "Supervised risk predictor of breast cancer based on intrinsic subtypes," Journal of clinical oncology: official journal of the American Society of Clinical Oncology. 27:1160-7.
Parsons et al. (2008) "An integrated genomic analysis of human glioblastoma multiforme," Science. 321(5897):1807-12.
Porter et al. (2009) "Survival in Malignant Peripheral Nerve Sheath Tumours: A Comparison between Sporadic and Neurofibromatosis Type 1-Associated Tumours," Sarcoma. 2009:756395.
Rassnick et al. (2006) "Phase I trial and pharmacokinetic analysis of ifosfamide in cats with sarcomas," Am J Vet Res. 67(3):510-6.
Rutkowski et al. (2000) "Genetic and cellular defects contributing to benign tumor formation in neurofibromatosis type 1," Hum Mol Genet. 9(7):1059-66.
Scholl et al. (2009) "Synthetic lethal interaction between oncogenic KRAS dependency and STK33 suppression in human cancer cells," Cell. 137(5):821-34.
Simon et al. (2004) "Yeast as a model system for anticancer drug discovery," Nat Rev Cancer. 4(6):481-92.
Steinmetz et al. (2001) "RNA-binding protein Nrd1 directs poly(A)-independent 3'-end formation of RNA polymerase II transcripts," Nature. 413(6853):327-31.
Tanaka et al. (1990) "S. cerevisiae genes IRA1 and IRA2 encode proteins that may be functionally equivalent to mammalian ras GTPase activating protein," Cell. 60(5):803-7.
Thiebaut et al. (2006) "Transcription termination and nuclear degradation of cryptic unstable transcripts: a role for the nrdl-nab3 pathway in genome surveillance," Mol Cell. 23(6):853-64.
Toda et al. (1985) "In yeast, RAS proteins are controlling elements of adenylate cyclase," Cell. 40(1):27-36.
Torrance et al. (2001) "Use of isogenic human cancer cells for high-throughput screening and drug discovery," Nat Biotechnol. 19(10):940-5.
Tucker et al. (2001) "A yeast sensor of ligand binding," Nat Biotechnol. 19(11):1042-6.
Van Swieten et al. (2007) "A cell-permeable inhibitor and activity-based probe for the caspase-like activity of the proteasome," Bioorg Med Chem Lett. 17(12):3402-5.
Verdoes et al. (2008) "Azido-BODIPY acid reveals quantitative Staudinger-Bertozzi ligation in two-step activity-based proteasome profiling," Chembiochem. 9(11):1735-8.
Verhaak et al. (2010) "Integrated genomic analysis identifies clinically relevant subtypes of glioblastoma characterized by abnormalities in PDGFRA, IDH1, EGFR, and NF1," Cancer Cell. 17(1):98-110.
Williams et al. (2008) "Nf1 mutation expands an EGFR-dependent peripheral nerve progenitor that confers neurofibroma tumorigenic potential," Cell Stem Cell. 3(6):658-69.
Wright et al. (1996) "Measurement and analysis of unbound drug concentrations," Clin Pharmacokinet. 30(6):445-62.
Wu et al. (2008) "Plexiform and dermal neurofibromas and pigmentation are caused by Nf1 loss in desert hedgehogexpressing cells," Cancer Cell. 13(2):105-16.
Wu et al. (2012) "Preclincial testing of sorafenib and RAD001 in the Nf(flox/flox); DhhCre mouse model of plexiform neurofibroma using magnetic resonance imaging," Pediatr Blood Cancer. 58(2):173-80.

(56) References Cited

OTHER PUBLICATIONS

Xu et al. (2002) "Gene-targeted deletion of neurofibromin enhances the expression of a transient outward K+ current in Schwann cells: a protein kinase A-mediated mechanism," J Neurosci. 22(21):9194-202.
Zheng et al. (2008) "Induction of abnormal proliferation by nonmyelinating schwann cells triggers neurofibroma formation," Cancer Cell. 13(2):117-28.
Zhu et al. (2002) "Neurofibromas in NF1: Schwann cell origin and role of tumor environment," Science. 296(5569):920-2.
Zoller et al. (1997) "Malignant and benign tumors in patients with neurofibromatosis type 1 in a defined Swedish population," Cancer. 79(11):2125-31.
Alcantara Llaguno et al. (Oct. 1, 2015) "Adult Lineage-Restricted CNS Progenitors Specify Distinct Glioblastoma Subtypes," Cancer Cell. 28(4):429-440.
Al-Mehdi et al. (Jul. 3, 2012) "Perinuclear Mitochondrial Clustering Creates an Oxidant-Rich Nuclear Domain Required for Hypoxia-Induced Transcription," Sci. Signal. 5(231):ra47. pp. 1-11.
Bellot et al. (2009) "Hypoxia-Induced Autophagy Is Mediated through Hypoxia-Inducible Factor Induction of BNIP3 and BNIP3L via Their BH3 Domains," Mol Cell Biol. 29(10):2570-2581.
Bourne et al. (1991) "The GTPase superfamily: conserved structure and molecular mechanism," Nature. 349 (6305):117-127.
Carli et al. (2005) "Pediatric malignant peripheral nerve sheath tumor: the Italian and German soft tissue sarcoma cooperative group," J. Clin. Oncol. 23(33):8422-30.
Chourasia et al. (Mar. 26, 2015) "Mitophagy and cancer," Cancer Metab. 3:4.
Declue et al. (1992) "Abnormal regulation of mammalian p21 ras contributes to malignant tumor growth in von Recklinghausen (type 1) neurofibromatosis," Cell. 69(2):265-273.
Endo et al. (Jan. 2, 2013) "Prognostic significance of Akt/mTOR and MAPK pathways and antitumor effect of mTOR inhibitor in NFI-related and sporadic malignant peripheral nerve sheath tumors," Clin. Cancer Res. 19(2):450-61.
Glick et al. (2010) "Autophagy: cellular and molecular mechanisms," J. Pathol. 221(1):3-12.
Guo et al. (2011) "Activated Ras requires autophagy to maintain oxidative metabolism and tumorigenesis," Gene Dev. 25(5):460-470.
Hamacher-Brady et al. (Feb. 1, 2016) "Mitophagy programs: mechanisms and physiological implications of mitochondrial targeting by autophagy," Cell. Mol. Life Sci. 73(4):775-95.
Holzel et al. (2010) "NF1 is a tumor suppressor in neuroblastoma that determines retinoic acid response and disease outcome," Cell. 142(2):218-29.
Kaelin (2005) "The concept of synthetic lethality in the context of anticancer therapy," Nat Rev. Cancer. 5(9):689-98.
Kaluz et al. (2006) "Proteasomal inhibition attenuates transcriptional activity of hypoxia-inducible factor 1 (HIF-1) via specific effect on the HIF-1alpha C-terminal activation domain," Mol. Cell Biol. 26(15):5895-5907.
Keng et al. (Jun. 14, 2012) "PTEN and NF1 inactivation in Schwann cells produces a severe phenotype in the peripheral nervous system that promotes the development and malignant progression of peripheral nerve sheath tumors," Cancer Res. 72(13):3405-3413.
Kim et al. (2001) "Schwann cell proliferative responses to cAMP and Nf1 are mediated by cyclin D1," J. Neurosci. 21 (4):1110-6.
Korf (2000) "Malignancy in Neurofibromatosis Type 1," Oncol. 5(6):477-485.
Lee et al. (Jan. 15, 2012) "Autophagy, mitochondria and oxidative stress: cross-talk and redox signalling," Biochem. J. 441(2):523-540.
Liu et al. (Jun. 6, 2014) "Receptor-mediated mitophagy in yeast and mammalian systems," Cell Res. 2014;24 (7):787-795.
McGillicuddy et al. (2009) "Proteasomal and Genetic Inactivation of the NF1 Tumor Suppressor in Gliomagenesis," Cancer Cell. 16(1):44-54.
Murakawa et al. (Jul. 6, 2015) "Bcl-2-like protein 13 is a mammalian Atg32 homologue that mediates mitophagy and mitochondrial fragmentation," Nat Commun. 2015;6:7527.
National Cancer Institute "Phase II Trial of the MEK1/2 Inhibitor Selumetinib (AZD6244 Hydrogen Sulfate) in Adults With Neurofibromatosis Type 1 (NF1) and Inoperable Plexiform Neurofibromas," Accessible on the Internet at URL: https://clinicaltrials.gov/show/NCT02644512. [Last Accessed May 11, 2017], 6 pgs.
Oslo University Hospital et al. "A Phase II Study of Pembrolizumab in Patients With Malignant Peripheral Nerve Sheath Tumor (MPMST), Not Eligible for Curative Surgery," Accessible on the Internet at URL: https://clinicaltrials.gov/show/NCT02691026. [Last Accessed May 11, 2017], 4 pgs.
Padmavathi et al. (2006) "Studies on Reactivity of Bisolefinic Diketo Sulfides/Sulfones. II," Synthetic Communications. 33(22):3879-3889.
Sarcoma Alliance for Research Through Collaboration et al. "Phase 2 Study of the mTOR Inhibitor Everolimus in Combination With Bevacizumab in Patients With Sporadic and Neurofibromatosis Type 1 (NF1) Related Refractory Malignant Peripheral Nerve Sheath Tumors," Accessible on the Internet at URL: https://clinicaltrials.gov/show/NCT01661283. [Last Accessed May 11, 2017], 4 pgs.
Sarcoma Alliance for Research Through Collaboration et al. "A Phase I/II Trial of Ganetespib in Combination With the mTOR Inhibitor Sirolimus for Patients With Recurrent or Refractory Sarcomas Including Unresectable or Metastatic Malignant Peripheral Nerve Sheath Tumors," Accessible on the Internet at URL: https://clinicaltrials.gov/show/NCT02008877. [Last Accessed May 11, 2017], 4 pgs.
Sordillo et al. (1981) "Malignant schwannoma-clinical characteristics, survival, and response to therapy," Cancer. 47(10):2503-9.
STN Chemical Catalogue [Online] (Entered Jan. 23, 2008) Registry No. 1000568-17-1, 1 pg.
STN Chemical Catalogue [Online] (Entered Jul. 19, 2004) Registry No. 712297-29-5, 1 pg.
STN Chemical Catalogue [Online] (Entered Jul. 26, 2007) Registry No. 943423-77-6, 1 pg.
Tracy et al. (2007) "BNIP3 Is an RB/E2F Target Gene Required for Hypoxia-Induced Autophagy," Mol Cell Biol. 27 (17):6229-6242.
University of Alabama at Birmingham "A Phase 2 Trial of the MEK Inhibitor PD-0325901 in Adolescents and Adults With NF1-Associated Morbid Plexiform Neurofibromas," Accessible on the Internet at URL: https://clinicaltrials.gov/show/NCT02096471. [Last Accessed May 11, 2017], 6 pgs.
Wood et al. (2011) "Discovery of a small molecule targeting IRA2 deletion in budding yeast and neurofibromin loss in malignant peripheral nerve sheath tumor cells," Mol. Cancer Ther. 10(9):1740-50.
International Search Report with Written Opinion corresponding to International Patent Applicatino No. PCT/US2016/054892, dated Feb. 9, 2017.

VINYLOGOUS THIOESTER COMPOUNDS AND METHODS OF USE

RELATED APPLICATIONS

This application claims the benefit of U.S. Provisional Application No. 62/236,843, filed Oct. 2, 2015, the content of which is incorporated herein by reference in its entirety.

BACKGROUND

NF1 is a GTPase activating protein (GAP) that negatively regulates the activity of Ras by accelerating the conversion rate of Ras-bound GTP to GDP via GTP hydrolysis. Loss of functional NF1 protein due to mutations in the NF1 gene causes the autosomal dominant disorder neurofibromatosis type 1 (NF1) (1). Children with NF1 will develop tumors throughout their lifetime, with tumor frequency increasing as they age. Plexiform neurofibromas (PNs) pose the greatest threat to NF1 patients, as they can transform into malignant peripheral nerve sheath tumors (MPNSTs), highly resistant sarcomas with a 5-year survival of 16-38% (2-4). NF1 loss is also considered contributive to the development of aggressive neurological cancers, including glioblastoma and neuroblastoma (5-7). While there are clinical trials investigating new therapies for NF1 deficient PNs and MPNSTs, such as MEK inhibitor therapy, PD-1-targeted immunotherapy, and mTOR inhibitor combination therapy, there still exists a critical need for novel therapeutics (8-12).

SUMMARY

In one aspect, provided herein is a compound having the structure of Formula (I):

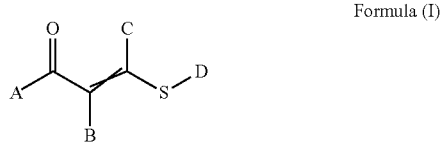

Formula (I)

or a pharmaceutically acceptable salt thereof; wherein:

A is selected from the group consisting of phenyl, pyridyl, and pyrimidinyl; wherein A is optionally substituted with 1-3 substituents independently selected from the group consisting of halo, cyano, $C_1$-$C_6$ alkyl, $C_3$-$C_6$ cycloalkyl, $C_1$-$C_6$ haloalkyl, $C_1$-$C_6$ alkoxy, and $C_1$-$C_6$ thioalkyl;

B is selected from H, halo and $C_1$-$C_6$ alkyl;

C is selected from H, halo and $C_1$-$C_6$ alkyl;

D is a heteroaryl moiety; wherein

D is optionally substituted with 1-3 substituents independently selected from the group consisting of halo, hydroxy, cyano, $C_1$-$C_6$ alkyl, $C_1$-$C_6$ alkyl-C(O)NH$_2$, $C_1$-$C_6$ alkyl-C(O)N($C_1$-$C_6$ alkyl)$_2$, $C_1$-$C_6$ alkyl-S(O)$_x$($C_1$-$C_6$ alkyl), $C_1$-$C_6$ alkyl-$C_3$-$C_6$ heterocycloalkyl, $C_1$-$C_6$ alkyl-heteroaryl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ alkoxy-$C_1$-$C_6$ alkyl, $C_1$-$C_6$ thioalkyl, aryl and heteroaryl;

wherein x is 0, 1 or 2; and

⚹ represents a double bond having E or Z stereochemistry.

In another aspect, provided herein is a method for treating a disorder associated with Ras deregulation or dysregulation comprising administering to a subject in need of treatment an effective amount of a compound of the invention (e.g., a compound according to Formula (I), (Ia)-(Ig) or Table 2) or a pharmaceutically acceptable salt thereof.

In another aspect, provided herein is a method for inhibiting autophagy in a cell, comprising contacting the cell with a compound of the invention (e.g., a compound according to Formula (I), (Ia)-(Ig) or Table 2) or a pharmaceutically acceptable salt thereof.

In another aspect, provided herein is the use of a compound of the invention (e.g., a compound according to Formula (I), (Ia)-(Ig) or Table 2) or a pharmaceutically acceptable salt thereof, in a method for treating a disorder associated with Ras deregulation or dysregulation.

BRIEF DESCRIPTION OF THE DRAWINGS

FIG. 2A shows data in NF1 deficient yeast. FIG. 2B shows data in U87-MG cells.

FIG. 12A shows the yeast dose response assay for Y102. FIG. 12B shows the yeast dose response assay for Y102_55. FIG. 12C shows the yeast dose response assay for Y102_2. FIG. 12D shows the yeast dose response assay for JW_1.

FIG. 15A shows data for U251-MG. FIG. 15B shows data for U-87-MG.

DETAILED DESCRIPTION

Figure 1:
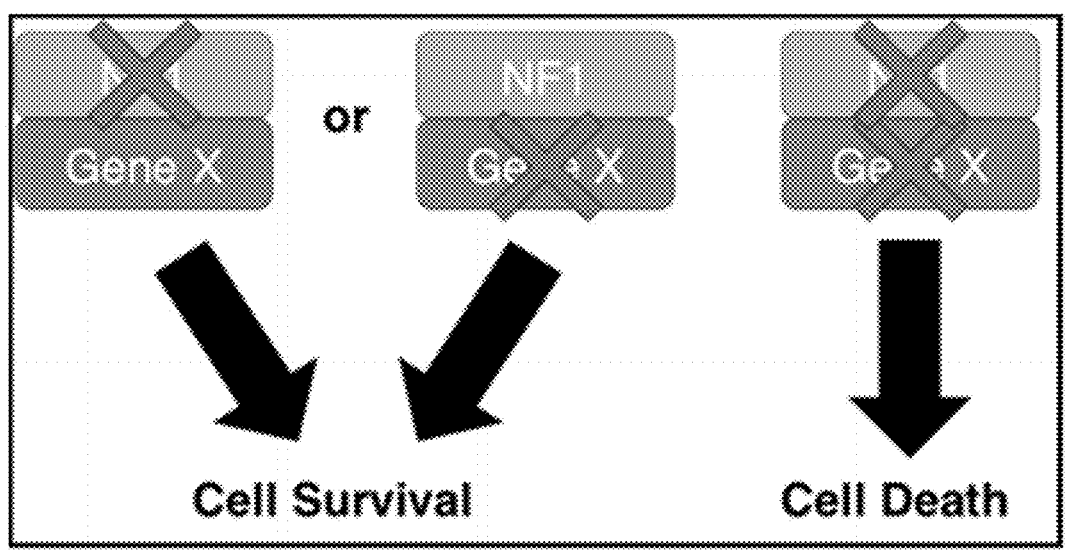
FIG. 1 shows a schematic of the model of synthetic lethality used in the compound screen disclosed herein. Synthetic lethality occurs when the loss of one of two genes results in cell survival, but the loss of both genes results in cell death. In this case, loss of NF1 or gene X alone results in cell survival, but the combined loss of both genes results in cell death.

NF1 is a GTPase activating protein (GAP) that negatively regulates the activity of Ras by accelerating the conversion rate of Ras-bound GTP to GDP via GTP hydrolysis (15). Loss of NF1 results in Ras hyperactivation and activation of the PI3K, BRAF, and mTOR pathways (16). Together, these pathways drive translation, cell proliferation, cell motility, and cell invasion.

A yeast-based screening platform was developed to identify compounds that are synthetic lethal with NF1 loss. Compounds were screened against yeast lacking IRA2 (ira2Δ), a yeast homologue of NFL Hit compounds inhibited the growth of ira2Δ cells at concentrations that had no effect on wild-type control strains. Using this approach, compound 64 (Y102) was identified. Top candidate compounds were tested in a number of NF1 dysregulated human cancer cell lines (6, 13). The targets of the compounds were identified through high-copy suppressor screens in yeast (14). Potential targets were then tested for synthetic lethality in combination with NF1 loss.

Exposure of several NF1 dysregulated human cancer cell lines to Y102 resulted in the accumulation of reactive oxygen species (ROS) and autophagy markers. Y102 treatment also resulted in an altered mitochondrial phenotype. The results suggest that Y102, and analogs and derivatives thereof (e.g., compounds of the invention) modulate mitophagy, a selective form of autophagy. The results further indicate that NF1 deficient cancers can be selectively targeted with the compounds of the invention and that modulation of autophagy/mitophagy is an effective therapeutic strategy in cancers with NF1 loss.

Compounds

Compounds of the invention (e.g., compounds according to Formulas (I) and (Ia)-(Ig) and Table 2), and pharmaceutically acceptable salts thereof) are provided herein. In certain embodiments, the compounds selectively inhibit NF1-deficient cells.

In one aspect, provided herein is a compound having the structure of Formula (I):

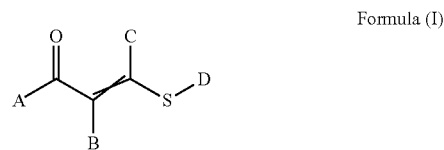

Formula (I)

or a pharmaceutically acceptable salt thereof; wherein:
A is selected from the group consisting of phenyl, pyridyl, and pyrimidinyl; wherein A is optionally substituted with 1-3 substituents independently selected from the group consisting of halo, cyano, $C_1$-$C_6$ alkyl, $C_3$-$C_6$ cycloalkyl, $C_1$-$C_6$ haloalkyl, $C_1$-$C_6$ alkoxy, and $C_1$-$C_6$ thioalkyl;
B is selected from H, halo and $C_1$-$C_6$ alkyl;
C is selected from H, halo and $C_1$-$C_6$ alkyl;
D is a heteroaryl moiety; wherein
D is optionally substituted with 1-3 substituents independently selected from the group consisting of halo, hydroxy, cyano, $C_1$-$C_6$ alkyl, $C_1$-$C_6$ alkyl-C(O)NH$_2$, $C_1$-$C_6$ alkyl-C(O)N($C_1$-$C_6$ alkyl)$_2$, $C_1$-$C_6$ alkyl-S(O)$_x$($C_1$-$C_6$ alkyl), $C_1$-$C_6$ alkyl-$C_3$-$C_6$ heterocycloalkyl, $C_1$-$C_6$ alkyl-heteroaryl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ alkoxy-$C_1$-$C_6$ alkyl, $C_1$-$C_6$ thioalkyl, aryl and heteroaryl;
wherein x is 0, 1 or 2; and
⤳ represents a double bond having E or Z stereochemistry.

In an embodiment, both B and C are selected from halo and $C_1$-$C_6$ alkyl. In an embodiment, one of B and C is selected from halo and $C_1$-$C_6$ alkyl, and the other of B and C is H. In an embodiment, B and C are both H.

In an embodiment, the double bond of Formula (I) has E stereochemistry. In an embodiment, the double bond of Formula (I) has Z stereochemistry.

In an embodiment, A is unsubstituted or is substituted with 1-3 substituents selected from the group consisting of —Cl, —F, —CN, —CH$_3$, —CHF$_2$, —CF$_3$, —OCH$_3$, —SCH$_3$, —OCHF$_2$, —OCF$_3$, —SCHF$_2$, and —SCF$_3$. In a particular embodiment, A is substituted with 1 substituent selected from the group consisting of —Cl, —F, —CN, —CH$_3$, —CHF$_2$, —CF$_3$, —OCH$_3$, —SCH$_3$, —OCHF$_2$, —OCF$_3$, —SCHF$_2$, and —SCF$_3$.

In an embodiment, A is phenyl. In an embodiment, A is pyridyl (e.g., 2-pyridyl).

In an embodiment, it is provided that:
i. when A is unsubstituted phenyl, D is not 3-methylthio-1,2,4-thiadiazol-5-yl, 1-methyl-tetrazol-5-yl, 1-phenyl-tetrazol-5-yl, 4-cyano-5-methyl-isothiazol-3-yl, or 4-phenyl-thiazol-2-yl, and D does not comprise a moiety selected from the group consisting of 1,2,4-triazolyl, pyridinyl, pyrimidinyl, benzimidazol-2-yl, benzoxazol-2-yl, benzothiazol-2-yl and purinyl;
ii. when A is 4-fluorophenyl, D is not 1-methylimidazol-2-yl, 1-phenyl-tetrazol-5-yl, 4-phenyl-thiazol-2-yl, or 4-methyl-1,2,4-triazol-3-yl, and D does not comprise a moiety selected from pyridinyl, pyrimidinyl, benzimidazol-2-yl, benzoxazol-2-yl, benzothiazol-2-yl; and
iii. when A is 4-chlorophenyl, D is not 1H-1,2,4-triazol-5-yl, 1-methylimidazol-2-yl, 1-methyl-tetrazol-5-yl, 1-phenyl-tetrazol-5-yl, 3-methylthio-1,2,4-thiadiazol-5-yl, 4-phenyl-thiazol-2-yl, and D does not comprise a moiety selected from pyridinyl, pyrimidinyl, benzimidazol-2-yl, benzoxazol-2-yl, benzothiazol-2-yl.

In an embodiment, Formula (I) has the structure of Formula (Ia), or a pharmaceutically acceptable salt thereof, wherein D is defined according to any embodiment disclosed herein:

Formula (Ia)

In an embodiment, Formula (I) has the structure of Formula (Ib), or a pharmaceutically acceptable salt thereof, wherein D is defined according to any embodiment disclosed herein:

Formula (Ib)

In an embodiment, Formula (I) has the structure of Formula (Ic), or a pharmaceutically acceptable salt thereof, wherein D is defined according to any embodiment disclosed herein:

Formula (Ic)

In an embodiment, Formula (I) has the structure of Formula (Id), or a pharmaceutically acceptable salt thereof, wherein D is defined according to any embodiment disclosed herein:

Formula (Id)

In an embodiment, Formula (I) has the structure of Formula (Ie), or a pharmaceutically acceptable salt thereof, wherein D is defined according to any embodiment disclosed herein:

Formula (Ie)

In an embodiment, Formula (I) has the structure of Formula (If), or a pharmaceutically acceptable salt thereof, wherein D is defined according to any embodiment disclosed herein:

Formula (If)

In an embodiment, Formula (I) has the structure of Formula (Ig), or a pharmaceutically acceptable salt thereof, wherein D is defined according to any embodiment disclosed herein:

Formula (Ig)

wherein n is 1 or 2.

In embodiments of Formulas (I) and (Ia)-(Ig), D is selected from Table 1:

TABLE 1

TABLE 1-continued
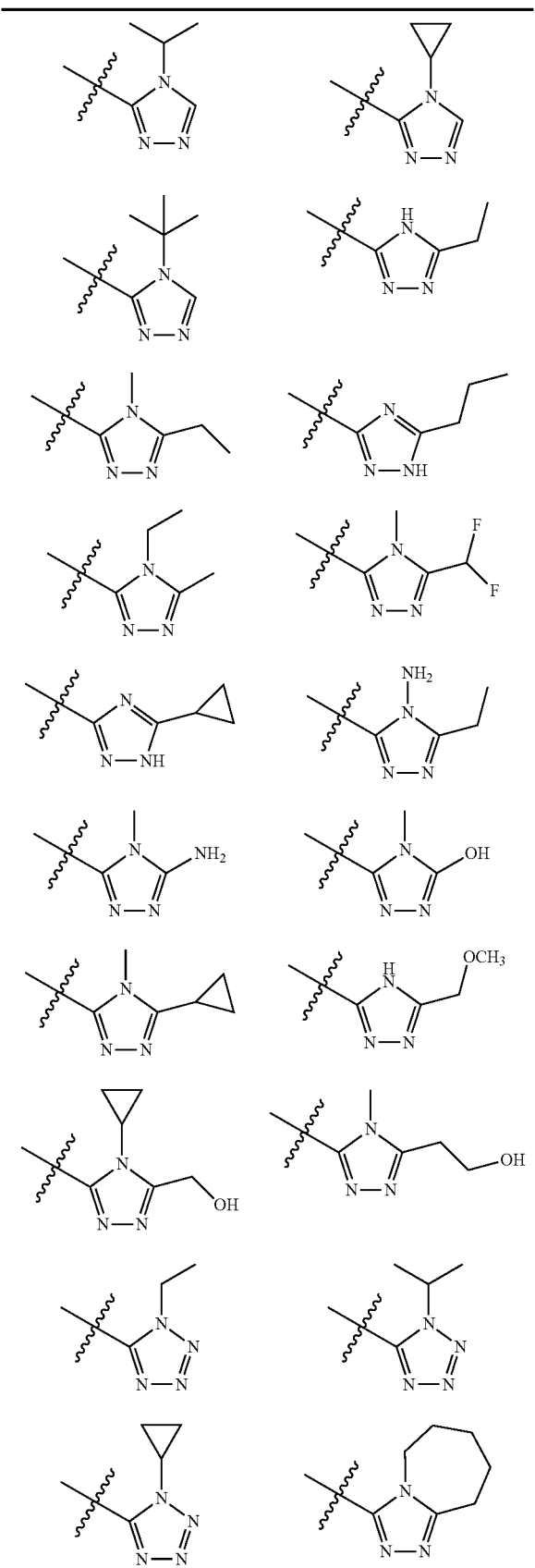
TABLE 1-continued
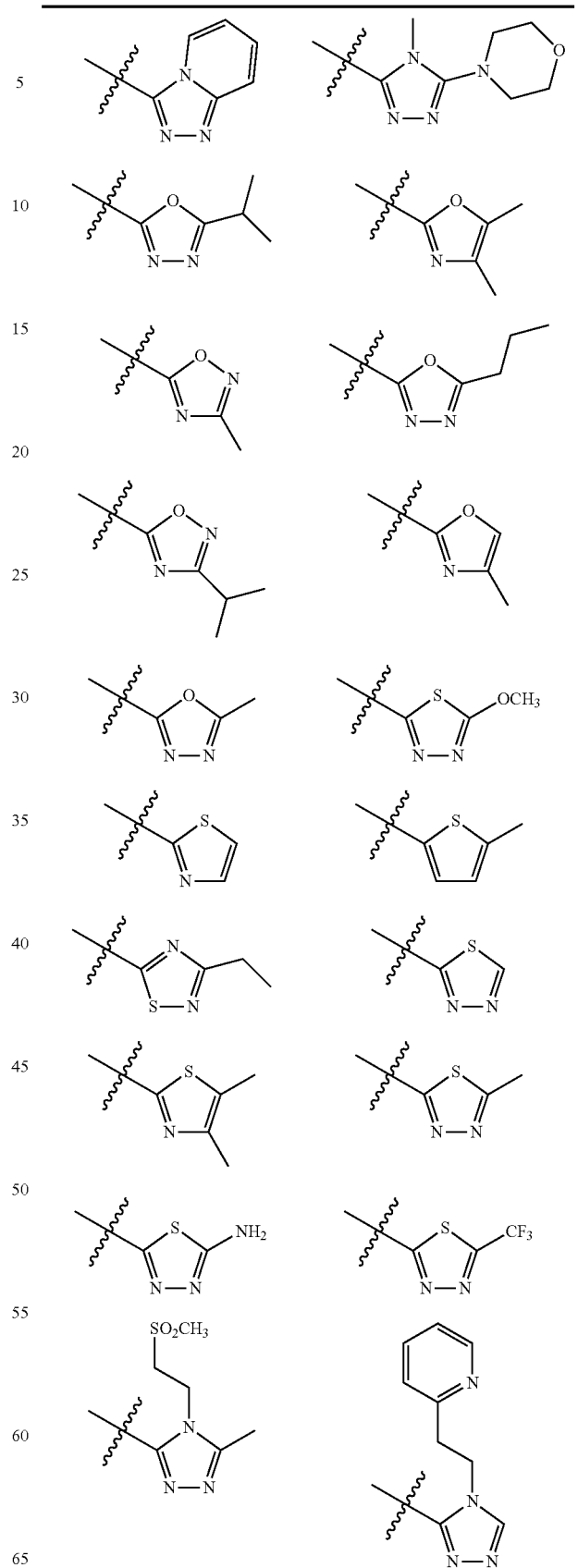

TABLE 1-continued
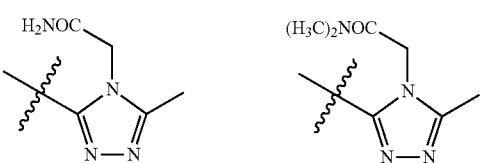
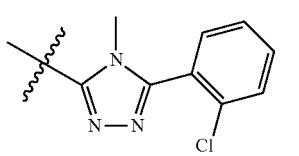 [SMILES: *c1nnc(-c2ccccc2Cl)n1C]
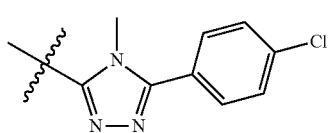 [SMILES: *c1nnc(-c2ccc(Cl)cc2)n1C]
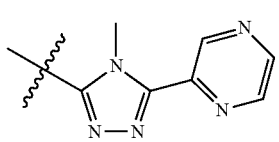 [SMILES: *c1nnc(-c2cnccn2)n1C]
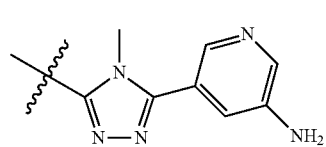
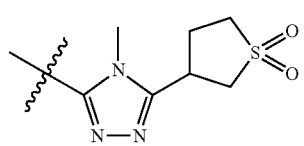 [SMILES: *c1nnc(C2CCS(=O)(=O)C2)n1C]
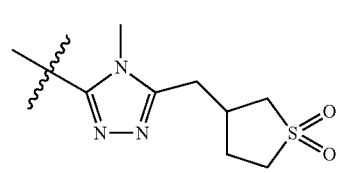 [SMILES: *c1nnc(CC2CCS(=O)(=O)C2)n1C]
provided that: (i) when A is unsubstituted phenyl, 4-methylphenyl, 4-methoxyphenyl, or 4-chlorophenyl, D is not 4-methyl-1,2,4-triazol-3-yl; and (ii) when A is 4-fluorophenyl, D is not 4-methyl-1,2,4-triazol-3-yl or 1-methylimidazol-2-yl.
In an embodiment, the compound of Formula (I) is selected from the compounds of Table 2, and pharmaceutically acceptable salts thereof:
TABLE 2
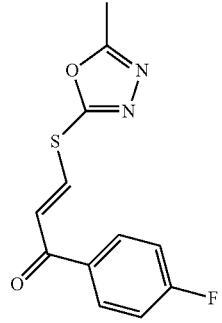 [SMILES: Cc1nnc(S/C=C/C(=O)c2ccc(F)cc2)o1]
1
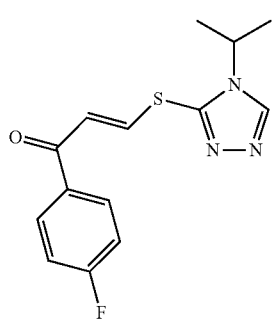 [SMILES: CC(C)n1cnnc1S/C=C/C(=O)c1ccc(F)cc1]
2
(Y102_2)
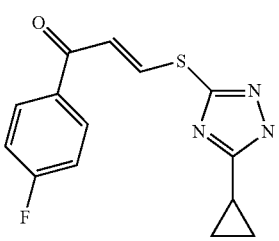 [SMILES: O=C(/C=C/Sc1n[nH]c(C2CC2)n1)c1ccc(F)cc1]
3
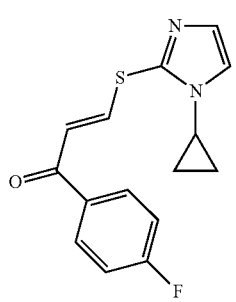 [SMILES: O=C(/C=C/Sc1nccn1C1CC1)c1ccc(F)cc1]
4
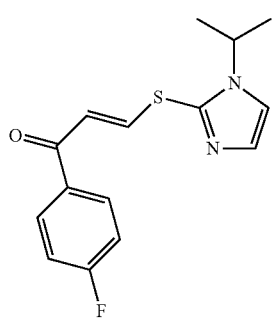 [SMILES: CC(C)n1ccnc1S/C=C/C(=O)c1ccc(F)cc1]
5

TABLE 2-continued
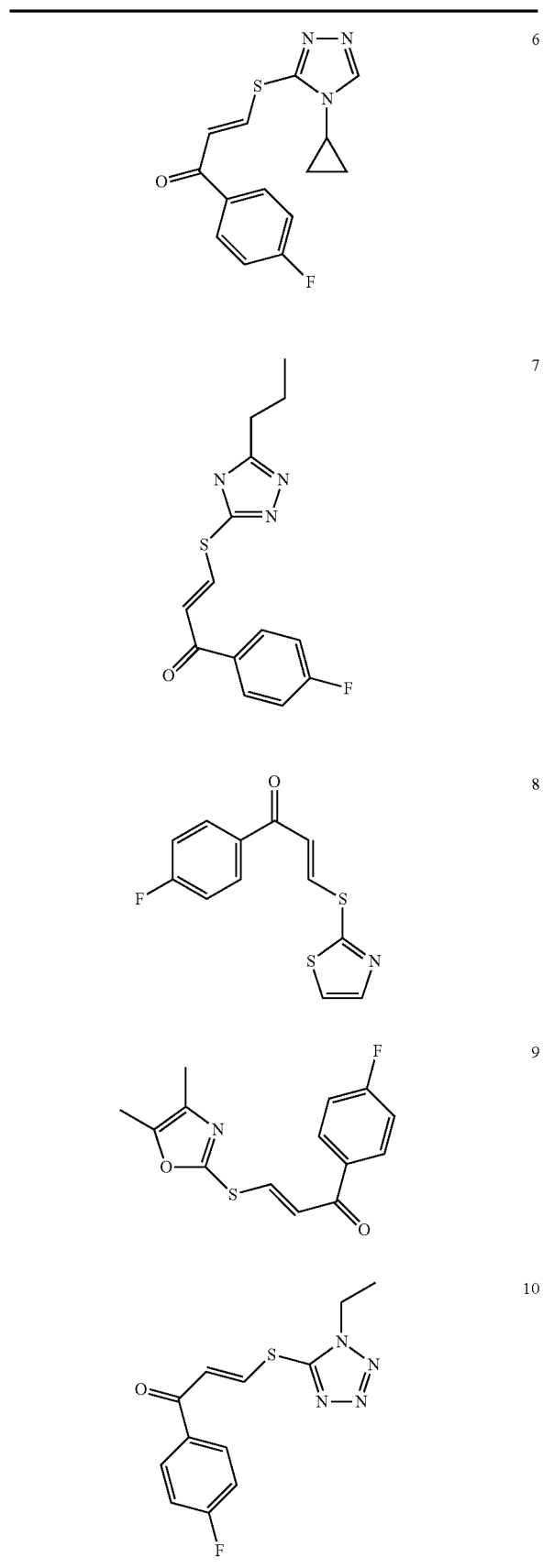
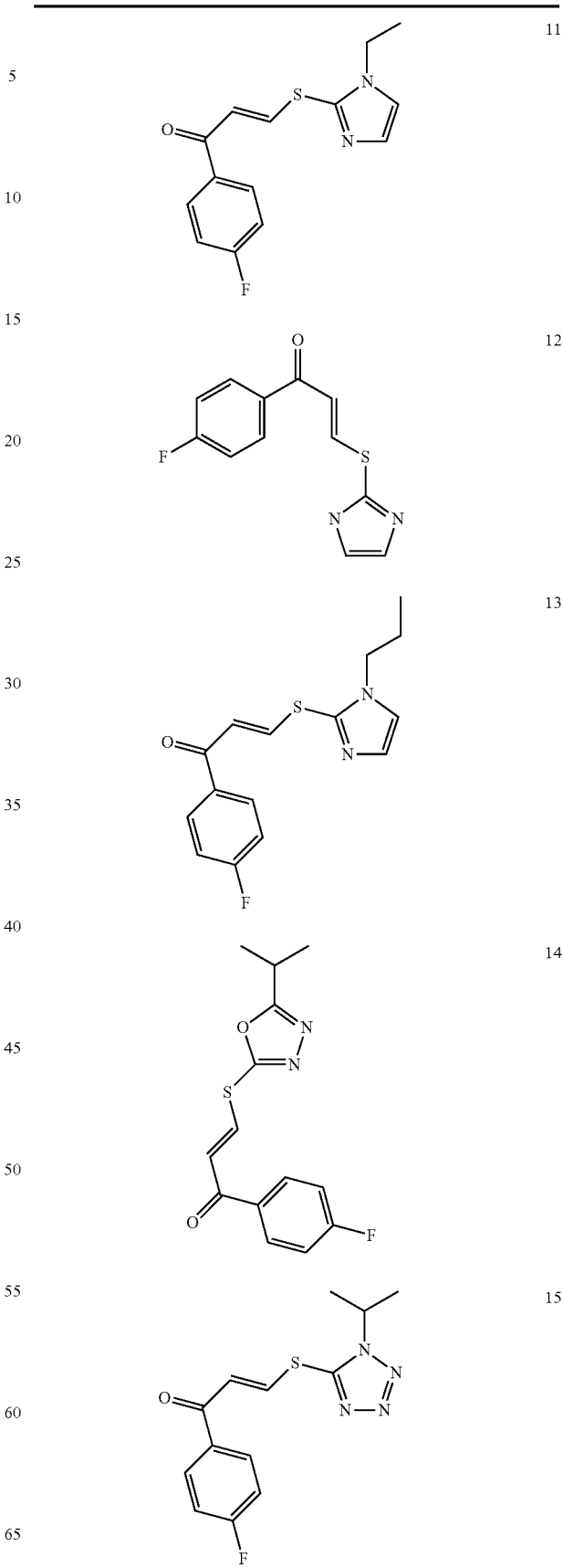

TABLE 2-continued
| | |
|---|---|
| 16 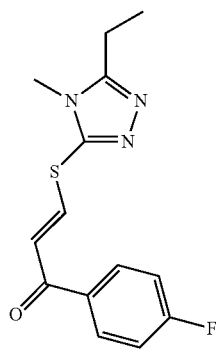 [SMILES: CCc1nnc(S/C=C/C(=O)c2ccc(F)cc2)n1C] | 21 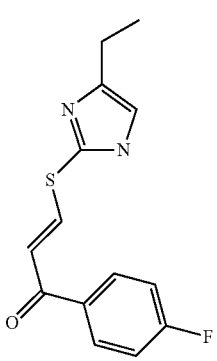 |
| 17 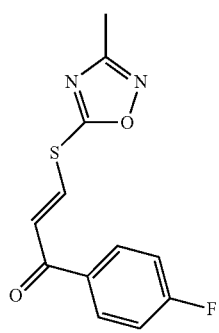 [SMILES: Cc1noc(S/C=C/C(=O)c2ccc(F)cc2)n1] | 22 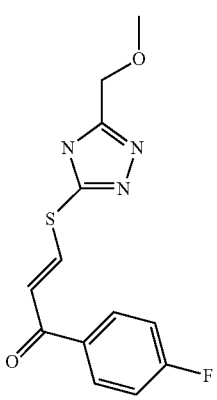 |
| 18 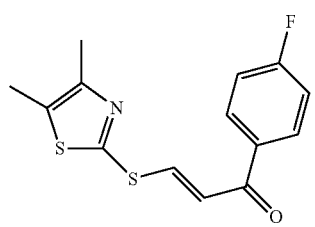 | 23 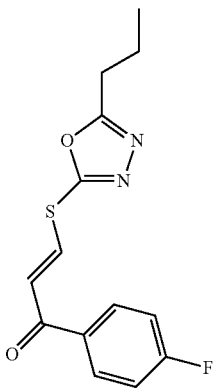 |
| 19 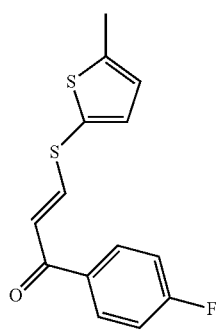 [SMILES: Cc1ccc(S/C=C/C(=O)c2ccc(F)cc2)s1] | 24 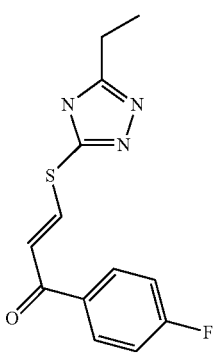 |
| 20 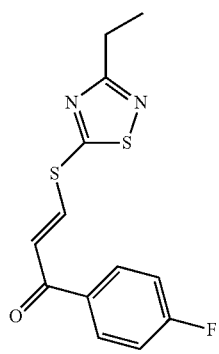 [SMILES: CCc1nsc(S/C=C/C(=O)c2ccc(F)cc2)n1] | |

TABLE 2-continued
| | |
|---|---|
| 25 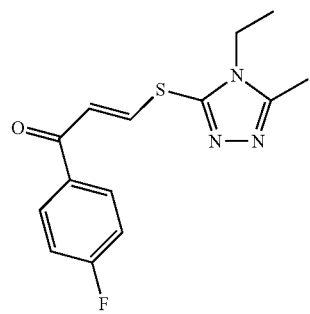 [SMILES: CCn1c(C)nnc1S/C=C/C(=O)c1ccc(F)cc1] | 30 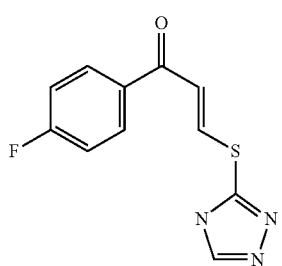 |
| 26 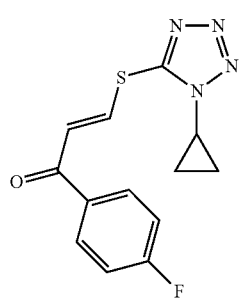 [SMILES: O=C(/C=C/Sc1nnnn1C1CC1)c1ccc(F)cc1] | 31 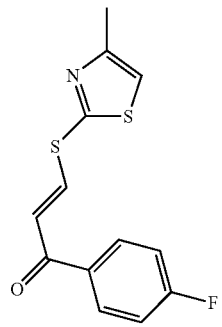 |
| 27 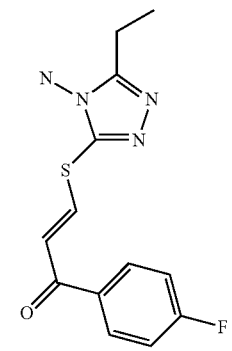 [SMILES: CCc1nnc(S/C=C/C(=O)c2ccc(F)cc2)n1N] | 32 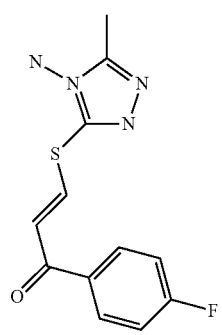 |
| 28 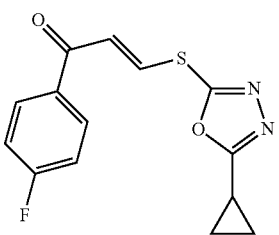 [SMILES: O=C(/C=C/Sc1nnc(C2CC2)o1)c1ccc(F)cc1] | 33 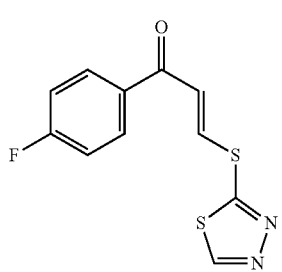 |
| 29 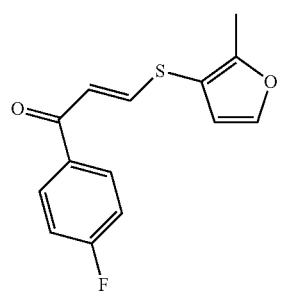 [SMILES: Cc1occc1S/C=C/C(=O)c1ccc(F)cc1] | 34 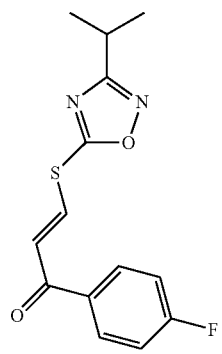 [SMILES: CC(C)c1noc(S/C=C/C(=O)c2ccc(F)cc2)n1] |

TABLE 2-continued
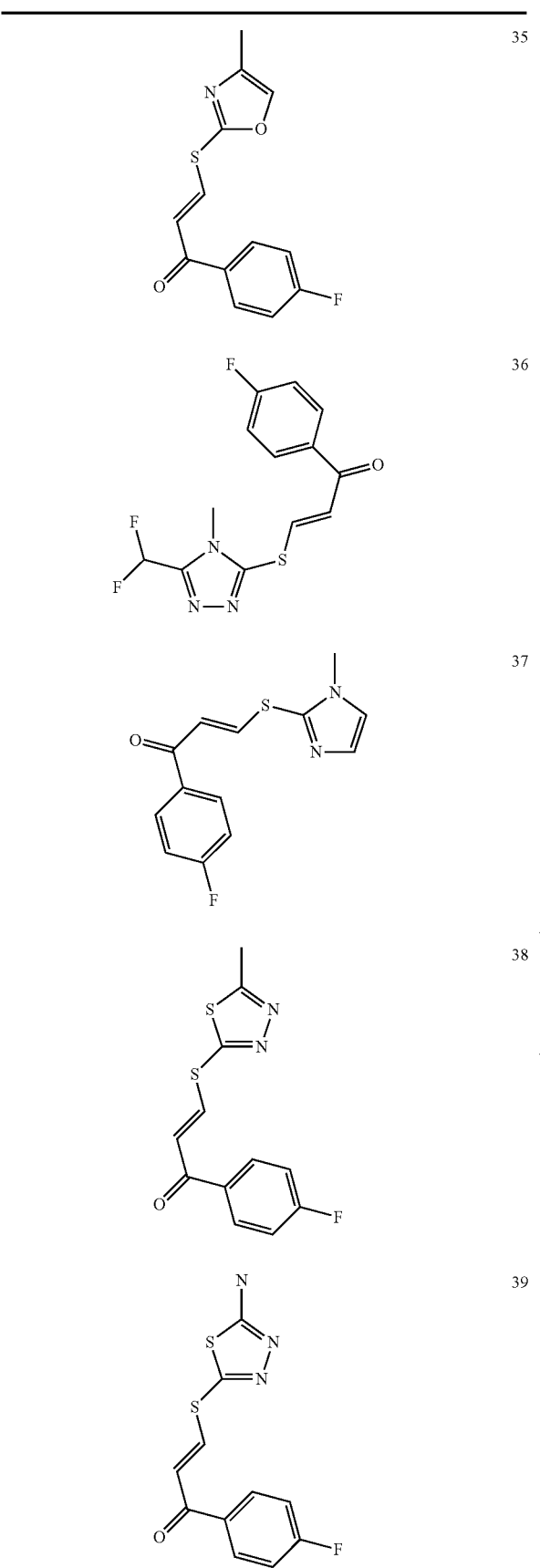
TABLE 2-continued
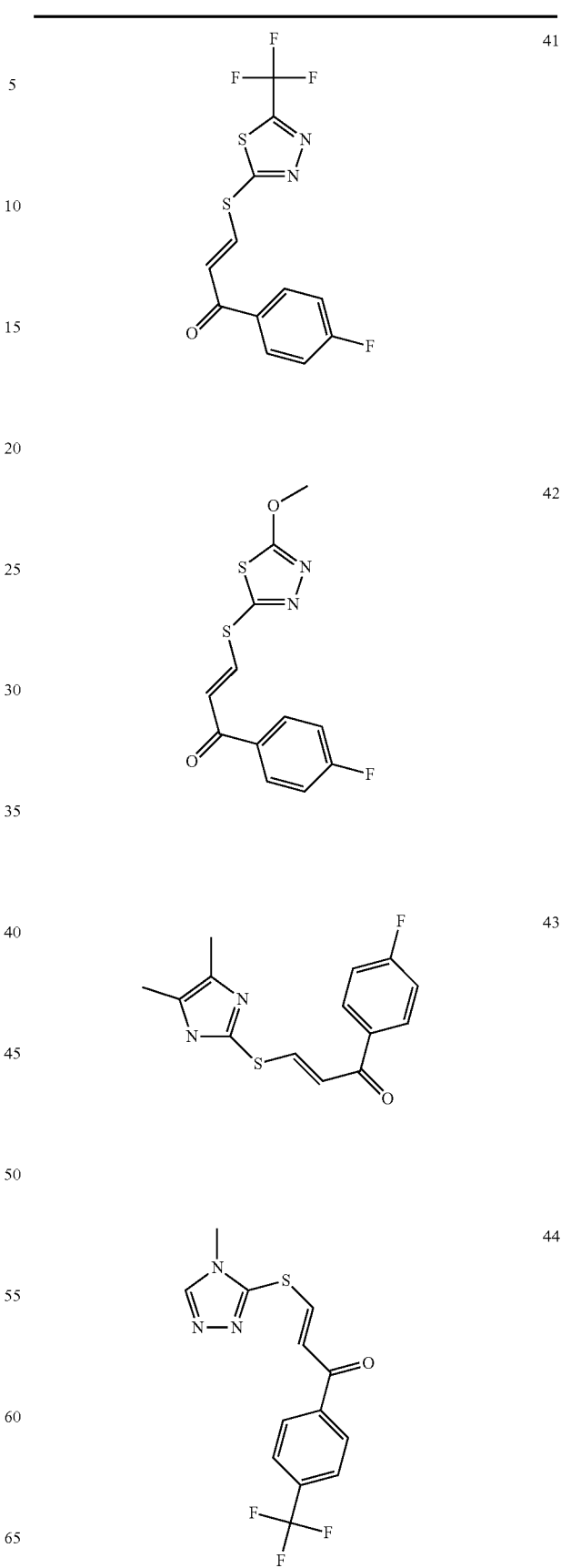

TABLE 2-continued
| 45 | 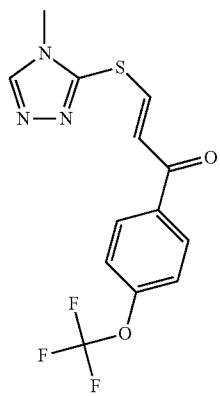 [SMILES: Cn1cnnc1S/C=C/C(=O)c1ccc(OC(F)(F)F)cc1] |
| --- | --- |
| 46 | 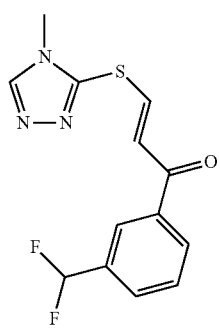 [SMILES: Cn1cnnc1S/C=C/C(=O)c1cccc(C(F)F)c1] |
| 47 | 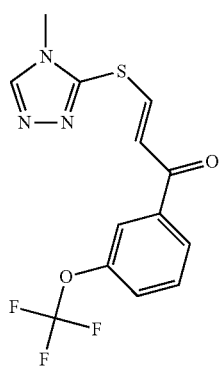 [SMILES: Cn1cnnc1S/C=C/C(=O)c1cccc(OC(F)(F)F)c1] |
| 48 | 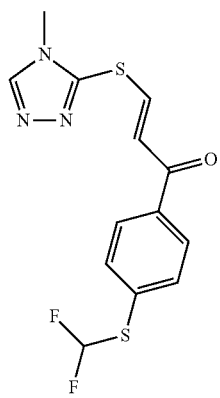 [SMILES: Cn1cnnc1S/C=C/C(=O)c1ccc(SC(F)F)cc1] |
TABLE 2-continued
| 49 | 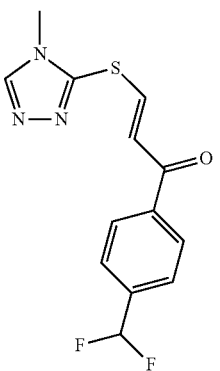 [SMILES: Cn1cnnc1S/C=C/C(=O)c1ccc(C(F)F)cc1] |
| --- | --- |
| 50 | 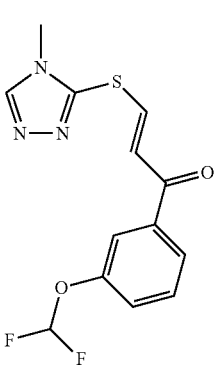 [SMILES: Cn1cnnc1S/C=C/C(=O)c1cccc(OC(F)F)c1] |
| 51 | 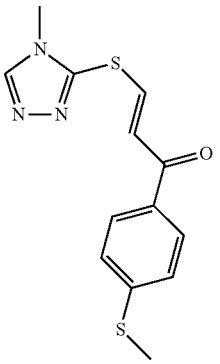 [SMILES: CSc1ccc(C(=O)/C=C/Sc2nncn2C)cc1] |
| 52 | 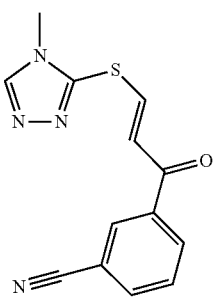 [SMILES: Cn1cnnc1S/C=C/C(=O)c1cccc(C#N)c1] |

TABLE 2-continued
| | |
|---|---|
| 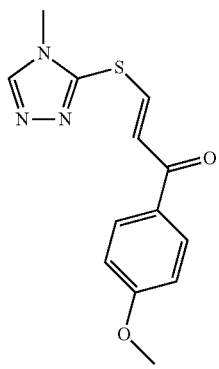 | 53 |
| 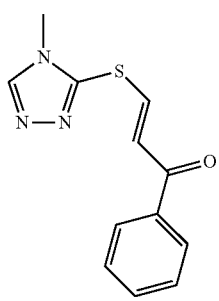 [SMILES: Cn1cnnc1S/C=C/C(=O)c1ccccc1] | 54 |
| 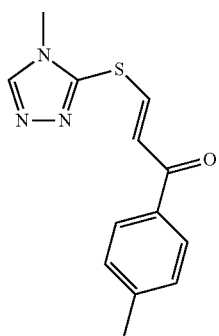 [SMILES: Cc1ccc(C(=O)/C=C/Sc2nncn2C)cc1] (Y102_55) | 55 |
| 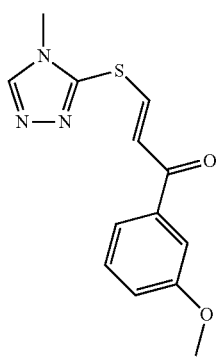 [SMILES: COc1cccc(C(=O)/C=C/Sc2nncn2C)c1] | 56 |
TABLE 2-continued
| | |
|---|---|
| 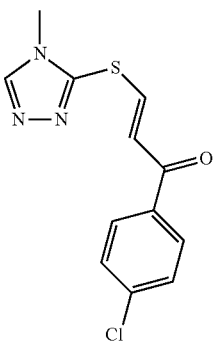 [SMILES: Cn1cnnc1S/C=C/C(=O)c1ccc(Cl)cc1] | 57 |
| 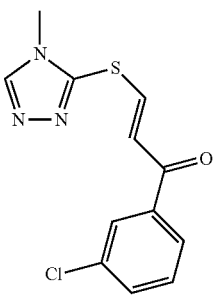 [SMILES: Cn1cnnc1S/C=C/C(=O)c1cccc(Cl)c1] | 58 |
| 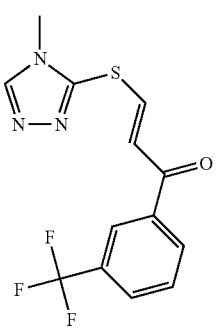 [SMILES: Cn1cnnc1S/C=C/C(=O)c1cccc(C(F)(F)F)c1] | 59 |
| 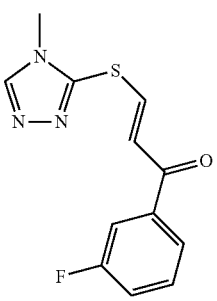 [SMILES: Cn1cnnc1S/C=C/C(=O)c1cccc(F)c1] | 60 |
| 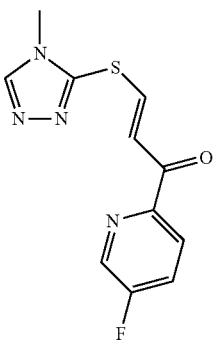 [SMILES: Cn1cnnc1S/C=C/C(=O)c1ccc(F)cn1] | 61 |

TABLE 2-continued
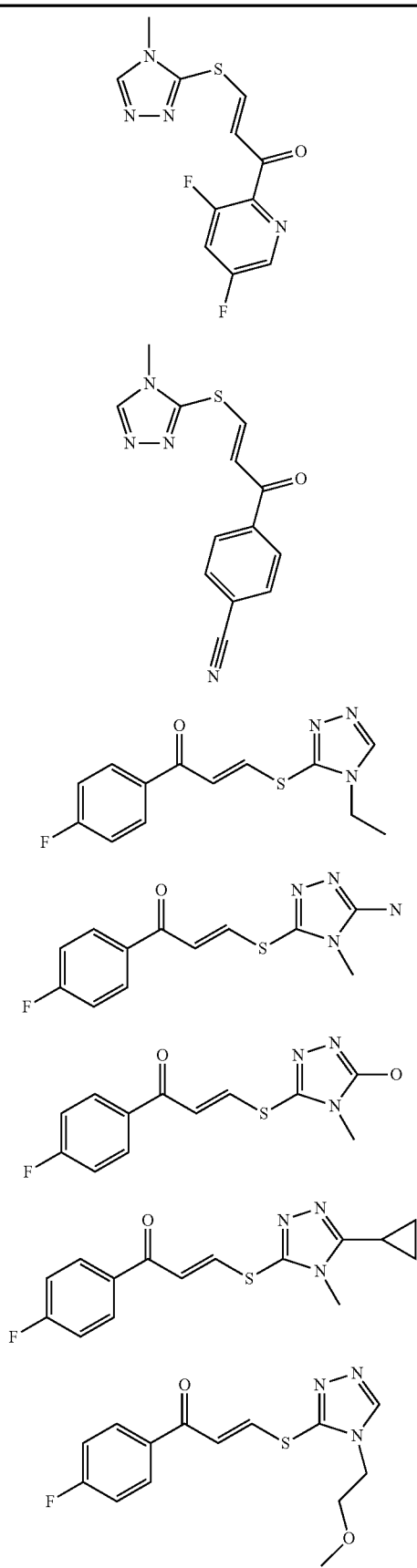
TABLE 2-continued
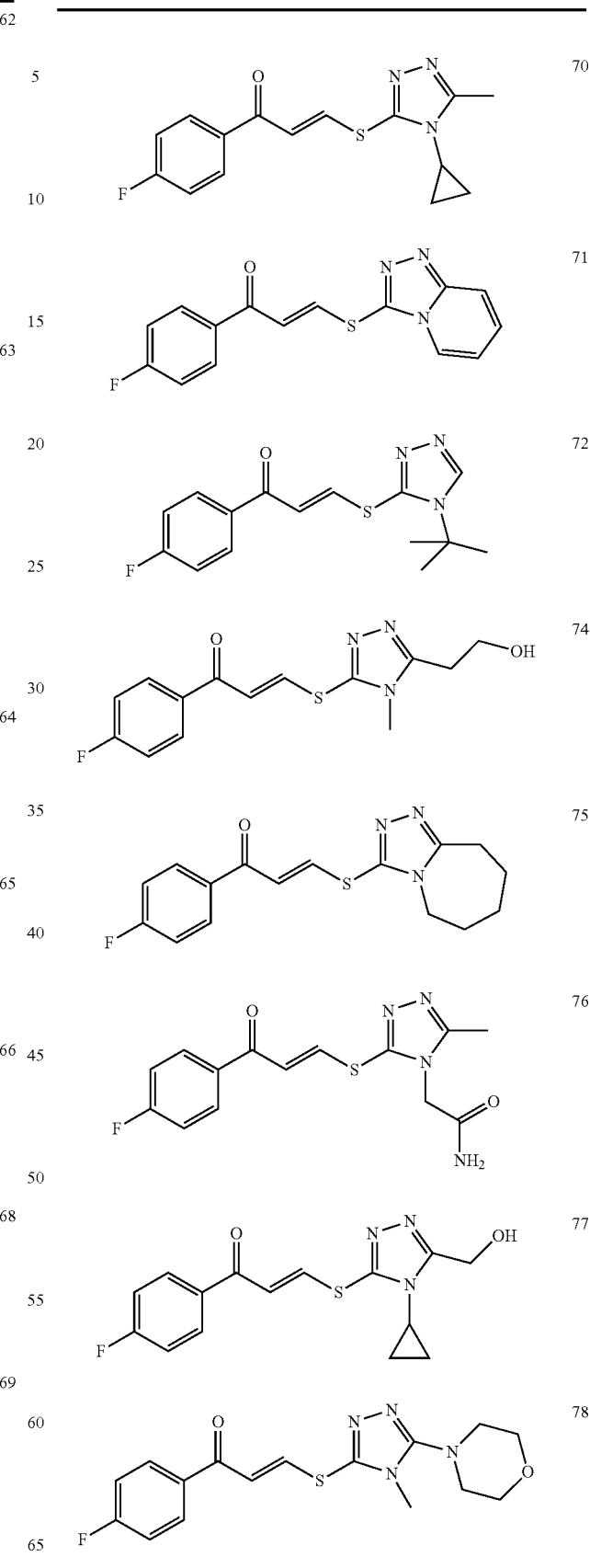

TABLE 2-continued

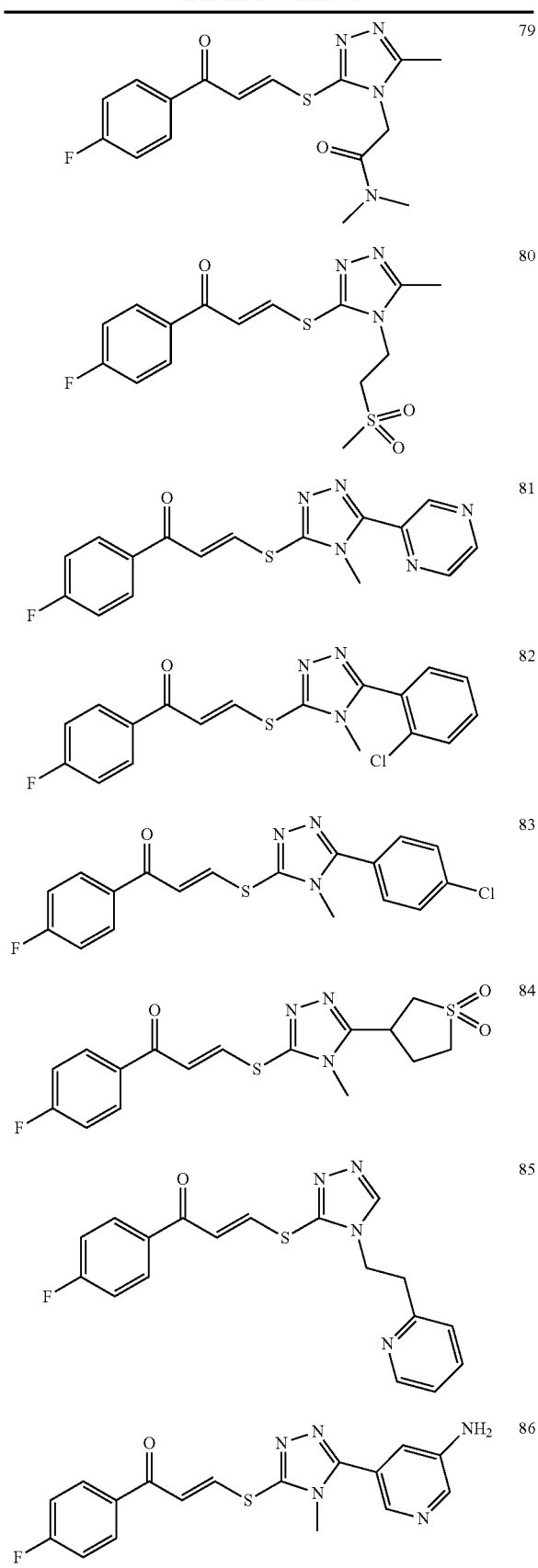
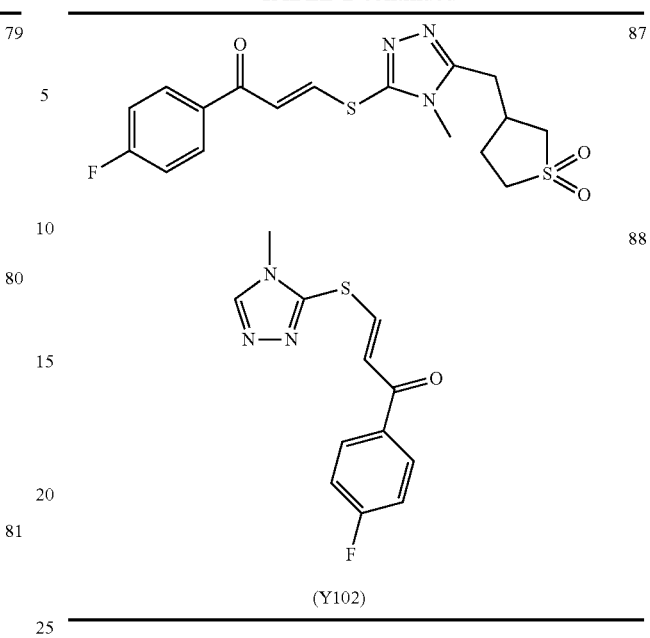

In a particular embodiment, the compound of Formula (I) is selected from the group consisting of compounds 1-36, 38, 39, 41-54 and 58-66, 68-72, 74-87, and pharmaceutically acceptable salts thereof.

Compositions

In another aspect, provided herein is a pharmaceutical composition comprising a compound of the invention (e.g., a compound of Formula (I), (Ia)-(Ig), or Table 2), and a pharmaceutically acceptable carrier. Compounds of the invention are suitable as active agents in compositions that are effective particularly for treating diseases and disorders associated with Ras deregulation or dysregulation, or disease states that disease state that result from a mutation or loss of function in a neurofibromin 1 gene.

The term "pharmaceutical composition" is defined herein to refer to a mixture or solution containing at least one therapeutic agent to be administered to a subject, e.g., a mammal or human, in order to prevent or treat a particular disease or condition affecting the mammal or human.

In various embodiments, pharmaceutical compositions of compounds of the invention comprise a pharmaceutically effective amount of the compound of the invention together with one or more pharmaceutically acceptable excipients, carriers, fillers, diluents and the like.

A "pharmaceutically effective amount" of the compound is that amount necessary or sufficient to treat or prevent a protein kinase-associated disorder, e.g. prevent the various morphological and somatic symptoms of a disorder and/or a disease or condition described herein. In an example, an effective amount of a compound of the invention is the amount sufficient to treat cancer (e.g., breast cancer) in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The pharmaceutical compositions described herein may contain, from about 0.1% to about 99.9%, preferably from about 1% to about 60%, of the therapeutic agent(s). Suitable pharmaceutical compositions for enteral (e.g., oral or rectal) or parenteral (e.g., intravenous or intramuscular) administration are, for example, those in unit dosage forms, such as tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the content of a compound contained in an individual dosage unit need not in itself constitute an effective amount since the necessary effective amount may be reached by administration of a plurality of dosage units.

Methods

In another aspect, provided herein is a method for treating a disorder associated with Ras deregulation or dysregulation comprising administering to a subject in need of treatment an effective amount of a compound of the invention (e.g., a compound according to Formula (I), (Ia)-(Ig) or Table 2) or a pharmaceutically acceptable salt thereof.

In an embodiment, the disorder associated with Ras deregulation or dysregulation comprises a disease state that results from a mutation or loss of function in a neurofibromin 1 gene.

In an embodiment, the disorder associated with Ras deregulation or dysregulation is Neurofibromatosis Type 1.

In an embodiment, the disorder associated with Ras deregulation or dysregulation is neuroblastoma, lung adenocarcinoma, squamous cell carcinoma, glioblastoma, pancreatic cancer, ovarian cancer, colon cancer, lung cancer, neurofibromas, malignant peripheral nerve sheath tumor, optic glioma, Schwannoma, glioma, leukemia, pheochromocytoma or pancreatic adenocarcinoma.

In another aspect, provided herein is a method for inhibiting autophagy in a cell, comprising contacting the cell with a compound of the invention (e.g., a compound according to Formula (I), (Ia)-(Ig) or Table 2) or a pharmaceutically acceptable salt thereof. In an embodiment, the autophagy is mitophagy, i.e., the selective degradation of mitochondria by autophagy.

In another aspect, provided herein is the use of a compound of the invention (e.g., a compound according to Formula (I), (Ia)-(Ig) or Table 2) or a pharmaceutically acceptable salt thereof, in a method for treating a disorder associated with Ras deregulation or dysregulation.

The optimal dosage of a compound of the invention for the treatment of a disease, disorder or condition disclosed herein can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

DEFINITIONS

As used herein, the term "alkyl" refers to a fully saturated branched or unbranched hydrocarbon moiety. Preferably the alkyl comprises 1 to 20 carbon atoms, 1 to 16 carbon atoms, 1 to 10 carbon atoms, or more preferably 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$ alkyl includes, but is not limited to, methyl, ethyl, propyl, butyl, isopropyl, tert-butyl and isobutyl.

As used herein, the term "cycloalkyl" refers to saturated or unsaturated monocyclic, bicyclic or tricyclic hydrocarbon groups of 3-12 carbon atoms, preferably 3-9, or more preferably 3-6 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

"Alkoxy" refers to those alkyl groups, having from 1 to 10 carbon atoms, attached to the remainder of the molecule via an oxygen atom. Alkoxy groups with 1-6 carbon atoms are preferred. The alkyl portion of an alkoxy may be linear, cyclic, or branched, or a combination thereof. Examples of alkoxy groups include methoxy, ethoxy, isopropoxy, butoxy, cyclopentyloxy, and the like. An alkoxy group can also be represented by the following formula: —$OR^i$, where $R^i$ is the "alkyl portion" of an alkoxy group.

As used herein, the term "aryl" refers to aromatic monocyclic or multicyclic, e.g., bicyclic and tricyclic, hydrocarbon ring systems, consisting only of hydrogen and carbon and containing from 6-20 carbon atoms, or 6-10 carbon atoms, particularly 6 carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, imidazolyl, oxazoyl, isoxazoyl, thiazoyl, isothiazolyl, triazoyl, oxadiazoyl, thiadiazoyl, benzothienyl, benzofuranyl, quinolinyl, isoquinolinyl, indolyl, pyrazinyl, pyridazinyl, pyridinyl, pyrimidinyl, pyrrolyl, tetrahydroquinoline, and isomers thereof. "Heteroaryl" is also understood to include the N-oxide derivative of any nitrogen-containing heteroaryl.

The term "heterocycloalkyl" refers to a five-member to ten-member, partially or fully saturated nonaromatic heterocylic group containing at least one heteroatom such as O, S or N. In one embodiment, "heterocycloalkyl" refers to a cyclic group having 4-5 carbon atoms and 1-2 heteroatoms selected from O, S and N in the ring structure. When the heterocycloalkyl group comprises an N atom, the N atom may be oxidized (e.g., N(O)). When the heterocycloalkyl group comprises an S atom, the S atom may be oxidized (e.g., S(O) or S(O)$_2$). Common examples of heterocycloalkyl radicals include piperidinyl, morpholinyl, piperazinyl, and pyrrolidinyl. Attachment of a heterocycloalkyl substituent can occur via a carbon atom or via a heteroatom.

Moreover, the alkyl, alkoxy, cycloalkyl, heterocycloalkyl, aryl and heteroaryl, groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C$ (halogen)$_3$ (e.g., $-CF_3$), $(CR'R'')_{0-3}CH$ (halogen)$_2$, $(CR'R'')_{0-3}CH_2$ (halogen), $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$ (substituted or unsubstituted phenyl), $(CR'R'')_{0-3}$ ($C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (e.g., A, B, C or D), as well as the bond locations of the generic formulae of the invention (e.g., Formulas (I) and (Ia)-(Ig)), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

The terms "treat", "treated", "treating", or "treatment" includes the diminishment or alleviation of at least one symptom associated or caused by the state, disorder or disease being treated. For example, treatment can be diminishment of one or several symptoms of a disorder or complete eradication of a disorder. When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated. In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

The term "use" includes any one or more of the following embodiments of the invention, respectively: the use in the treatment of pain the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise.

The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, inflammation, cardiac hypertrophy, and HIV infection, and other diseases or conditions described herein (e.g., a protein kinase-associated disorder). In another embodiment, the subject is a cell.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" of the compounds of the invention include acid addition salts, which are most suitably formed from pharmaceutically acceptable acids, including for example those formed with inorganic acids (e.g., hydrochloric, hydrobromic, sulphuric or phosphoric acids) and organic acids (e.g., succinic, malaeic, acetic or fumaric acid). Other non-pharmaceutically acceptable salts (e.g., oxalates) can be used for example in the isolation of the compounds of the invention, for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base (e.g., sodium carbonate or potassium hydroxide) to liberate the free base which is then extracted into an appropriate solvent, such as ether. The free base is then separated from the aqueous portion, dried, and treated with the requisite acid to give the desired salt.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Particularly preferred salts are sodium, lysine and arginine salts of the compounds of the invention. Such salts can be formed by procedures well known and described in the art.

Other acids such as oxalic acid, which cannot be considered pharmaceutically acceptable, can be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The invention also embraces isolated compounds. An isolated compound refers to a compound which represents at least 10%, such as at least 20%, such as at least 50% and further such as at least 80% of the compound present in the mixture. In one embodiment, the compound, a pharmaceutically acceptable salt thereof, or a pharmaceutical composition comprising the compound exhibits detectable (i.e. statistically significant) activity when tested in conventional biological assays such as those described herein.

As used herein, "inhibit" means to decrease or counteract an activity or process, such as autophagy.

As used herein, "deregulation" means the act or process of removing restrictions and regulations, such as in cellular signaling.

As used herein, "dysregulation" means the impairment of physiological regulatory mechanisms, such as that governing metabolism.

As used herein and in the appended claims, the singular forms "a", "an" and "the" include plural forms, unless the context clearly dictates otherwise.

Unless defined otherwise or clearly indicated by context, all technical and scientific terms used herein have the same meaning as commonly understood by one of ordinary skill in the art to which this invention belongs.

Pharmaceutical Compositions

In certain embodiments, provided herein are compositions (e.g., pharmaceutical compositions) comprising a therapeutically effective amount of a compound of the invention (e.g., a compound of Formulas (I) and (Ia)-(Ig) or Table 2) and a pharmaceutically acceptable carrier, diluent or excipient. In a particular embodiment, the composition (e.g., pharmaceutical composition) comprises a therapeutically effective amount of a compound selected from compounds 1-36, 38, 39, 41-54 and 58-63, and pharmaceutically acceptable salts thereof.

Pharmaceutical compositions are formulated using one or more physiologically acceptable carriers including excipients and auxiliaries which facilitate processing of the active compounds into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include one or more compounds of the invention and a pharmaceutically acceptable diluent(s), excipient(s), or carrier(s). In addition, the compound of the invention is optionally administered as pharmaceutical compositions in which it is mixed with other active ingredients, as in combination therapy. In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition, as used herein, refers to a mixture of a compound of the invention with other chemical components, such as carriers, stabilizers, diluents, dispersing agents, suspending agents, thickening agents, and/or excipients. The pharmaceutical composition facilitates administration of the compound of the invention to an organism. In practicing the methods of treatment or use provided herein, therapeutically effective amounts of a compound of the invention are administered in a pharmaceutical composition to a mammal having a condition, disease, or disorder to be treated. Preferably, the mammal is a human. A therapeutically effective amount varies depending on the severity and stage of the condition, the age and relative health of an individual, the potency of the compound of the invention used and other factors. The compound of the invention is optionally used singly or in combination with one or more therapeutic agents as components of mixtures.

The pharmaceutical formulations described herein are optionally administered to an individual by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical compositions will include at least one compound of the invention, as an active ingredient in free-acid or free-base form, or in a pharmaceutically acceptable salt form. In some situations, compounds of the invention exist as tautomers. All tautomers are included within the scope of the compounds presented herein.

"Carrier materials" include any commonly used excipients in pharmaceutics and should be selected on the basis of compatibility with compounds disclosed herein, such as, a compound of the invention, and the release profile properties of the desired dosage form. Exemplary carrier materials include, for example: binders, suspending agents, disintegration agents, filling agents, surfactants, solubilizers, stabilizers, lubricants, wetting agents, diluents, and the like.

Moreover, the pharmaceutical compositions described herein, which include a compound of the invention, are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, a formulation comprising a compound of the invention is a solid drug dispersion. A solid dispersion is a dispersion of one or more active ingredients in an inert carrier or matrix at solid state prepared by the melting (or fusion), solvent, or melting-solvent methods. (See Chiou and Riegelman, *Journal of Pharmaceutical Sciences,* 60, 1281 (1971)). The dispersion of one or more active agents in a solid diluent is achieved without mechanical mixing. Solid dispersions are also called solid-state dispersions.

Pharmaceutical preparations for oral use are optionally obtained by mixing one or more solid excipient with a compound of the invention, optionally grinding the resulting mixture, and processing the mixture of granules, after adding suitable auxiliaries, if desired, to obtain tablets. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate.

Formulations that include a compound of the invention suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

In some embodiments, the compound of the invention is administered topically and formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

Compounds of the invention may be usefully combined with another pharmacologically active compound, or with two or more other pharmacologically active compounds, particularly in the treatment of pain. Such combinations offer the possibility of significant advantages, including patient compliance, ease of dosing and synergistic activity.

In one embodiment, provided herein is a pharmaceutical composition comprising a compound the invention, or a pharmaceutically acceptable salt thereof, and a pharmaceutically acceptable carrier, diluent or excipient. In a particular embodiment, the pharmaceutical composition is formulated for intravenous administration. In another particular embodiment, the pharmaceutical composition is formulated for topical administration.

Synthesis

Compounds of the present invention are prepared from commonly available compounds using procedures known to those skilled in the art, including any one or more of the following conditions without limitation:

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by (e.g., medium pressure liquid chromatography over a reversed phase column) and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods (e.g., using chromatographic methods, distribution methods, (re-) crystallization, and the like).

At all stages of the reactions, mixtures of isomers that are formed can be separated into the individual isomers, for example diastereoisomers or enantiomers, or into any desired mixtures of isomers, for example racemates or mixtures of diastereoisomers, analogously to the methods described in Science of Synthesis: Houben-Weyl Methods of Molecular Transformation. Georg Thieme Verlag, Stuttgart, Germany, 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals can, for example, include the solvent used for crystallization. Different crystalline forms may be present.

Materials and Instrumentation

The skilled artisan can make and use the full scope of the invention as described herein using materials and techniques routine in the art and without undue experimentation. Unless otherwise indicated, chemical and biological reagents, solvents and media are used as purchased from commercial vendors. $^1$HNMR spectra were obtained using a Bruker AVANCE DRX 500 Mhz (compound55) and Varian Unity Plus 400 Mhz or Bruker AVANCE III 400 Mhz spectrometer (compound 2). Liquid Chromatography-Mass Spectroscopy (LCMS) data was acquired using an Agilent 1100 Series LC/MSD system with DAD\ELSD and Agilent LC\MSD VL (G1956A), SL (G1956B) mass-spectrometer, and an Agilent 1200 Series LC/MSD system with DAD\ELSD and Agilent LC\MSD SL (G6130A), SL (G6140A) mass-spectrometer, both systems using a Zorbax SB-C18 column (1.8 µm 4.6×15 mm Rapid Resolution cartridge (PN 821975-932)) and a mobile phase of A—acetonitrile, 0.1% formic acid, and B—water (0.1% formic acid).

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications may be made without departing from the spirit of the invention and the scope of the claims.

Example 1—High-Throughput Screen to Identify Target Compounds

Example 1.1—Yeast-Based Screening Platform

A high-throughput screen was used to identify compounds that are synthetically lethal with NF1 loss (14). A synthetic lethal interaction occurs when loss of two genes due to genetic deletion or pharmacologic inhibition is non-lethal independently but is lethal in combination (FIG. 1) (17). The first gene lost is NF1, and the loss of the second gene is mimicked through treatment with the screened compounds. The screen used *Saccharomyces cerevisiae* lacking IRA2 (ira2Δ), a yeast homologue of NF1, as a model for NF1 loss. ira2Δ yeast have increased RAS-GTP, which in turn activates MAPK and PKA pathways that mimic the pathways that are increased in NF1 deficient Schwann cells (18). The yeast in the screen also lacked ERG6 to facilitate drug permeabilization (19).

Example 1.2—High-Throughput Screen to Identify Compounds

Candidate compounds were screened in ira2Δ yeast cells to identify target compounds synthetically lethal to NF1 loss. Growth inhibition of yeast was measured using the optical density of yeast cultures treated with compounds compared to DMSO control (14). A compound was deemed a hit if ira2Δ yeast exhibited slow growth or death at concentrations that had no effect on the growth of control yeast.

Candidate compounds were subsequently tested in NF1 deficient neurological cancer cell lines, such as the glioblastoma cell line U87-MG, which has high proteasomal degradation of NF1, U251-MG, which has inactive NF1 due to a genetic mutation (6), and in the neuroblastoma cell line SK-N-AS, which have low NF1 protein expression (13). Compound Y102 was identified through the high-throughput screen.

Figure 2A:
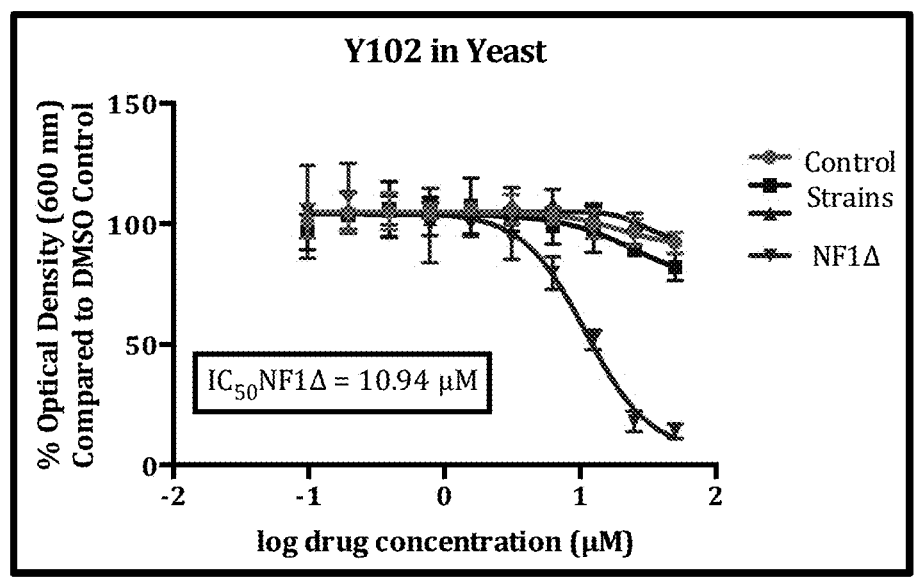
FIGS. 2A-2B show graphs summarizing the results of treating NF1 deficient cells with Y102. NF1 deficient cells are sensitive to Y102. In an isogenic yeast system, NF1 deficient yeast were selectively sensitive to Y102. In U87-MG cells, sensitivity to Y102 was irreversible after 2 hour washout treatment compared to 72 hour treatment.
Figure 2B:
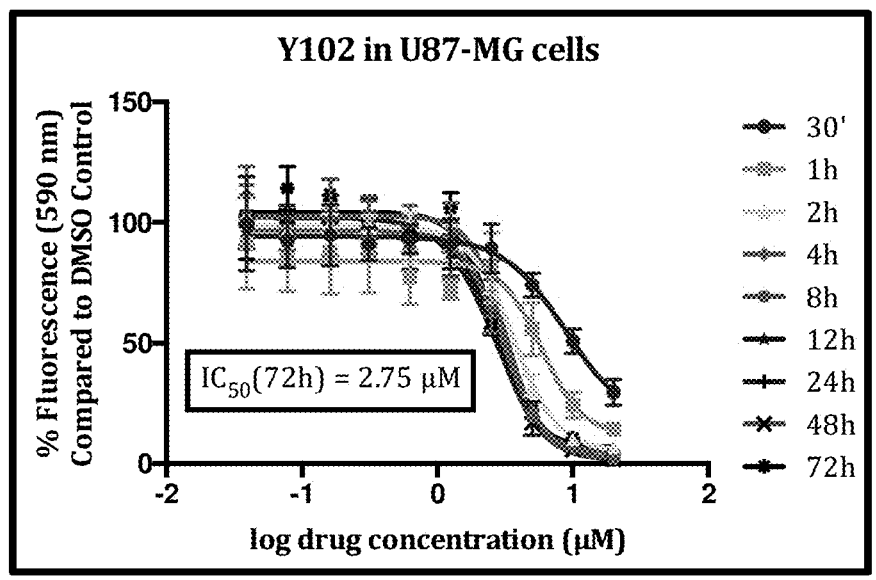
Figure 3:
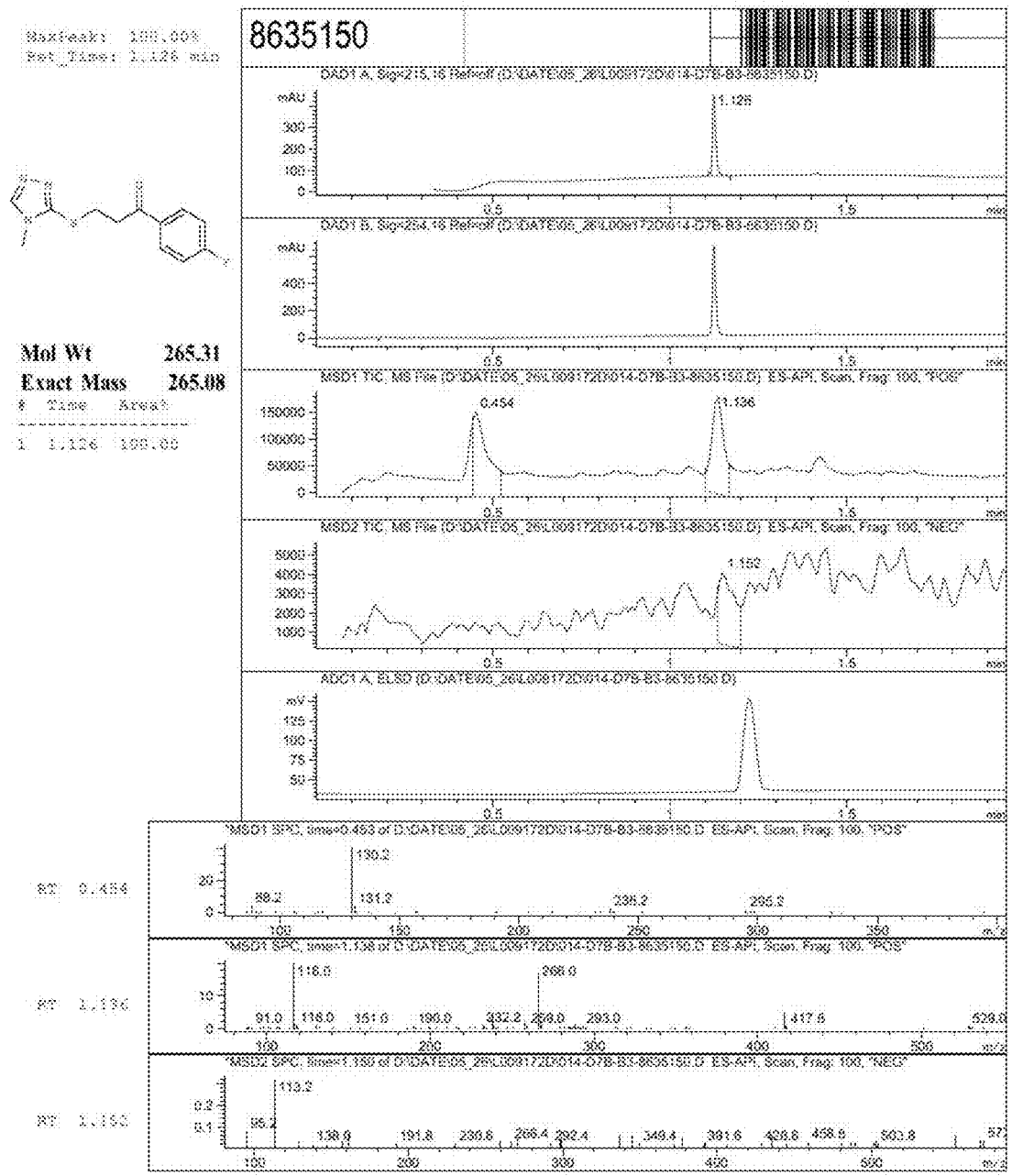
FIG. 3 shows LCMS data for compound JW_1.

Example 2—Y102 Treatment of ira2Δ Yeast Cells and NF1-Deficient Glioblastoma Cells Growth inhibition assays as described above were performed on ira2Δ yeast cells and NF1-deficient glioblastoma cells. Log-phase yeast were grown at 30° C. starting at an OD600 of 0.05 in 96-well plates with Y102 at concentrations ranging from 0 to 100 µM. Following 18 h treatment, OD600 was measured using a THERMOmax (Molecular Devices) microplate reader and SOFTmax Pro 4.3 LS software. Results were plotted as a percentage compared to DMSO control using GraphPad Prism software. Graph represents an average of three experiments with four technical replicates per experiment (FIG. 2A). In a similar experiment U87-MG cells were plated at a concentration of 5,000 cells/well into 96-well plates and allowed to adhere overnight. The following day, cells were treated with Y102 at concentrations ranging from 0 to 20 µM for up to 72 h. For treatments less than 72 h, treatment media was removed at the indicated time points and replaced with normal growth medium. Three hours prior to collection, alamarBlue (Thermo Scientific) was added to a final concentration of 5% v/v. AlamarBlue fluorescence was determined with a Spectramax M2 (Molecular Devices) plate reader at an excitation of 544 nm and an emission of 590 nm using SoftMax Pro 3 software. Results were plotted as a percentage compared to DMSO control using GraphPad Prism software (FIG. 2B). The effect of Y102 treatment on U87-MG cell viability was irreversible as early as two hours after treatment.

Example 3—Y102 Effect on Autophagy: LC3B I/II

Figure 4:
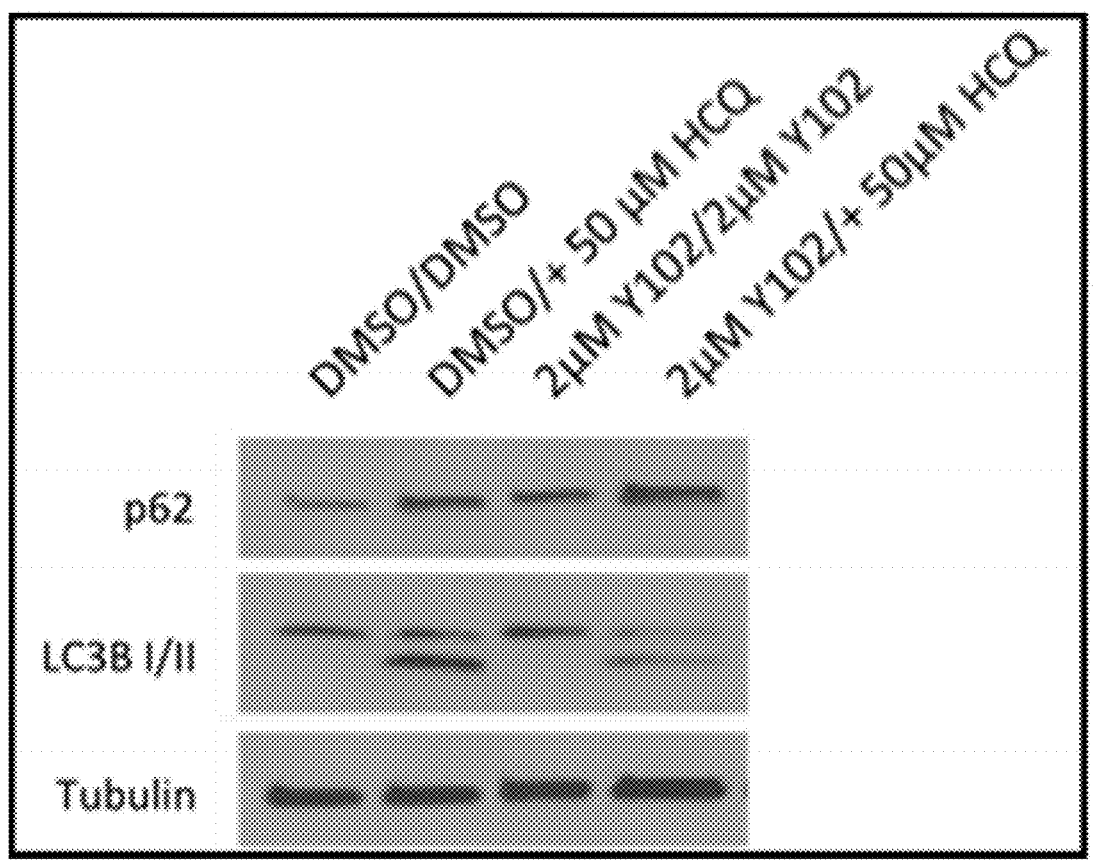
FIG. 4 shows Western blot analysis of p62 and LC3B protein expression in Y102 treated U87-MG cells. Treatment with Y102 for 24 hours resulted in accumulation of the autophagy marker p62, but not LC3B I/II conversion as seen with autophagy inhibitor HCQ. LC3B I/II conversion was seen with 12 hours Y102 treatment followed by 12 hours HCQ.

Ras dysregulated tumors depend on autophagy to remove damaged mitochondria and allow for their survival. LC3B I/II conversion and p62 levels, two markers of autophagy, were examined to investigate whether Y102 treatment had an effect on autophagy in NF1 deficient cells (21). LC3B I is lipidated to form LC3B II following induction of autophagy. LC3B II is recruited and subsequently integrated into the autophagosome. p62 functions as an adaptor protein in autophagy by binding to both ubiquitin-labeled damaged cargo such as protein aggregates or mitochondria and LC3B II to facilitate cargo uptake into the autophagosome. Degradation of the cargo occurs when the autophagosome fuses with the lysosome; when autophagy is inhibited with hydroxychloroquine (HCQ), a drug that prevents acidification of the lysosome, both LC3B II and p62 accumulate as derogation of the autophagosome is prevented, making them valuable markers of autophagic flux. Y102 treatment resulted in accumulation of p62 similarly to that observed with HCQ (FIG. 4). However, upon examination of LC3B I/II conversion via Western immunoblotting, LC3B II was not found to accumulate with Y102 treatment as was observed with HCQ. When treatment with Y102 was followed by HCQ treatment, LC3B II accumulation occurred, but not as robustly as with HCQ alone, suggesting that Y102 may partially inhibit LC3B I/II conversion or that Y102 may modulate a selective form of autophagy.

The data for FIG. 4 was obtained as follows: U87-MG cells were plated in 6-well plates at a concentration of 500,000 cells/well and allowed to adhere overnight. Cells were treated for 12 h with either DMSO or 2 µM Y102, followed by an additional 12 h co-treatment with or without 50 µM HCQ. Following treatment, cells were harvested using 0.25% trypsin, rinsed with PBS, and lysed with 75 µL modified RIPA buffer (50 mM NaCl, 1% v/v nonidet P40, 0.5% w/v sodium deoxycholate, 0.05% w/v sodium dodecyl sulfate, 50 mM Tris pH 8.0) containing 1 mM NaVO4, 1 mM NaF, 1 mM phenylmethylsulfonyl fluoride, 0.1 µg/mL leupeptin, 100 µM benzamidine HCl, 1 µM aprotinin, 0.1 µg/mL soybean trypsin inhibitor, 0.1 µg/mL pepstatin, and 0.1 µg/mL antipain. Protein was quantified using a BCA assay kit (Pierce). 40 µg of protein prepared in 1× Laemmli sample buffer (50 mM Tris pH 6.8, 0.02% w/v bromophenol blue, 2% w/v sodium dodecyl sulfate, 10% v/v glycerol, 1% v/v beta-mercaptoethanol, 12.5 mM EDTA) was separated on a 4-15% polyacrylamide gel using sodium dodecyl sulfate-polyacrylamide gel electrophoresis. Protein was transferred to nitrocellulose membrane, blocked in 5% nonfat milk in TBST, and probed with primary antibodies anti-LC3BI/II (Cell Signaling, 1:1000, overnight at 4° C.), anti-p62/SQSTM-1 D-3 (Santa Cruz, 1:1000, 1 h at room temperature), or anti-α-tubulin B-1-2-5 (Santa Cruz, 1:10000, 1 h at room temperature) in 2% nonfat milk in TBST. Blots were incubated in 1:20,000 anti-rabbit HRP or 1:10,000 anti-mouse HRP secondary antibodies diluted in 2% nonfat milk in TBST for 1 h at room temperature. Film was exposed to standard ECL (Pierce)-coated blots and developed using a standard film processor.

Example 4—Y102 Effect on Autophagy: ROS

Figure 5:
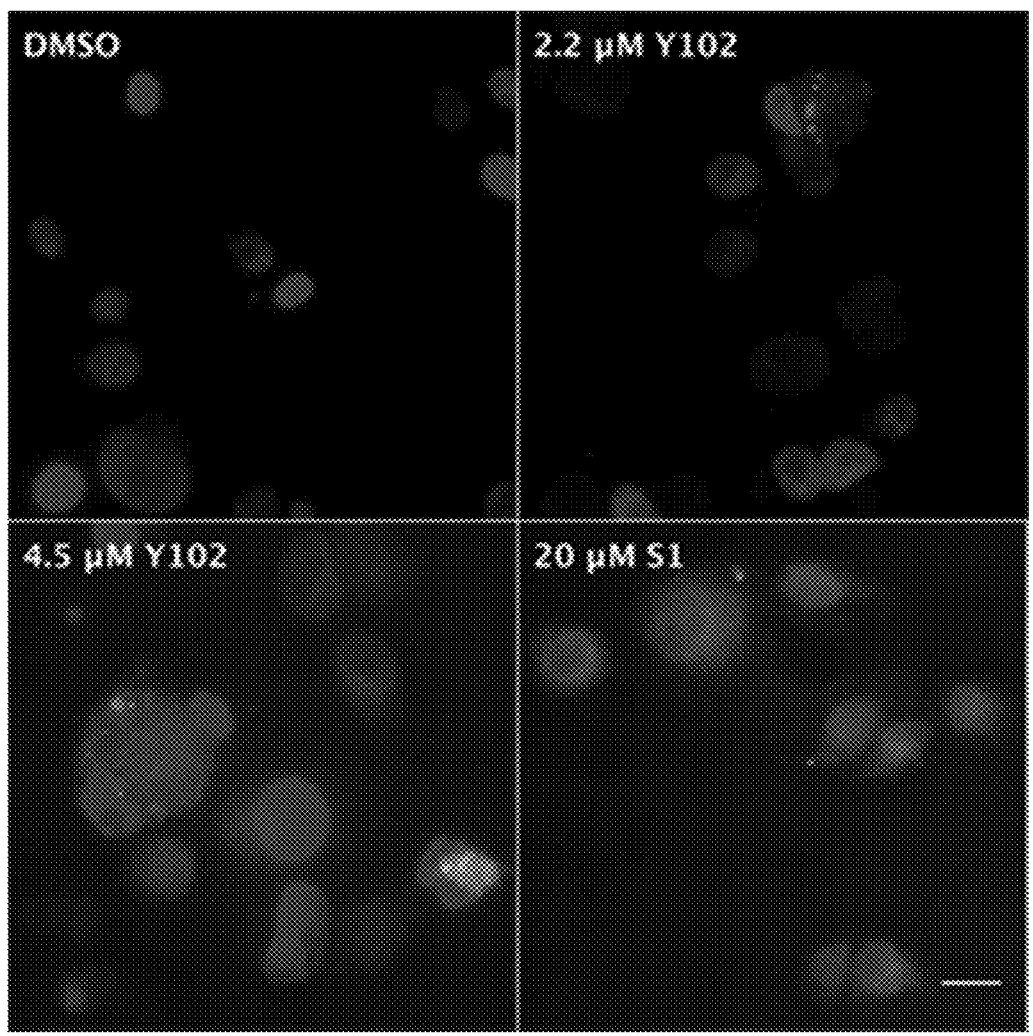
FIG. 5 shows immunofluorescence images of ROS detected by DCF-DA in Y102 treated U87-MG cells. Y102 treatment for 24 hours in U87-MG cells resulted in accumulation of ROS as indicated by DCF-DA. ROS was also induced by S1, but was not observed in the DMSO control.
Figure 6:
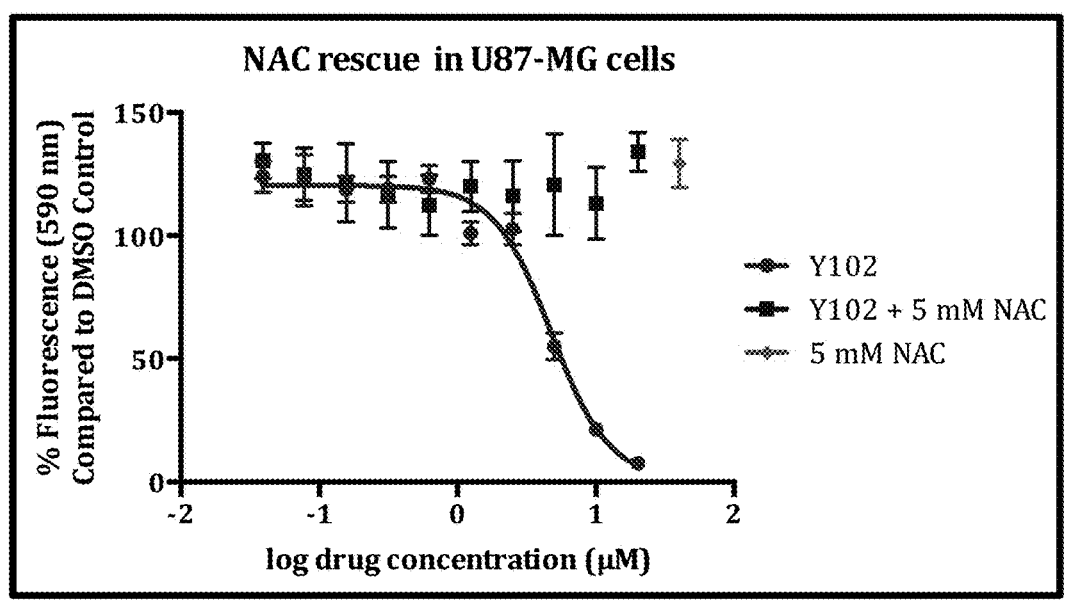
FIG. 6 shows a graph of ROS detected in Y102 treated U87-MG cells exposed to either DMSO or a scavenging agent (N-acetyl cysteine (NAC)). 2 hour pretreatment with NAC rescued NF1 deficient cells from sensitivity to Y102 following 72 hours of Y102 treatment.

Damaged mitochondria generate and accumulate reactive oxygen species (ROS), which are damaging to the cell. RAS dysregulated tumors are reported to depend on autophagy in order to remove the damaged mitochondria and allow for their survival (22). It has also been reported that defective autophagosome formation can result in the accumulation of abnormal mitochondria; therefore, when autophagy is inhibited, you expect to see accumulation of ROS and an altered mitochondrial phenotype (23). The ROS detection reagent DCF-DA, which is converted to its fluorescent form DCF upon ROS-mediated oxidation, was used to examine if ROS levels increase with Y102 treatment. With Y102 treatment, ROS were found to accumulate compared to DMSO treated cells and that treatment with the ROS scavenging agent N-acetyl cysteine (NAC) reversed sensitivity to Y102, suggesting that ROS may play a significant role in Y102-mediated cell death (FIGS. 5 and 6).

The data for FIG. 5 was obtained as follows: U87-MG cells were plated on poly-D-lysine (Neuvitro Corporation) coated coverslips at a concentration of 50,000 cells/well in a 24-well plate and allowed to adhere overnight. Cells were treated for 24 h with DMSO, 2.2 µM Y102, or 4.5 µM Y102, or for 1 h with 20 µM S1. 30 minutes prior to treatment end, cells were stained with 20 µM 2', 7'-dichlorofluorescin diacetate (DCFDA, Sigma, green) at 37° C. Following staining, cells were fixed for 10 minutes with 3.7% formaldehyde. After an additional two washes with PBST, cell nuclei were stained with 0.33 µg/mL DAPI (Molecular Probes) for 30 minutes (blue). Coverslips were mounted on glass slides with ProLong Gold antifade medium. Wide-field images were taken with a Zeiss Imager Z1 wide-field microscope using a 40×1.3 NA EC Plan-NEOFLUAR objective and Zeiss Axiovision software. Scale bar, 20 µm.

The data for FIG. 6 was obtained as follows: U87-MG cells were plated at a concentration of 5,000 cells/well into 96-well plates and allowed to adhere overnight. The following day, cells were pretreated with 5 mM N-acetyl cysteine (NAC) or the equivalent volume of DMSO 2 h prior to treatment with Y102 at concentrations ranging from 0 to 20 µM for 72 h. Three hours prior to collection, alamarBlue (Thermo Scientific) was added to a final concentration of 5% v/v. AlamarBlue fluorescence was determined with a Spectramax M2 (Molecular Devices) plate reader at an excitation of 544 nm and an emission of 590 nm using SoftMax Pro 3 software. Results were plotted as a percentage compared to DMSO control using GraphPad Prism software (FIG. 6).

Example 5—Y102 Effect on Mitophagy: Mitochondrial Membrane Potential (Δψ)

Figure 7:
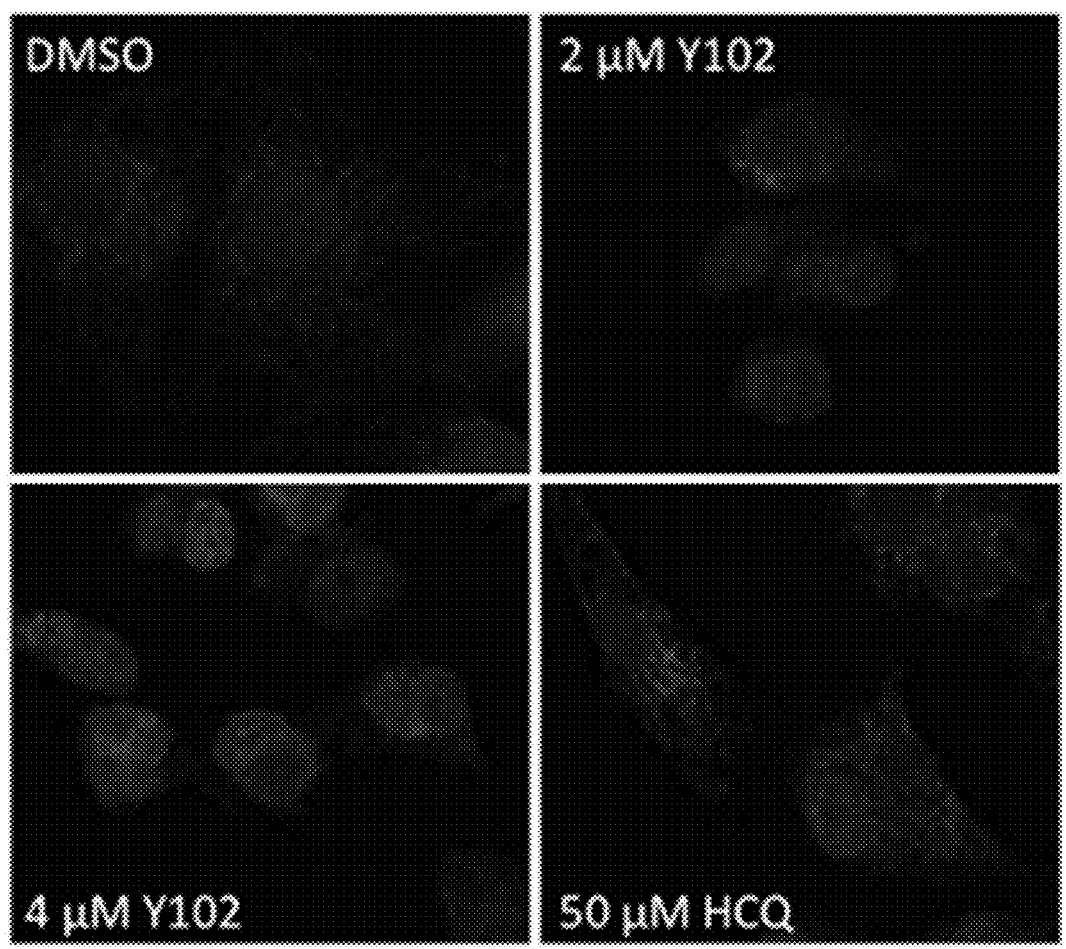
FIG. 7 shows immunofluorescence images of Y102 treated U87-MG cells treated with Mitotracker Red CMXRos. Y102 treatment resulted in perinuclear clustering of the mitochondria in NF1 deficient cells as indicated by Mitotracker Red CMXRos, which stains mitochondria based on their membrane potential. This differed from the autophagy inhibitor HCQ.
Figure 8:
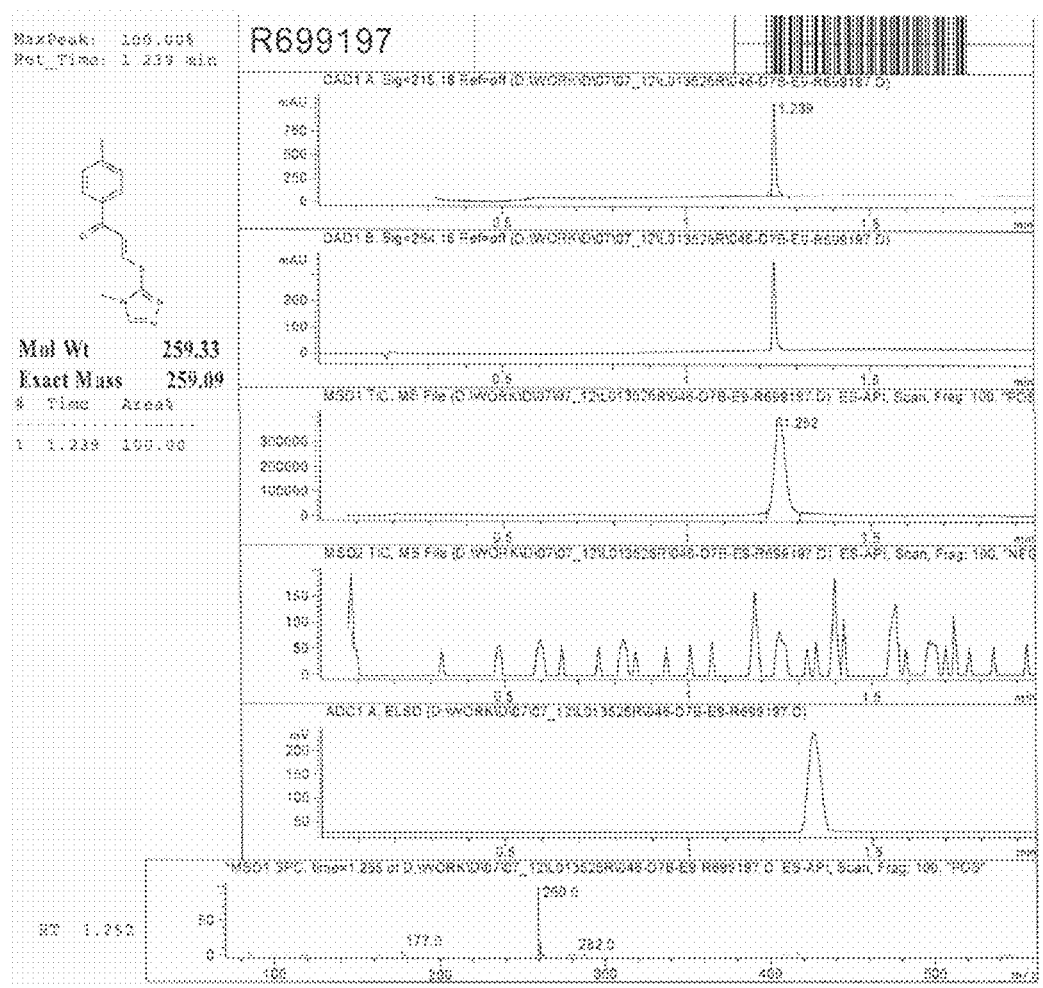
FIG. 8 shows LCMS data for compound 55 (Y102_55).
Figure 9:
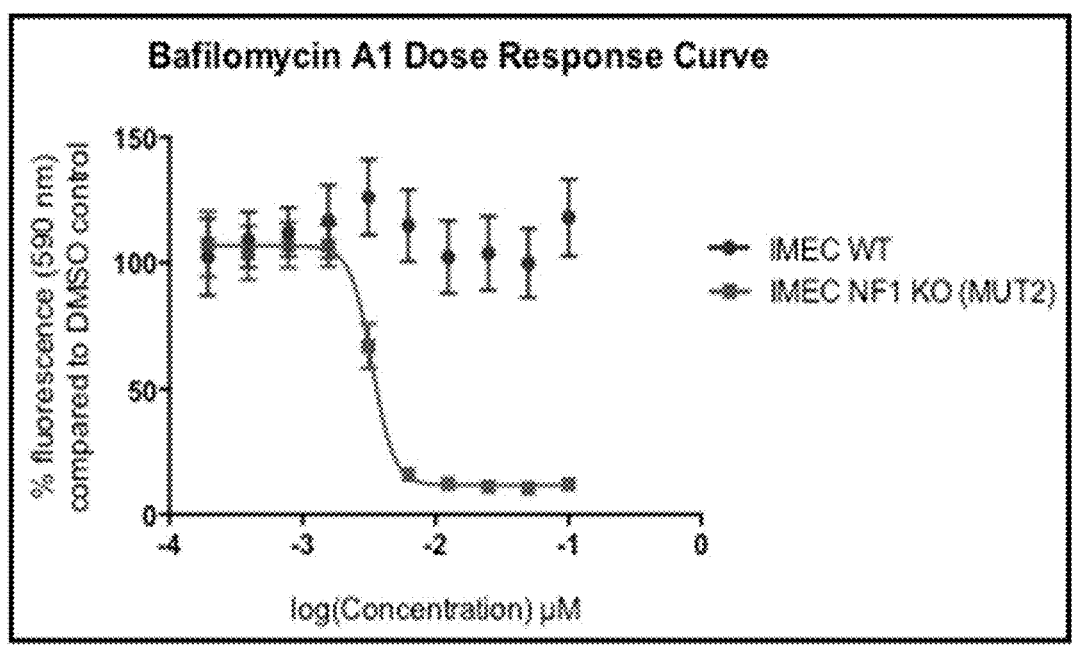
FIG. 9 shows a bafilomycin A1 dose response curve. Bafilomycin A1 was selectively sensitive in NF1 deficient cells compared to NF1 wild type cells. This graph is representative of two replicates.

To examine whether there was a change in the mitochondrial phenotype of cells following Y102 treatment, Mitotracker Red CMXRos, a fluorescent dye whose accumulation is dependent upon membrane permeabilization, was used. With DMSO treatment, U87-MG cells had a fibrillar mitochondrial phenotype; however, treatment with Y1022 resulted in perinuclear accumulation of the mitochondria, which differed from the phenotype observed with HCQ treatment (FIG. 7). There was an increase in mitochondrial fluorescence following Y102 treatment (FIG. 8). This phenotypic change and accumulation observed with the mitochondria suggests that Y102 may be inhibiting the selective removal of mitochondria via autophagy known as mitophagy (24). The data suggest that Y102-mediated cell death occurs due to mitophagy inhibition and ROS accumulation in NF1 deficient cells.

The data for FIG. 7 was obtained as follows: U87-MG cells were plated on poly-L-lysine (Sigma) coated coverslips at a concentration of 50,000 cells/well in a 24-well plate and allowed to adhere overnight. Cells were treated for 24 h with DMSO, 2 µM Y102, 4 µM Y102, or 50 µM HCQ. 30 minutes prior to collection, cells were stained with 100 nM Mitotracker Red CMXRos (Cell Signaling Technology, red) in media at 37° C. Cells were fixed for 10 minutes with 4% methanol-free paraformaldehyde, permeabilized for 15 minutes with 0.5% Triton X-100, blocked with immunofluorescence buffer (2%[v/v] goat serum, 0.2%[v/v] Triton X-100 and 0.05%[w/v] sodium azide in PBS) for 1 h, and stained for 1 h at room temperature for the autophagy marker p62 using anti-p62/SQSTM-1 D-3 (Santa Cruz, 1:500, 1 h at room temperature). Following 3 washes with PBST, cells were stained with goat anti-mouse 488 (Jackson ImmunoResearch Laboratories) secondary antibody for 1 h (green; not shown). After an additional two washes with PBST, cell nuclei were stained with 0.33 µg/mL DAPI (Molecular Probes) for 5 minutes (blue). Coverslips were mounted on glass slides with ProLong Gold antifade medium. Confocal images were taken with a Nikon A1RSi confocal microscope using a 60×1.4 NA objective, a DU4 detector unit, and Nikon Elements software. Image processing was performed with Fiji software (FIG. 7).

The data for FIG. 8 was obtained as follows: U87-MG cells were plated at a concentration of 500,000 cells/well in a 6-well plate and allowed to adhere overnight. Cells were treated for 4 h with DMSO, followed by a 20 h cotreatment with DMSO, 2 µM Y102, 2.75 µM Y102, or 50 µM HCQ. Following treatment, cells were harvested using 0.25% trypsin, rinsed with PBS, and fixed for 20 minutes at 4° C. using BD Cytofix/Cytoperm fixation and permeabilization solution (BD Biosciences). Following 2 washes with BD Perm/Wash buffer (BD Biosciences), cells were stained for 30 minutes at 4° C. in the dark for the mitochondrial marker Tom20 using anti-Tom20 FL-145 (Santa Cruz, 1:200). Following an additional 2 washes with BD Perm/Wash buffer, cells were stained with goat anti-rabbit 488 (Jackson ImmunoResearch Laboratories) secondary antibody for 30 minutes at 4° C. in the dark. Cells were washed twice with BD Perm/Wash buffer, resuspended in 0.5 mL PBS, and filtered prior to analysis. The cells were transferred to flow cytometry tubes and analyzed using a MacsQuant VYB 8-color flow cytometer. Tom20 fluorescence was detected using the B1-A (FITC) channel. 35,000 events/sample were collected and cellular debris was gated out of the dataset. Histograms were generated using the FlowLogic flow cytometry analysis software package.

Example 6—Accumulation of the Mitophagy Marker BNIP3L/Nix

Figure 10:
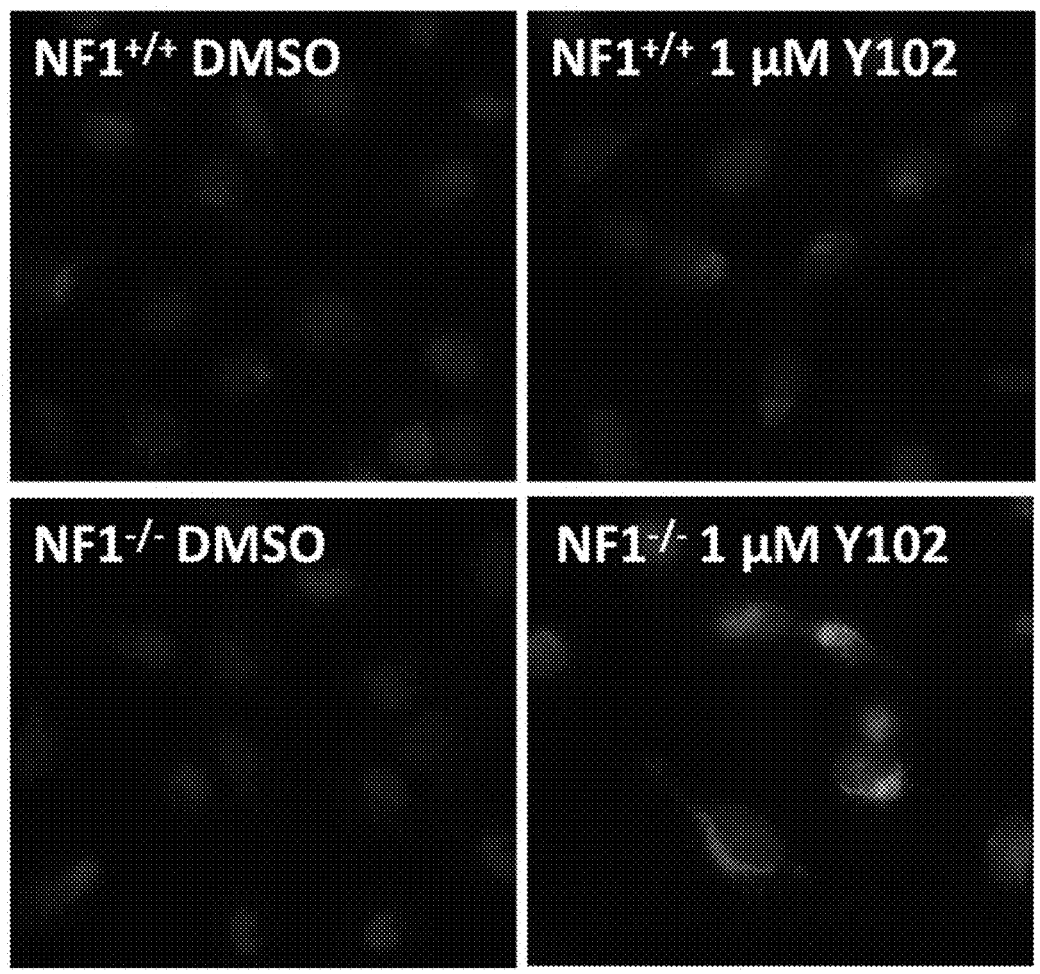
FIG. 10 shows immunofluorescence images of BNIP3L/Nix accumulation in Y102 treated NF1+/+ and NF1−/− IMEC CRISPR cells. The mitophagy receptor BNIP3L/Nix accumulated with Y102 treatment moreso in NF1−/− cells than in NF1+/+ cells compared to DMSO control.

An altered mitochondrial phenotype has been observed following Y102 treatment, and accumulation of the mitochondria following Y102 treatment indicated by the mitochondrial protein Tom20. This suggests that Y102 modulates mitophagy, a selective form of autophagy. Mitochondria can also be removed via non-selective autophagy (21). To distinguish between inhibition of mitophagy and not non-selective autophagy, expression and localization of one mitophagy-specific receptors involved in ubiquitin-dependent mitophagy, BNIP3L/Nix, was examined via immunofluorescence (25) (FIG. 10). BNIP3 and its homologue BNIP3L/NIX are involved in hypoxia-induced mitophagy and are transcriptionally regulated through HIF in human cancers (27). BNIP3-mediated mitophagy is also reported to occur following perinuclear clustering and fragmentation of the mitochondria (28,29). Under hypoxic conditions, both BNIP3 and FUNDC1 are reported to localize to the outer mitochondrial membrane (30). Therefore, if mitophagy is inhibited with Y102 under hypoxic conditions, BNIP3, NIX/BNIP3L, and/or FUNDC1 should accumulate if Y102 inhibits ubiquitin-dependent mitophagy following receptor localization.

CRISPR technology was used to introduce mutated NF1 into mammalian IMEC cells in order to generate an isogenic system for the testing of compounds that mimics the yeast isogenic system used in the original screens. As shown in FIG. 10, perinuclear clustering of the mitophagy receptor BNIP3L/NIX was observed following treatment with Y102 compared to DMSO control, and this accumulation was observed moreso in NF1−/− cells than in NF1+/+ cells.

The data for FIG. 10 was obtained as follows: NF1+/+ and NF1−/− IMEC CRISPR cells were plated on poly-L-lysine (Sigma) coated coverslips at a concentration of 50,000 cells/well in a 24-well plate and allowed to adhere overnight. Cells were treated for 24 h with DMSO or 1 µM Y102. Cells were fixed for 10 minutes with 4% methanol-free paraformaldehyde, permeabilized for 15 minutes with 0.5% Triton X-100, blocked with immunofluorescence buffer (2%[v/v] goat serum, 0.2%[v/v] Triton X-100 and 0.05%[w/v] sodium azide in PBS) for 1 h, and stained overnight at 4° C. for the mitophagy receptor BNIP3L/Nix using anti-BNIP3L/Nix D4R4B (Cell Signaling, 1:200). Following 3 washes with PBST, cells were stained with goat anti-rabbit 488 (Jackson ImmunoResearch Laboratories) secondary antibody for 1 h (green). After an additional two washes with PBST, cell nuclei were stained with 0.33 µg/mL DAPI (Molecular Probes) for 5 minutes (blue). Coverslips were mounted on glass slides with ProLong Gold antifade medium. Wide-field images were taken with a Zeiss Imager Z1 wide-field microscope using a 40×1.3 NA EC Plan-NEOFLUAR objective and Zeiss Axiovision software. See FIG. 10.

Example 7—High Copy Suppressor Screen

A high copy suppressor screen in ira2Δ yeast was performed in order to identify potential targets of Y102. The screen identified 9 suppressor genes that, when overexpressed, allowed for ira2Δ yeast to survive Y102 treatment at concentrations that resulted in the death of ira2Δ yeast expressing an empty vector. These genes (VAM3, RGS2, PDE2, SPG3, PSP1, ZIP2, RME3, PDE1, and BRR6) could encode the target of Y102, or a protein that forms a complex with the target of Y102. These plasmids can have multiple genes on the same plasmid. To investigate whether any of these hits are synthetic lethal with NF1 loss, ira2Δ yeast is crossed with yeast lacking a high copy suppressor hit and the resulting tetrads are dissected to determine whether the double mutant yeast are viable. Few to no double mutant yeast that survive compared to the number of single mutants and wild type yeast indicates that the genes have a synthetic lethal interaction. Gene hits are also overexpressed individually on plasmids, transformed into ira2Δ yeast, and treated with Y102 to identify which high copy suppressor gene from each plasmid is responsible for survival in the presence of Y102.

Example 8—Mammalian Dose Response Assays

Figure 11:
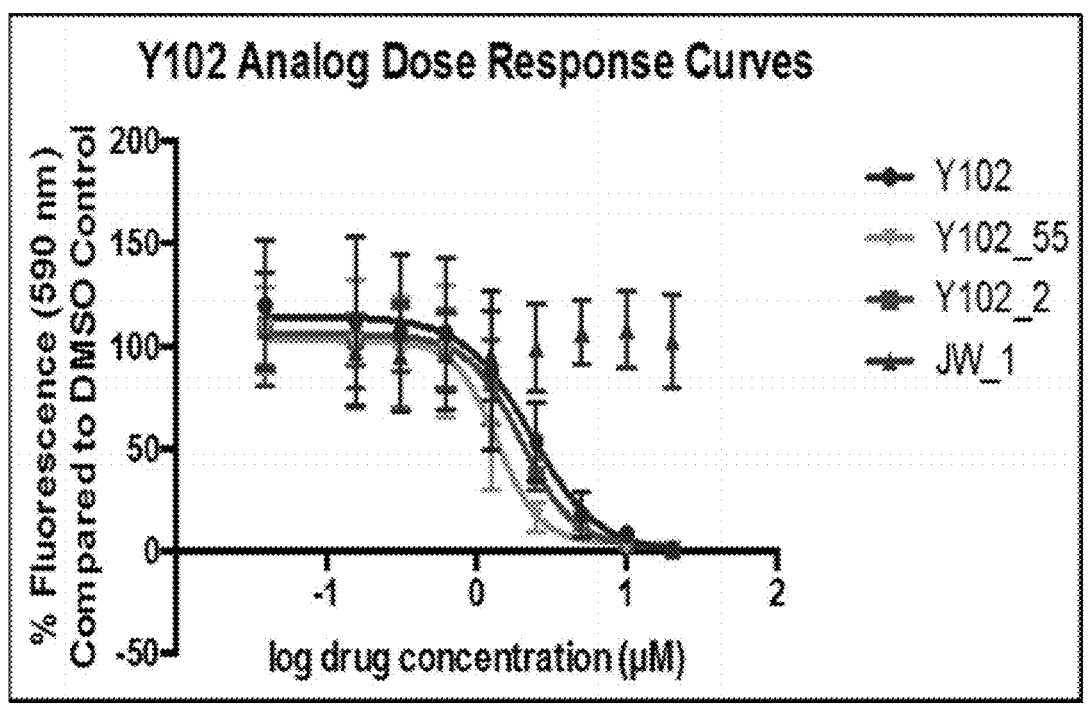
FIG. 11 shows a dose response curve of U87-MG cells treated with analogs of Y102. Compound JW_1 is the α,β-saturated analog of Y102.
Figure 12A:
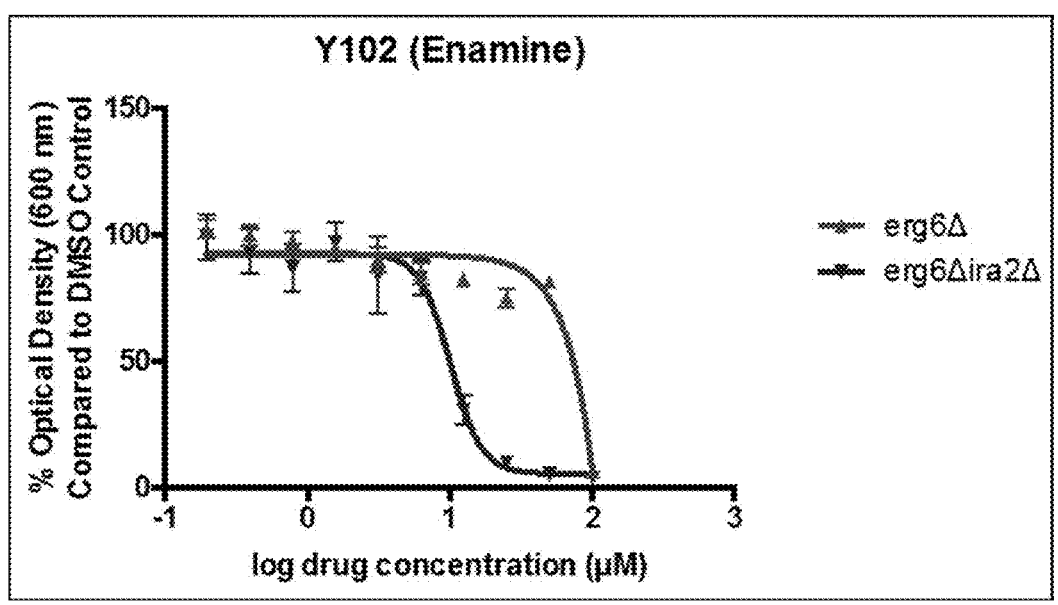
FIGS. 12A-D show yeast dose response assays. Log-phase erg6Δ, and erg6Δira2Δ yeast were grown at 30° C. starting at an OD600 of 0.05 in 96-well plates with Y102 or its analogs Y102_55, Y102_2, or JW_1 at concentrations ranging from 0 to 100 μM. Following 18 h treatment, OD600 was measured using a THERMOmax (Molecular Devices) microplate reader and SOFTmax Pro 4.3 LS software. Results were plotted as a percentage compared to DMSO control using GraphPad Prism software.
Figure 12B:
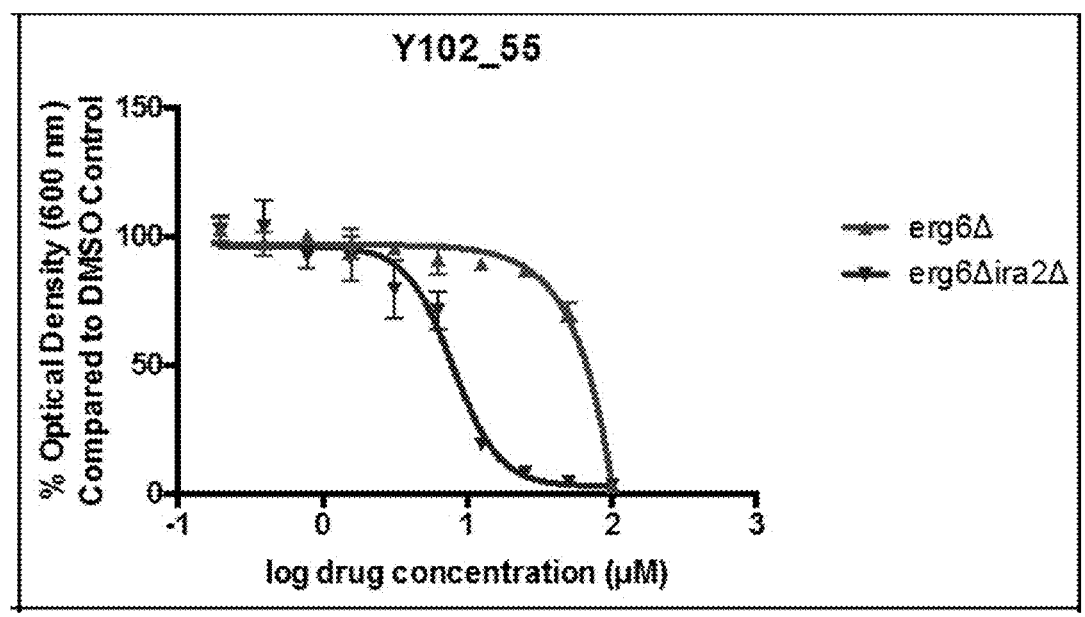
Figure 12C:
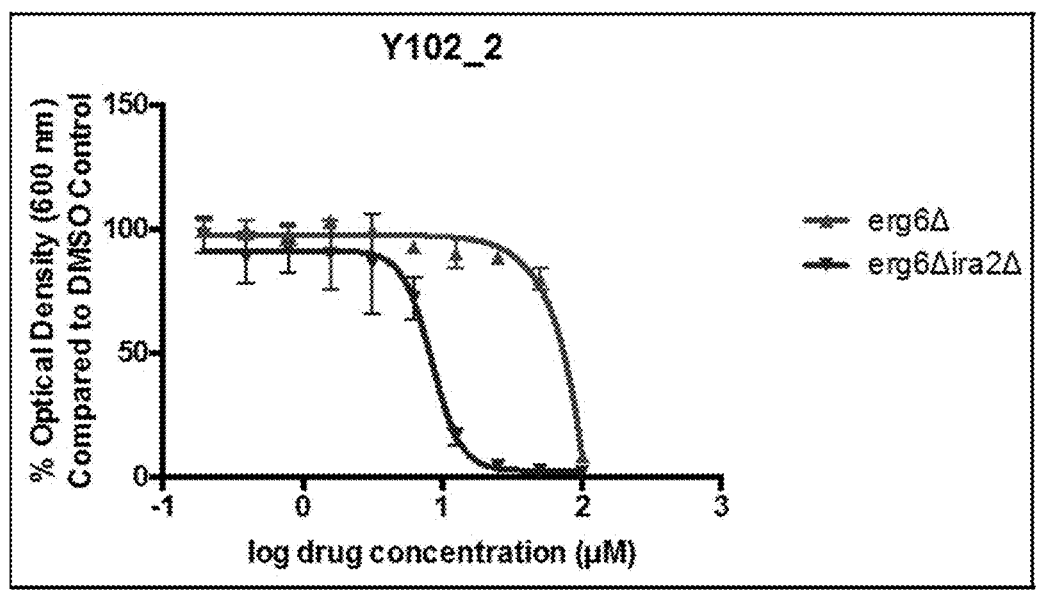
Figure 12D:
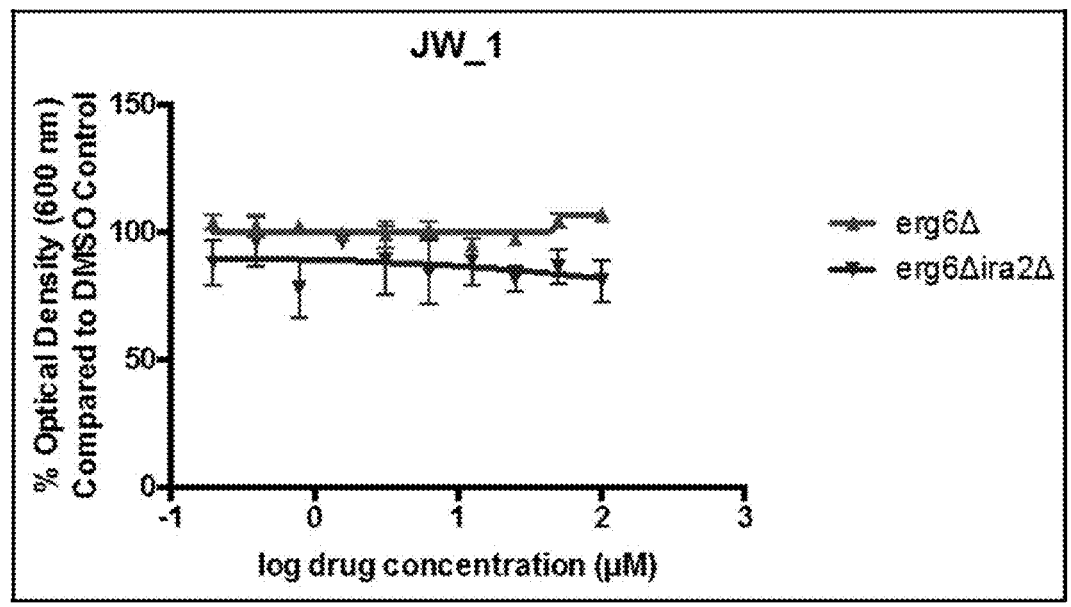

U87-MG cells were plated at a concentration of 5,000 cells/well into 96-well plates and allowed to adhere overnight. The following day, cells were treated with Y102 or its analogs Y102_2, Y102_55, or JW_1 at concentrations ranging from 0 to 20 μM for 72 h. Three hours prior to collection, alamarBlue (Thermo Scientific) was added to a final concentration of 5% v/v. AlamarBlue fluorescence was determined with a Spectramax M2 (Molecular Devices) plate reader at an excitation of 544 nm and an emission of 590 nm using SoftMax Pro 3 software. Results were plotted as a percentage compared to DMSO control using GraphPad Prism software. See FIG. 11.

Example 9—Compound Syntheses

Example 9.1: Synthesis of Compound 88 (Y102)

Example 9.2: Synthesis of Compound 2 (Y1022)

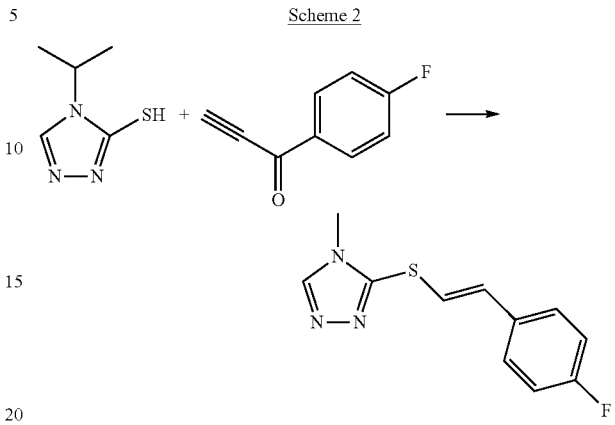

Figure 13A:
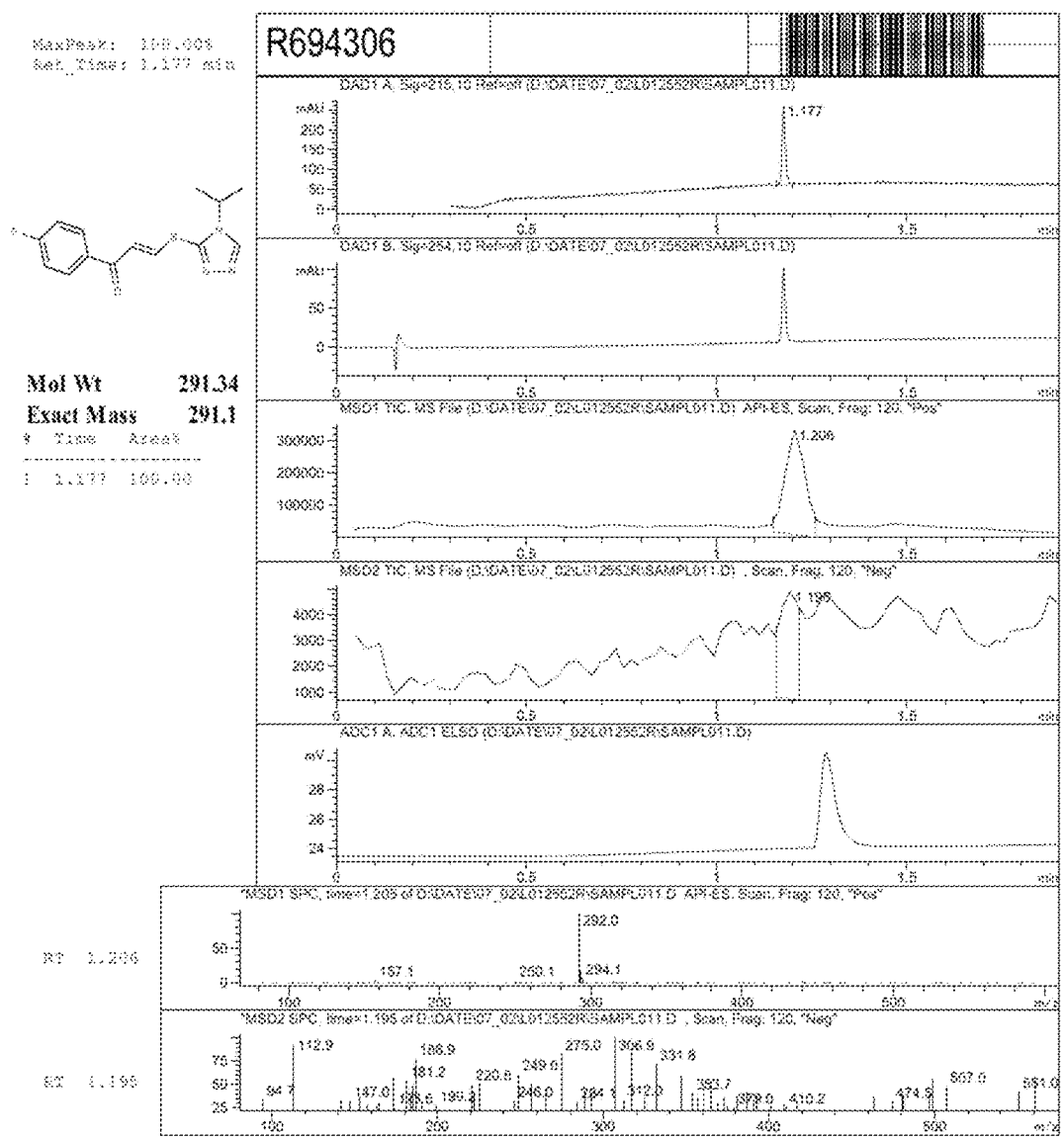
FIG. 13A shows LCMS data for compound 2 (Y102_2).
Figure 13B:
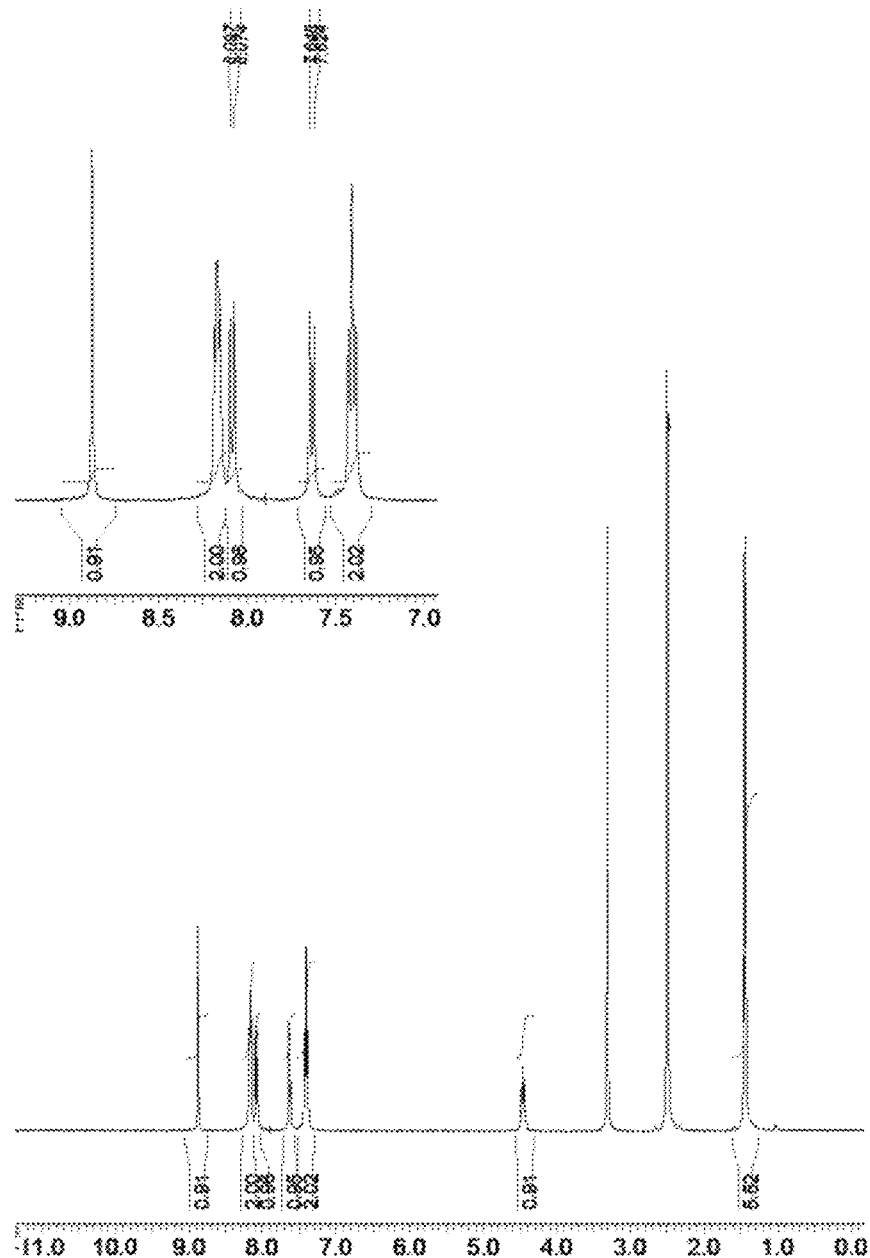
FIG. 13B shows 1HNMR data for compound 2 (Y102_2).

As shown in Scheme 2, 4-isopropyl-4H-1,2,4-triazole-3-thiol was reacted with 1-(4-fluorophenyl)prop-2-yn-1-one to afford compound 2 (Y102_2). Compound 2 was purified by liquid chromatography and positively characterized by LCMS (see FIG. 13).

Example 9.3: Synthesis of Compound 55 (Y10255)

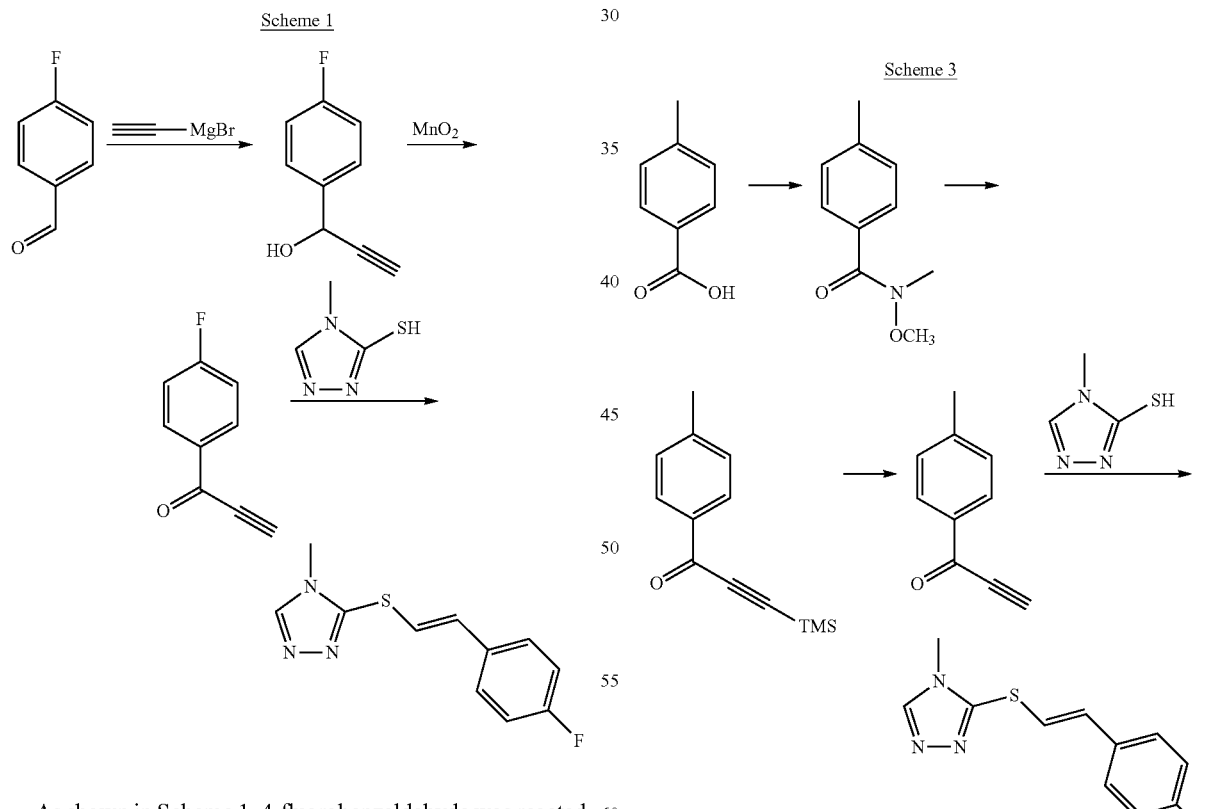

As shown in Scheme 1, 4-fluorobenzaldehyde was reacted with ethynyl magnesium bromide to afford 1-(4-fluorophenyl)prop-2-yn-1-ol. The propargylic alcohol was oxidized with manganese dioxide to obtain 1-(4-fluorophenyl)prop-2-yn-1-one. The propargylic ketone was reacted with 4-methyl-4H-1,2,4-triazole-3-thiol to afford compound 88 (Y102). Compound 88 was purified by liquid chromatography and positively characterized by LCMS.

Figure 14:
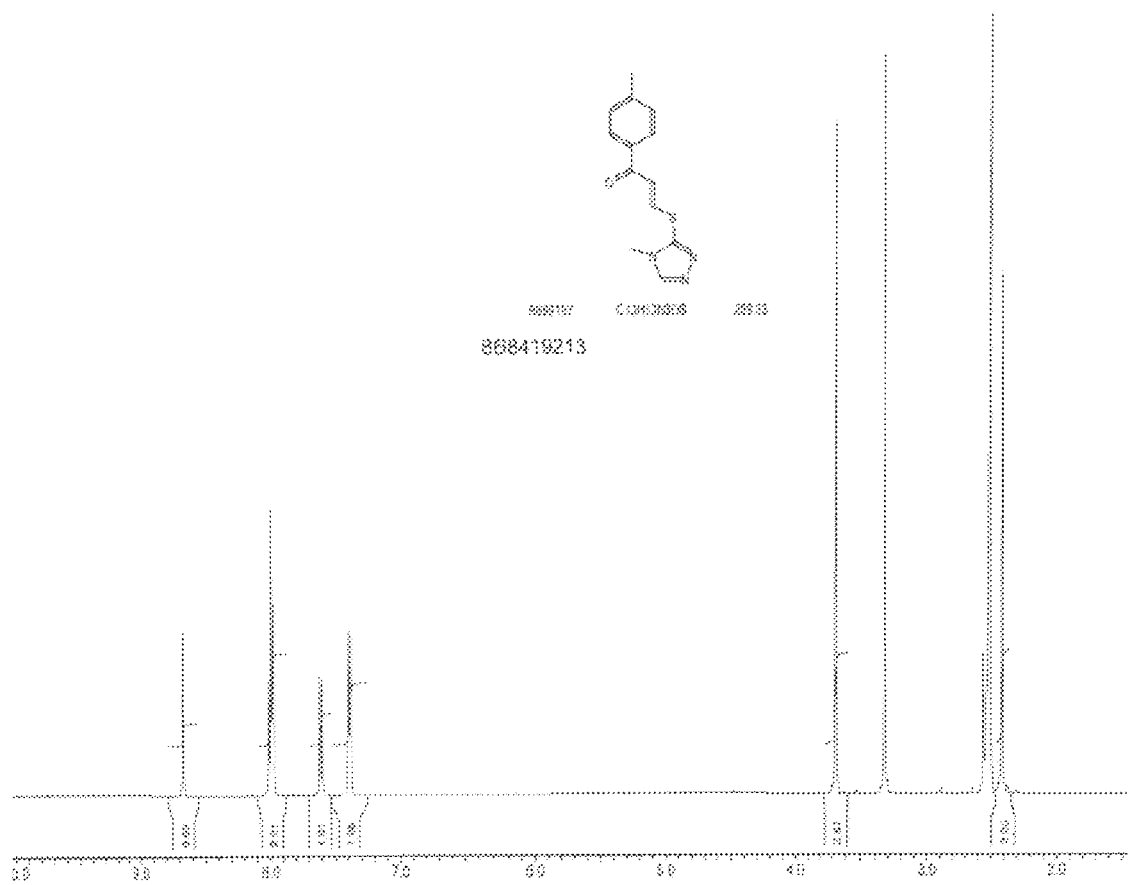
FIG. 14 shows a 1HNMR spectrum of compound 55 (Y102_55).
Figure 15A:
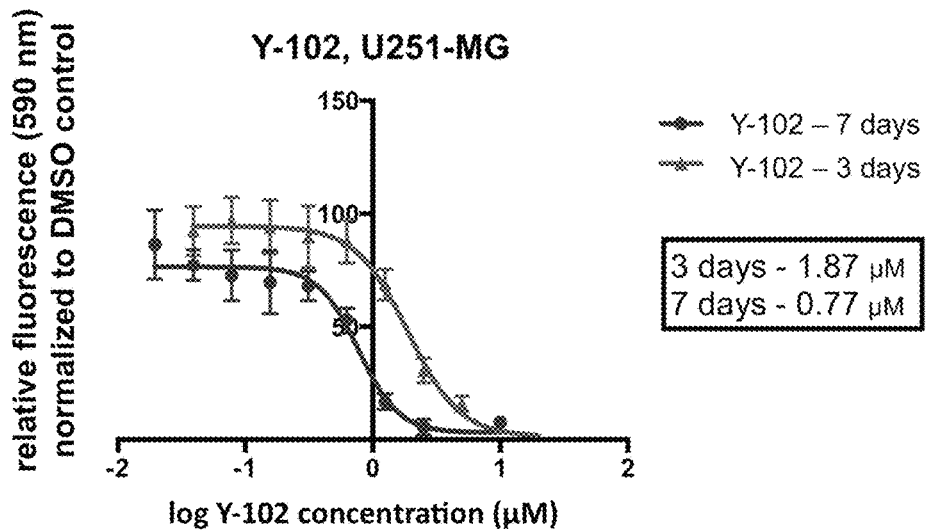
FIGS. 15A-B show that U251-MG and U-87-MG glioblastoma cell lines are sensitive to Y-102. 1000 cells in logarithmic phase were seeded per well (96 well plates) on day zero. The cells were treated for either 3 (red) or 7 (blue) days at a concentration range between 3.9×10-8 M and 2×10-5 M. Growth was assayed by the Alamar Blue method.
Figure 15B:
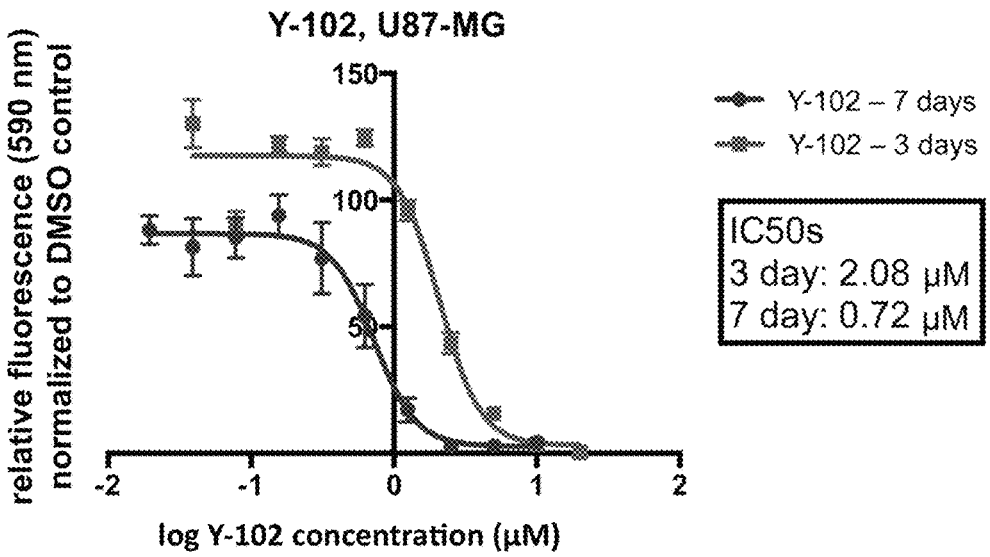

As shown in Scheme 3, 4-methylbenzoic acid was converted to the Weinreb amide, which is reacted with the sodium salt of trimethylsilyl acetylene to yield 1-(p-tolyl)-3-(trimethylsilyl)prop-2-yn-1-one. The trimethylsilyl group was removed by stirring the compound with $K_2CO_3$ in methanol at room temperature to yield 1-(p-tolyl)prop-2-yn-1-one. 1-(p-tolyl)prop-2-yn-1-one was reacted with 4-methyl-4H-1,2,4-triazole-3-thiol to obtain compound 55. Compound 55 was purified by liquid chromatography and positively characterized by 1HNMR (see FIG. 14) and LCMS (see FIG. 8).

Example 9.4: Synthesis of Compounds of Table 2

Compounds of Table 2 are synthesized in analogy to Examples 9.1, 9.2 and 9.3: An aryl or heteroaryl prop-2-yn-1-one is obtained commercially, prepared from the corresponding carboxylic acid (see Example 10.3), or prepared according to Scheme 4 (see below). The prop-2-yn-1-one compound is then reacted with a heterocyclic thiol compound D-SH, wherein D is selected from the fragments of Table 1, to obtain the corresponding compound of Table 2.

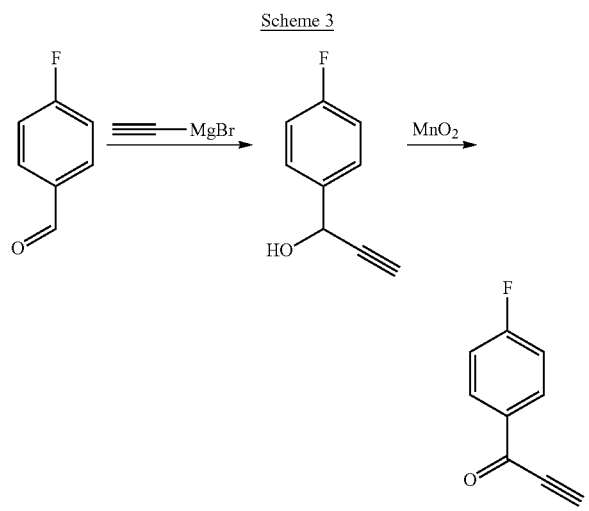

Scheme 3

REFERENCES

1. Korf. Malignancy in Neurofibromatosis Type 1. Oncol. 2000; 5(6):477-485.
2. Keng V, Rahrmann E, Watson A, Tschida B, Moertel C, Jessen W, et al. PTEN and NF1 Inactivation in Schwann Cells Produces a Severe Phenotype in the Peripheral Nervous System That Promotes the Development and Malignant Progression of Peripheral Nerve Sheath Tumors. Cancer Res. 2012; 72(13):3405-3413.
3. Carli M, Ferrari A, Mattke A, Zanetti I, Casanova M, Bisogno G, et al. Pediatric malignant peripheral nerve sheath tumor: the Italian and German soft tissue sarcoma cooperative group. J. Clin. Oncol. 2005 November; 23(33):8422-30.
4. Sordillo P P, Helson L, Hajdu S I, Magill G B, Kosloff C, Golbey R B, et al. Malignant schwannoma—clinical characteristics, survival, and response to therapy. Cancer. 1981 May 5; 47(10):2503-9.
5. DeClue J E, Papageorge A G, Fletcher J A, Diehl S R, Ratner N, Vass W C, et al. Abnormal regulation of mammalian p21 ras contributes to malignant tumor growth in von Recklinghausen (type 1) neurofibromatosis. Cell [Internet]. Elsevier; 1992; 69(2):265-273. Available from: http://www.sciencedirect.com/science/article/pii/0092867492904074.
6. Alcantara Llaguno S R, Wang Z, Sun D, Chen J, Xu J, Kim E, et al. Adult Lineage-Restricted CNS Progenitors Specify Distinct Glioblastoma Subtypes. Cancer Cell. 2015 Oct. 1; 28(4):429-40.
7. McGillicuddy L, Fromm J, Hollstein P, Kubek S, Beroukhim R, Raedt T, et al. Proteasomal and Genetic Inactivation of the NF1 Tumor Suppressor in Gliomagenesis. Cancer Cell. 2009; 16(1):44-54.
8. University of Alabama at Birmingham. A phase 2 trial of the MEK inhibitor PD-0325901 in adolescents and adults with NF1-associated morbid plexiform neurofibromas. [Internet]. 2014. Available from: https://clinicaltrials.gov/ct2/show/NCT02096471.
9. National Cancer Institute. Phase II trial of the MEK 1/2 inhibitor Selumetinib (AZD6244 hydrogen sulfate) in adults with Neurofibromatosis Type 1 (NF1) and plexiform neurofibromas. [Internet]. 2015. Available from: https://clinicaltrials.gov/show/NCT02644512.
10. Oslo University Hospital, Merck Sharp & Dohme Corp. A phase II study of Pembrolizumab in patients with malignant peripheral nerve sheath tumors (MPNST), not eligible for curative surgery. [Internet]. 2016. Available from: https://clinicaltrials.gov/show/NCT02691026.
11. Sarcoma Alliance for Research through Collaboration, Novartis Pharmaceuticals, Genentech Inc., and United States Department of Defense. Phase 2 Study of the mTOR inhibitor Everolimus in combination with Bevacizumab in patients with sporadic and Neurofibromatosis Type 1 (NF1) related refractory malignant peripheral nerve sheath tumors. [Internet]. 2012. Available from: https://clinicaltrials.gov/show/NCT01661283.
12. Sarcoma Alliance for Research through Collaboration, Synta Pharmaceuticals Corp., and United States Department of Defense. A phase I/II trial of Ganetespib in combination with the mTOR inhibitor Sirolimus for patients with recurrent or refractory sarcomas including unresectable or metastatic malignant peripheral nerve sheath tumors. [Internet]. 2013. Available from: https://clinicaltrials.gov/ct2/show/NCT02008877.
13. Hölzel M, Huang S, Koster J, Ora I, Lakeman A, Caron H, et al. NF1 is a tumor suppressor in neuroblastoma that determines retinoic acid response and disease outcome. Cell. 2010 Jul. 5; 142(2):218-29.
14. Wood M, Rawe M, Johansson G, Pang S, Soderquist R S, Patel A V, et al. Discovery of a small molecule targeting IRA2 deletion in budding yeast and neurofibromin loss in malignant peripheral nerve sheath tumor cells. Mol. Cancer Ther. 2011 Sep. 4; 10(9):1740-50.
15. Bourne H, Sanders D, McCormick F. The GTPase superfamily: conserved structure and molecular mechanism. Nature. 1991; 349(6305):117-127.
16. Endo M, Yamamoto H, Setsu N, Kohashi K, Takahashi Y, Ishii T, et al. Prognostic significance of AKT/mTOR and MAPK pathways and antitumor effect of mTOR inhibitor in NF1-related and sporadic malignant peripheral nerve sheath tumors. Clin. Cancer Res. 2013 Jan. 2; 19(2):450-61.
17. Kaelin W G. The concept of synthetic lethality in the context of anticancer therapy. Nat. Rev. Cancer. 2005 Sep. 4; 5(9):689-98.
18. Kim H A, Ratner N, Roberts T M, Stiles C D. Schwann cell proliferative responses to cAMP and Nf1 are mediated by cyclin D1. J. Neurosci. 2001 Feb. 4; 21(4):1110-6.
19. Bjornsti M-A, Osheroff N. DNA Topoisomerase Protocols. Totowa, N.J.: Humana Press; 1999.
20. Kaluz S, Kaluzová M, Stanbridge E. Proteasomal Inhibition Attenuates Transcriptional Activity of Hypoxia- Inducible Factor 1 (HIF-1) via Specific Effect on the HIF-1α C-Terminal Activation Domain. Mol Cell Biol. 2006; 26(15):5895-5907.
21. Glick D, Barth S, Macleod K F. Autophagy: cellular and molecular mechanisms. J. Pathol. 2010 May 6; 221(1):3-12.
22. Guo J, Chen H-Y, Mathew R, Fan J, Strohecker A, Karsli-Uzunbas G, et al. Activated Ras requires autophagy to maintain oxidative metabolism and tumorigenesis. Gene Dev. 2011; 25(5):460-470.
23. Lee J, Giordano S, Zhang J. Autophagy, mitochondria and oxidative stress: cross-talk and redox signalling. Biochem J. 2012; 441(2):523-540.
24. Chourasia A, Boland M, Macleod K. Mitophagy and cancer. Cancer Amp Metabolism. 2015; 3(1):4.
25. Liu L, Sakakibara K, Chen Q, Okamoto K. Receptor-mediated mitophagy in yeast and mammalian systems. Cell Res. 2014; 24(7):787-795.
26. Murakawa T, Yamaguchi O, Hashimoto A, Hikoso S, Takeda T, Oka T, et al. Bcl-2-like protein 13 is a mammalian Atg32 homologue that mediates mitophagy and mitochondrial fragmentation. Nat Commun. 2015; 6:7527.
27. Bellot G, Garcia-Medina R, Gounon P, Chiche J, Roux D, Pouysségur J, et al. Hypoxia-Induced Autophagy Is Mediated through Hypoxia-Inducible Factor Induction of BNIP3 and BNIP3L via Their BH3 Domains. Mol Cell Biol. 2009; 29(10):2570-2581.
28. Tracy K, Dibling B, Spike B, Knabb J, Schumacker P, Macleod K. BNIP3 Is an RB/E2F Target Gene Required for Hypoxia-Induced Autophagy. Mol Cell Biol. 2007; 27(17):6229-6242.
29. Al-Mehdi-B, Pastukh, Swiger, Reed, Patel, Bardwell, et al. Perinuclear Mitochondrial Clustering Creates an Oxidant-Rich Nuclear Domain Required for Hypoxia-Induced Transcription. Sci Signal. 2012; 5(231):ra47-ra47.
30. Hamacher-Brady A, Brady N R. Mitophagy programs: mechanisms and physiological implications of mitochondrial targeting by autophagy. Cell. Mol. Life Sci. 2016 Feb. 1; 73(4):775-95.

The invention claimed is:

1. A method for treating a disorder associated with Ras deregulation or dysregulation comprising administering to a subject in need of treatment an effective amount of a compound having the structure of Formula (I):

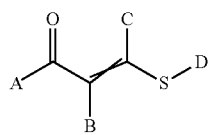

Formula (I)

or a pharmaceutically acceptable salt thereof;
wherein:
A is selected from the group consisting of phenyl, pyridyl, and pyrimidinyl; wherein A is optionally substituted with 1-3 substituents independently selected from the group consisting of halo, cyano, $C_1$-$C_6$ alkyl, $C_3$-$C_6$ cycloalkyl, $C_1$-$C_6$ haloalkyl, $C_1$-$C_6$ alkoxy, and $C_1$-$C_6$ thioalkyl;
B is selected from H, halo and $C_1$-$C_6$ alkyl;
C is selected from H, halo and $C_1$-$C_6$ alkyl;
D is a heteroaryl moiety;
wherein D is optionally substituted with 1-3 substituents independently selected from the group consisting of halo, hydroxy, cyano, $C_1$-$C_6$ alkyl, $C_1$-$C_6$ alkyl-C(O)NH$_2$, $C_1$-$C_6$ alkyl-C(O)N($C_1$-$C_6$ alkyl)$_2$, $C_1$-$C_6$ alkyl-S(O)$_x$($C_1$-$C_6$ alkyl), $C_1$-$C_6$ alkyl-$C_3$-$C_6$ heterocycloalkyl, $C_1$-$C_6$ alkyl-heteroaryl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ alkoxy-$C_1$-$C_6$ alkyl, $C_1$-$C_6$ thioalkyl, aryl and heteroaryl;
wherein x is 0, 1 or 2; and
⫽ represents a double bond having E or Z stereochemistry.

2. The method of claim 1, wherein said disorder associated with Ras deregulation or dysregulation comprises a disease state that results from a mutation or loss of function in a neurofibromin 1 gene.

3. The method of claim 1, wherein said disorder associated with Ras deregulation or dysregulation is Neurofibromatosis Type 1.

4. The method according to claim 1, wherein said disorder associated with Ras deregulation or dysregulation is neuroblastoma, lung adenocarcinoma, squamous cell carcinoma, glioblastoma, pancreatic cancer, ovarian cancer, colon cancer, lung cancer, neurofibromas, malignant peripheral nerve sheath tumor, optic glioma, Schwannoma, glioma, leukemia, pheochromocytoma or pancreatic adenocarcinoma.

5. A method for inhibiting autophagy in a cell, comprising contacting the cell with a compound having the structure of Formula (I):

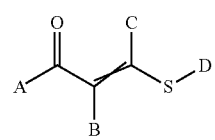

Formula (I)

or a pharmaceutically acceptable salt thereof;
wherein:
A is selected from the group consisting of phenyl, pyridyl, and pyrimidinyl; wherein A is optionally substituted with 1-3 substituents independently selected from the group consisting of halo, cyano, $C_1$-$C_6$ alkyl, $C_3$-$C_6$ cycloalkyl, $C_1$-$C_6$ haloalkyl, $C_1$-$C_6$ alkoxy, and $C_1$-$C_6$ thioalkyl;
B is selected from H, halo and $C_1$-$C_6$ alkyl;
C is selected from H, halo and $C_1$-$C_6$ alkyl;
D is a heteroaryl moiety;
wherein D is optionally substituted with 1-3 substituents independently selected from the group consisting of halo, hydroxy, cyano, $C_1$-$C_6$ alkyl, $C_1$-$C_6$ alkyl-C(O)NH$_2$, $C_1$-$C_6$ alkyl-C(O)N($C_1$-$C_6$ alkyl)$_2$, $C_1$-$C_6$ alkyl-S(O)$_x$($C_1$-$C_6$ alkyl), $C_1$-$C_6$ alkyl-$C_3$-$C_6$ heterocycloalkyl, $C_1$-$C_6$ alkyl-heteroaryl, $C_3$-$C_6$ cycloalkyl, $C_3$-$C_6$ heterocycloalkyl, $C_1$-$C_6$ haloalkyl, $C_1$-$C_6$ alkoxy, $C_1$-$C_6$ alkoxy-$C_1$-$C_6$ alkyl, $C_1$-$C_6$ thioalkyl, aryl and heteroaryl;
wherein x is 0, 1 or 2; and
⫽ represents a double bond having E or Z stereochemistry.

6. The method of claim 1, wherein B and C are both H.

7. The method of claim 1, wherein ⫽ represents a double bond having E stereochemistry.

8. The method of claim 1, wherein A is unsubstituted or is substituted with 1-3 substituents selected from the group consisting of —Cl, —F, —CN, —CH$_3$, —CHF$_2$, —CF$_3$, —OCH$_3$, —SCH$_3$, —OCHF$_2$, —OCF$_3$, —SCHF$_2$, and —SCF$_3$.

9. The method of claim 1, wherein A is phenyl.

10. The method of claim 1, provided that:
i. when A is unsubstituted phenyl, D is not 3-methylthio-1,2,4-thiadiazol-5-yl, 1-methyl-tetrazol-5-yl, 1-phenyl-tetrazol-5-yl, 4-cyano-5-methyl-isothiazol-3-yl, or 4-phenyl-thiazol-2-yl, and D does not comprise a moiety selected from the group consisting of 1,2,4-triazolyl, pyridinyl, pyrimidinyl, benzimidazol-2-yl, benzoxazol-2-yl, benzothiazol-2-yl and purinyl;
ii. when A is 4-fluorophenyl, D is not 1-methylimidazol-2-yl, 1-phenyl-tetrazol-5-yl, 4-phenyl-thiazol-2-yl, or 4-methyl-1,2,4-triazol-3-yl, and D does not comprise a moiety selected from pyridinyl, pyrimidinyl, benzimidazol-2-yl, benzoxazol-2-yl, benzothiazol-2-yl; and
iii. when A is 4-chlorophenyl, D is not 1H-1,2,4-triazol-5-yl, 1-methylimidazol-2-yl, 1-methyl-tetrazol-5-yl, 1-phenyl-tetrazol-5-yl, 3-methylthio-1,2,4-thiadiazol-5-yl, 4-phenyl-thiazol-2-yl, and D does not comprise a moiety selected from pyridinyl, pyrimidinyl, benzimidazol-2-yl, benzoxazol-2-yl, benzothiazol-2-yl.

11. The method of claim 1, wherein the compound of Formula (I) has the structure of Formula (Ia), or a pharmaceutically acceptable salt thereof:

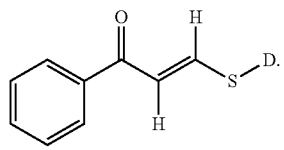

Formula (Ia)

12. The method of claim 1, wherein the compound of Formula (I) has the structure of Formula (Ib), or a pharmaceutically acceptable salt thereof:

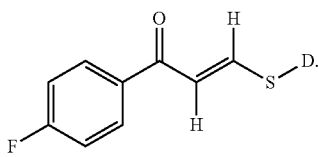

Formula (Ib)

13. The method of claim 1, wherein the compound of Formula (I) has the structure of Formula (Ic), or a pharmaceutically acceptable salt thereof:

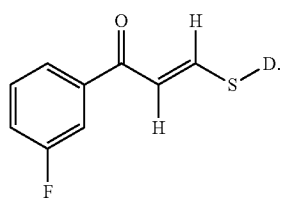

Formula (Ic)

14. The method of claim 1, wherein the compound of Formula (I) has the structure of Formula (Id), or a pharmaceutically acceptable salt thereof:

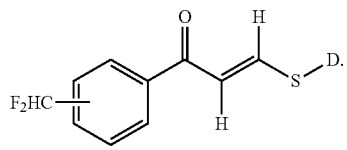

Formula (Id)

15. The method of claim 1, wherein the compound of Formula (I) has the structure of Formula (Ie), or a pharmaceutically acceptable salt thereof:

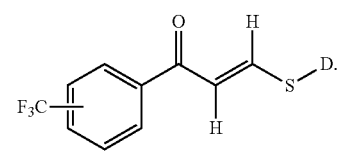

Formula (Ie)

16. The method of claim 1, wherein the compound of Formula (I) has the structure of Formula (If), or a pharmaceutically acceptable salt thereof:

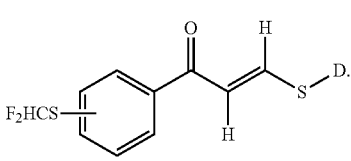

Formula (If)

17. The method of claim 1, wherein the compound of Formula (I) has the structure of Formula (Ig), or a pharmaceutically acceptable salt thereof:

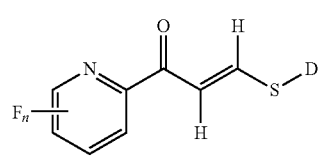

Formula (Ig)

wherein n is 1 or 2.

18. The method of claim 1, wherein D is selected from

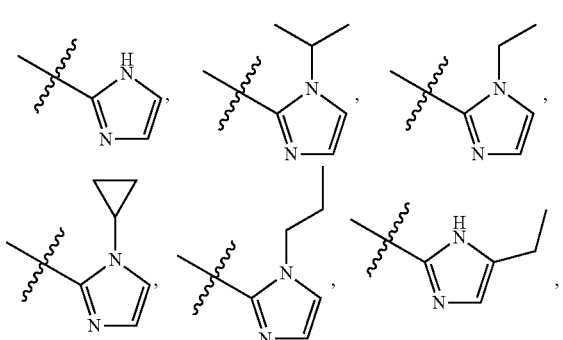

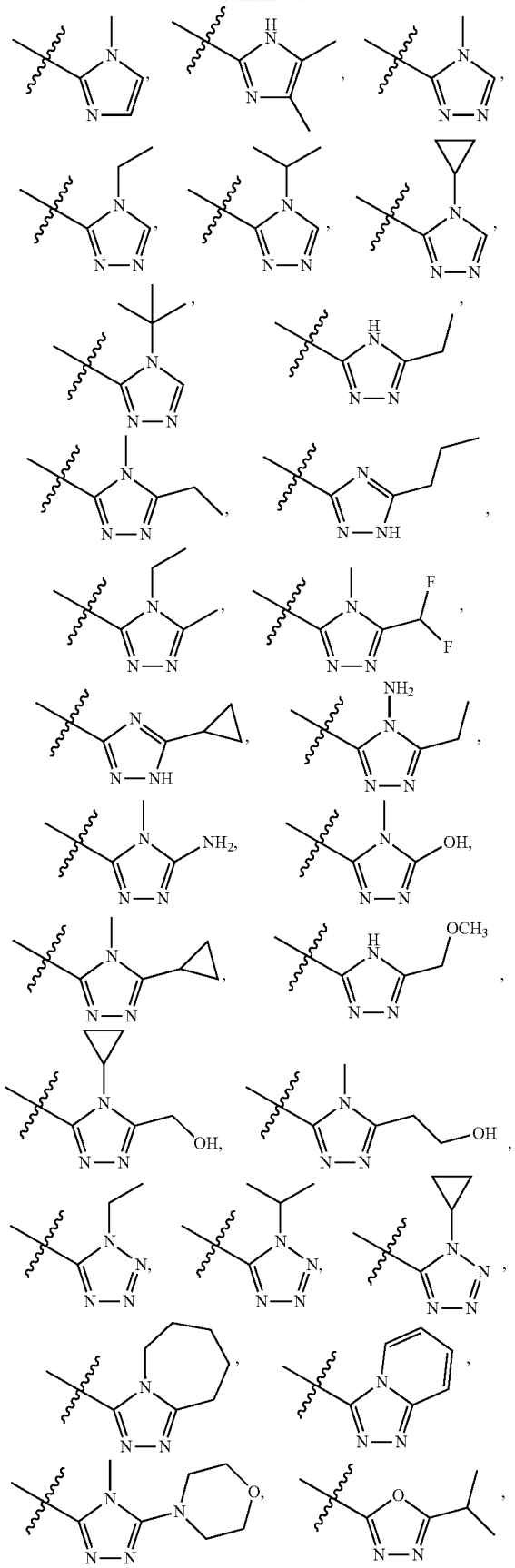
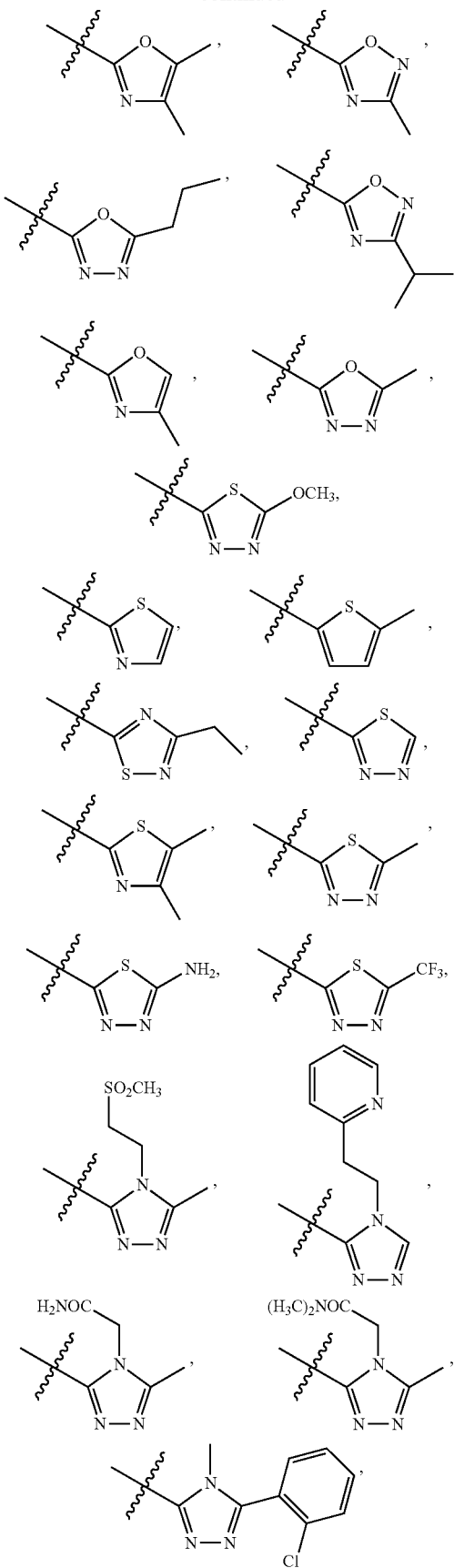

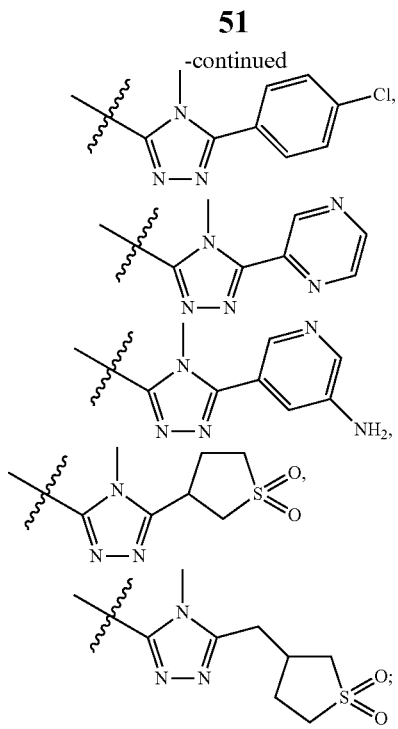
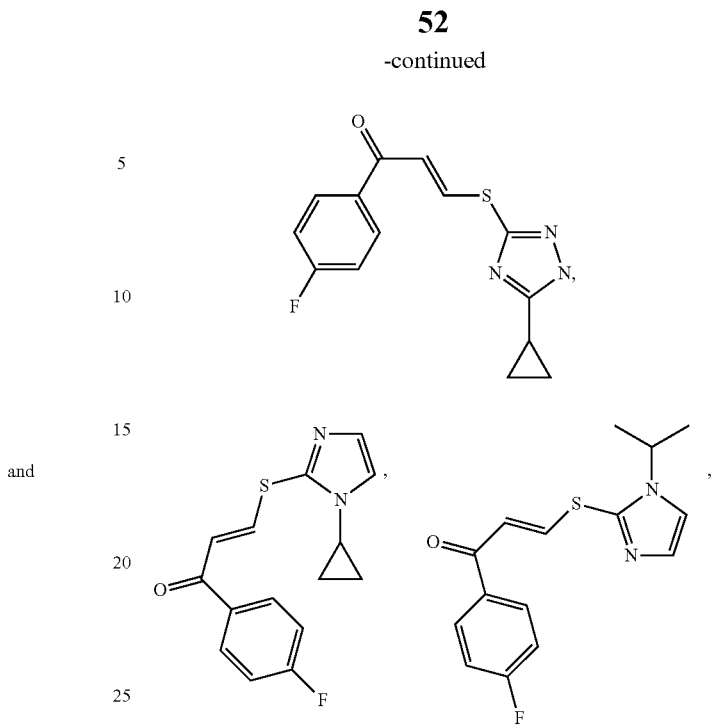
provided that:
i. when A is unsubstituted phenyl, 4-methylphenyl, 4-methoxyphenyl, or 4-chlorophenyl, D is not
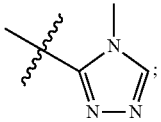 [SMILES: *c1nncn1C]
and
ii. when A is 4-fluorophenyl, D is not
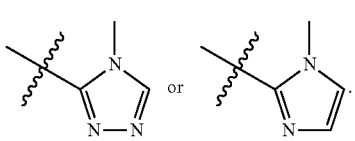
19. The method of claim 1, wherein the compound of Formula (I) is selected from compounds
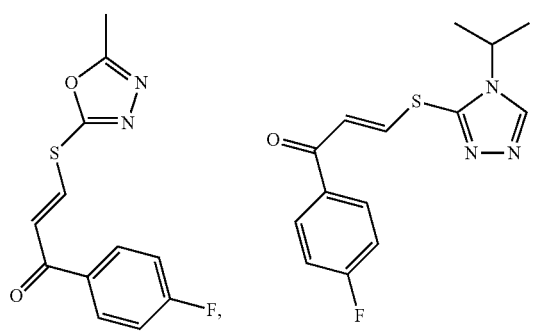
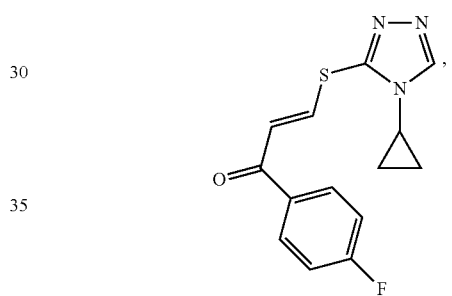
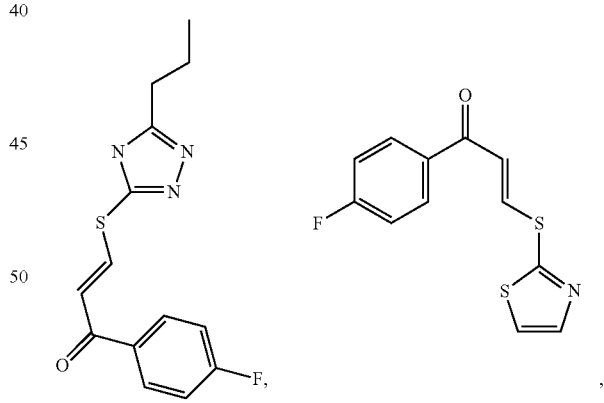
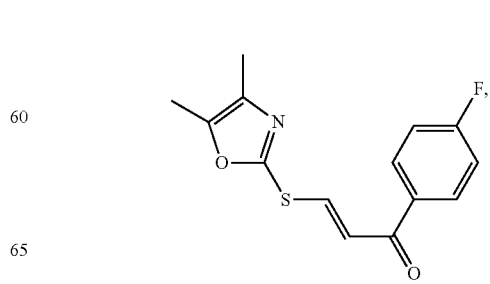

53
-continued
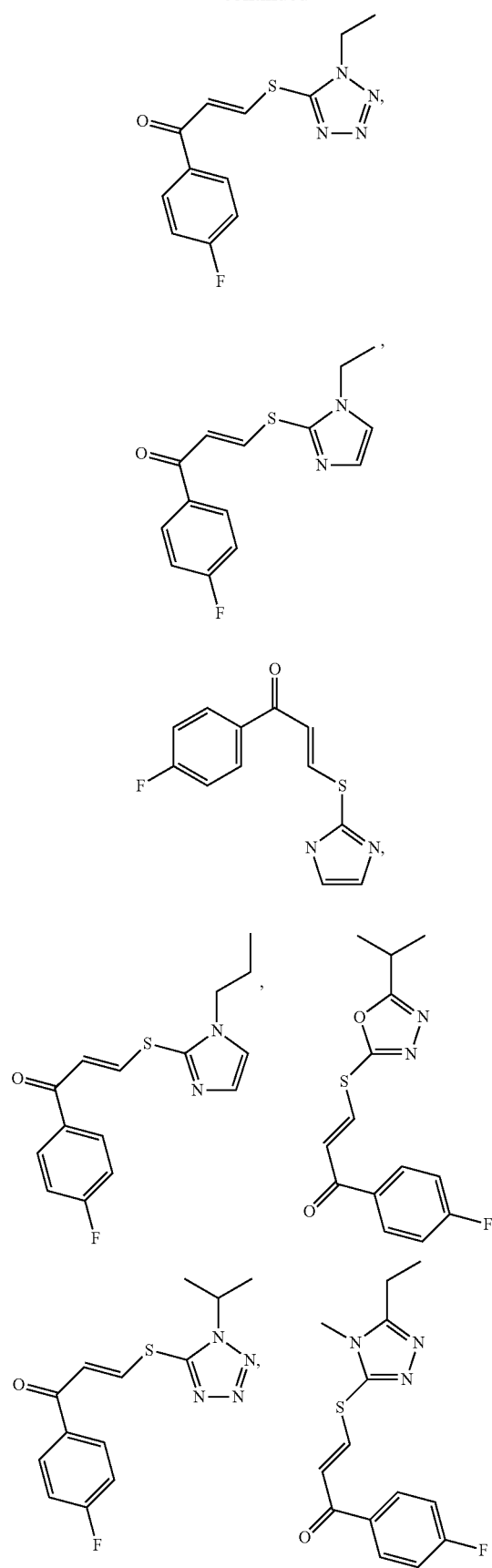
54
-continued
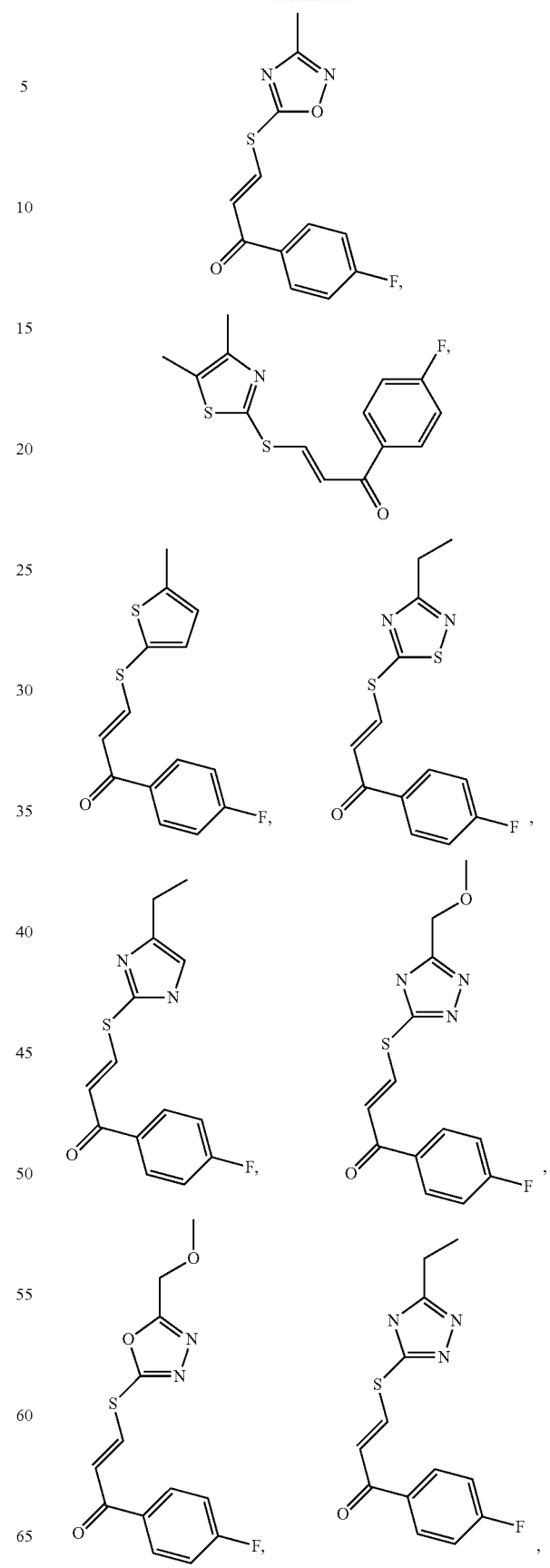

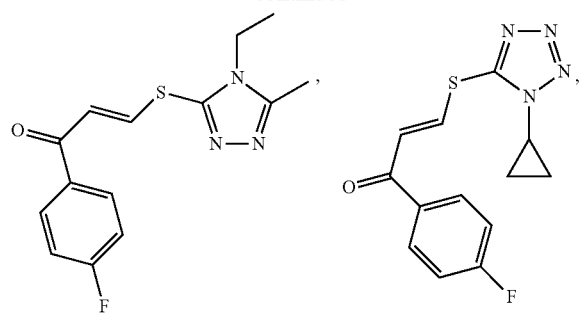
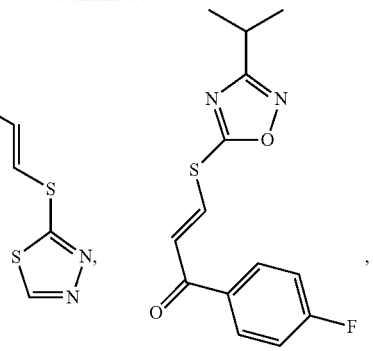
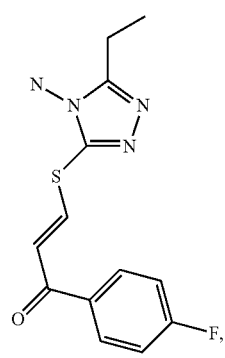
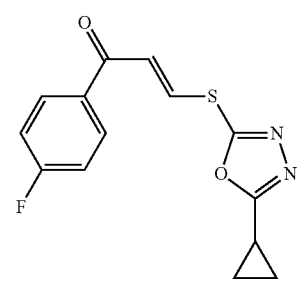
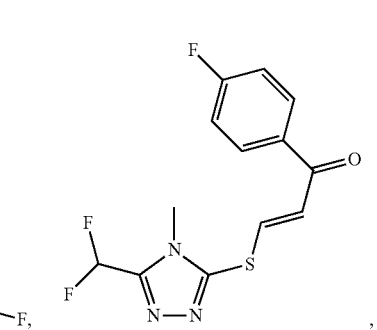
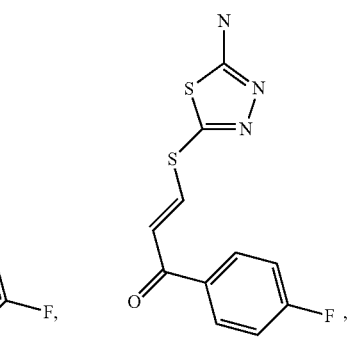
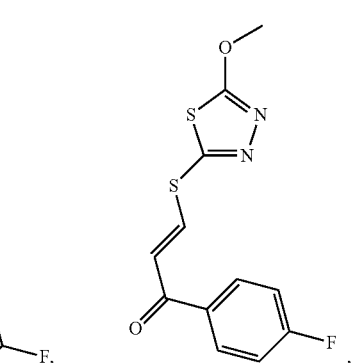
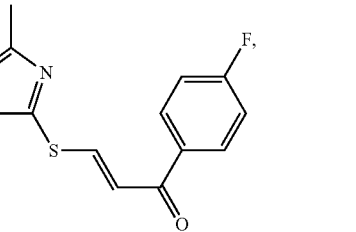

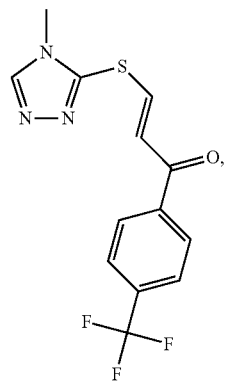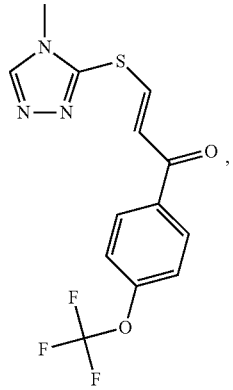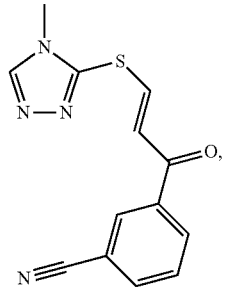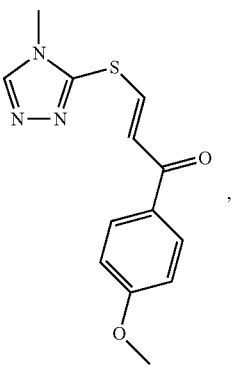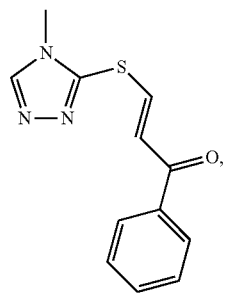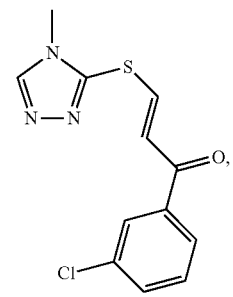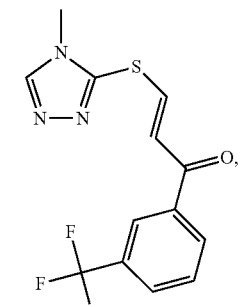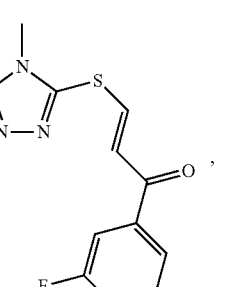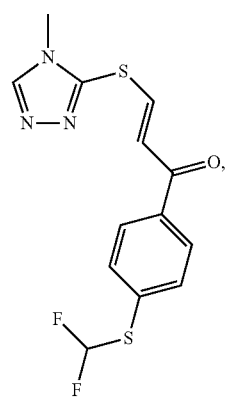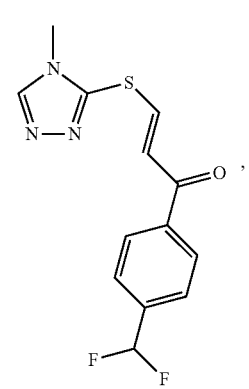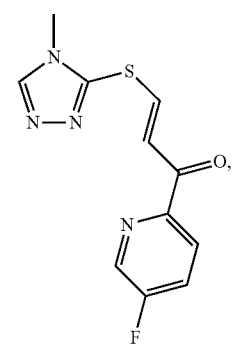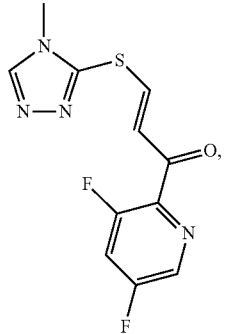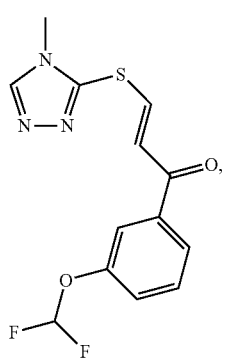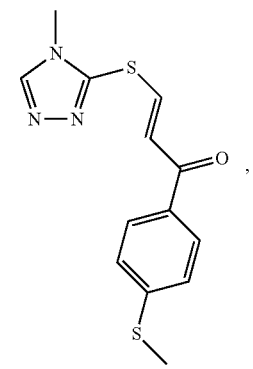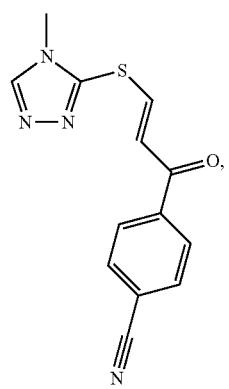

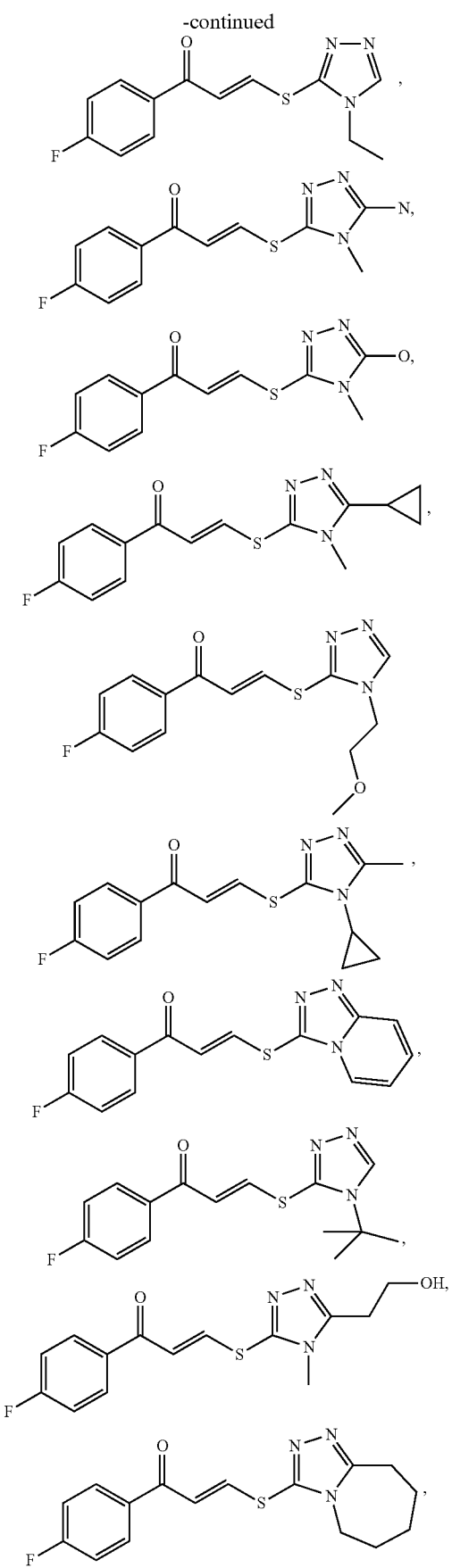

-continued
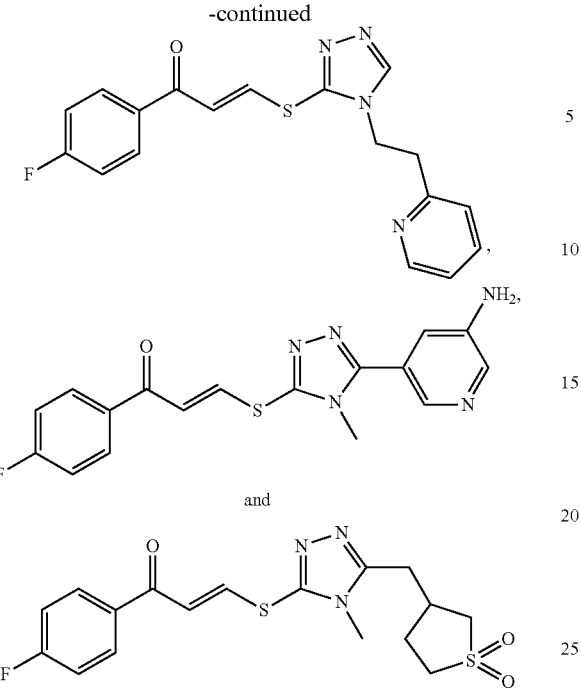
and pharmaceutically acceptable salts thereof.
* * * * *

UNITED STATES PATENT AND TRADEMARK OFFICE
CERTIFICATE OF CORRECTION

PATENT NO. : 9,873,705 B2  
APPLICATION NO. : 15/282644  
DATED : January 23, 2018  
INVENTOR(S) : Sanchez et al.

Page 1 of 1

It is certified that error appears in the above-identified patent and that said Letters Patent is hereby corrected as shown below:

In the Specification

At Column 1, Line 9 insert:
--GOVERNMENT RIGHTS
This invention was made with government support under grant numbers NS060940 and NS095411 awarded by the National Institutes of Health. The government has certain rights in the invention.--

Signed and Sealed this  
Third Day of September, 2019

Andrei Iancu  
*Director of the United States Patent and Trademark Office*